(12) United States Patent
Nagai et al.

(10) Patent No.: US 11,028,390 B2
(45) Date of Patent: Jun. 8, 2021

(54) ANTISENSE OLIGONUCLEOTIDE CONTROLLING EXPRESSION AMOUNT OF TDP-43 AND USE THEREOF

(71) Applicants: OSAKA UNIVERSITY, Suita (JP); KNC LABORATORIES CO., LTD., Kobe (JP); Aichi Medical University, Nagakute (JP)

(72) Inventors: Yoshitaka Nagai, Suita (JP); Kazuhiro Maeta, Suita (JP); Toshihide Takeuchi, Suita (JP); Masahiro Neya, Kobe (JP); Tsuyoshi Fujihara, Kobe (JP); Seiji Matsuda, Kobe (JP); Gen Sobue, Nagoya (JP); Shinsuke Ishigaki, Nagoya (JP); Kentaro Sahashi, Nagoya (JP)

(73) Assignees: Osaka University, Suita (JP); KNC Laboratories Co., Ltd., Kobe (JP); Aichi Medical University, Nagakute (JP)

( * ) Notice: Subject to any disclaimer, the term of this patent is extended or adjusted under 35 U.S.C. 154(b) by 0 days.

(21) Appl. No.: 16/630,141

(22) PCT Filed: Jul. 6, 2018

(86) PCT No.: PCT/JP2018/025792
§ 371 (c)(1),
(2) Date: Jan. 10, 2020

(87) PCT Pub. No.: WO2019/013141
PCT Pub. Date: Jan. 17, 2019

(65) Prior Publication Data
US 2020/0165610 A1    May 28, 2020

(30) Foreign Application Priority Data
Jul. 10, 2017   (JP) .............................. JP2017-134890

(51) Int. Cl.
*A61K 48/00*    (2006.01)
*C12N 15/11*    (2006.01)
(Continued)

(52) U.S. Cl.
CPC .......... *C12N 15/113* (2013.01); *A61K 31/712* (2013.01); *A61P 25/28* (2018.01)

(58) Field of Classification Search
CPC .... C12N 15/113; A61K 31/712; A61K 48/00; A61P 25/28
See application file for complete search history.

(56) References Cited

U.S. PATENT DOCUMENTS

| | | |
|---|---|---|
| 2007/0009899 A1 | 1/2007 | Mounts |
| 2011/0321179 A1 | 12/2011 | Shen et al. |
| 2017/0226508 A1 | 8/2017 | Inoue et al. |

FOREIGN PATENT DOCUMENTS

| | | | |
|---|---|---|---|
| JP | 2017-071572 A | 4/2017 | |
| WO | WO-2009090639 A2 * | 7/2009 | .............. A61P 11/00 |

(Continued)

OTHER PUBLICATIONS

Sato et al. (Oligonucleotides, 2007 vol. 17:291-301).*
(Continued)

*Primary Examiner* — Terra C Gibbs
(74) *Attorney, Agent, or Firm* — Leydig, Voit & Mayer, Ltd.

(57) ABSTRACT

The present invention provides a suppression type antisense oligonucleotide targeting TDP-43 mRNA, containing a nucleotide sequence complementary to a sequence consisting of at least 10 continuous nucleotides in a nucleotide sequence shown in any of SEQ ID NOs: 2-4, and a promotion type antisense oligonucleotide targeting TDP-43 mRNA, containing a nucleotide sequence complementary to
(Continued)

a sequence consisting of at least 10 continuous nucleotides in a nucleotide sequence shown in SEQ ID NO: 5.

16 Claims, 8 Drawing Sheets

Specification includes a Sequence Listing.

(51) Int. Cl.
*C07H 21/02* (2006.01)
*C07H 21/04* (2006.01)
*C12N 15/113* (2010.01)
*A61P 25/28* (2006.01)
*A61K 31/712* (2006.01)

(56) References Cited

FOREIGN PATENT DOCUMENTS

| WO | WO 2011/005793 A1 | 1/2011 | |
|---|---|---|---|
| WO | WO-2012174666 A1 * | 12/2012 | ........... C12N 15/113 |
| WO | WO 2013/173635 A1 | 11/2013 | |
| WO | WO 2014/077693 A1 | 5/2014 | |
| WO | WO 2016/088797 A1 | 6/2016 | |

OTHER PUBLICATIONS

Scanlon, KJ (Current Pharmaceutical Biotechnology, 2004 vol. 5:415-420).*
Arai et al., "TDP-43 is a component of ubiquitin-positive tau-negative inclusions in frontotemporal lobar degeneration and amyotrophic lateral sclerosis," *Biochem. Biophys. Res. Commun.*, 351(3): 602-611 (2006).
Ariizumi, "Reduced Expression of TDP-43 Changes the Structures of Subcellular Organelles," *Niigata Medical Journal*, 125: 482-497 (2011).
Aulas et al., "Endogenous TDP-43, but not FUS, contributes to stress granule assembly via G3BP," *Mol. Neurodegener.*, 7: 54 (2012).
Bhandare et al., "Identification of possible siRNA molecules for TDP43 mutants causing amyotrophic lateral sclerosis: In silico design and molecular dynamics study," *Comput. Biol. Chem.*, 61: 97-108 (2016).
Bhardwaj et al., "Characterizing TDP-43 interaction with its RNA targets," *Nucleic Acids Res.*, 41(9): 5062-5074 (2013).
Buratti et al., "Nuclear factor TDP-43 and SR proteins promote in vitro and in vivo CTFR exon 9 skipping," *EMBO J.*, 20(7): 1774-1784 (2001).
Genbank, "*Homo sapiens* TAR DNA binding protein, mRNA (cDNA clone Image:3506121)," Accession No. BC001487.2 (2007) [obtained at: https://www.ncbi.nlm.nih.gov/nuccore/BC001487.2].
Iguchi et al., "TDP-43 Depletion Induces Neuronal Cell Damage through Dysregulation of Rho Family GTPases," *J. Biol. Chem.*, 284(33): 22059-22066 (2009).
Kabashi et al., "FUS and TARDBP but Not SOD1 Interact in Genetic Models of Amyotrophic Lateral Sclerosis," *PLoS Genet.*, 7(8): e1002214 (2011).
Koyama et al., "Increased cytoplasmic TARDBP mRNA in affected spinal motor neurons in ALS caused by abnormal autoregulation of TDP-43," *Nucleic Acids Res.*, 44(12): 5820-5836 (2016).
Ling et al., "Converging Mechanisms in ALS and FTD: Disrupted RNA and Protein Homeostasis," *Neuron*, 79(3): 416-438 (2013).
Neumann et al., "Ubiquitinated TDP-43 in Frontotemporal Lobar Degeneration and Amyotrophic Lateral Sclerosis," *Science*, 314: 130-133 (2006).
Polymenidou et al., "Long pre-mRNA depletion and RNA missplicing contribute to neuronal vulnerability from loss of TDP-43," *Nat. Neurosci.*, 14(4): 459-468 (2014).
Scotter et al., "TDP-43 Proteinopathy and ALS: Insights into Disease Mechanisms and Therapeutic Targets," *Neurotherapeutics*, 12(2): 352-363 (2015).
Sugai, "Endogenous TDP-43 Overexpression with Disrupted Autoregulation: Toward an Amyotrophic Lateral Sclerosis Model," *Niigata Medical Journal*, 129(11): 658-670 (2015).
Yu et al., "Neurodegeneration-associated TDP-43 Interacts with Fragile X Mental Retardation Protein (FMRP)/Staufen (STAU1) and Regulates SIRT1 Expression in Neuronal Cells," *J. Biol. Chem.*, 287(27): 22560-22572 and Supplementary Tables S1-S2 (2012).
Japanese Patent Office, International Search Report in International Patent Application No. PCT/JP2018/025972 (dated Sep. 25, 2018).
Kole et al., "Rna therapeutics: beyond Rna interference and antisense oligonucleotides," Nat. Rev. Drug Discov., 1 1 (2): 125-140 (2012).
Vickers et al., "Efficient Reduction of Target RNAs by Small Interfering Rna and RNase H-dependent Antisense Agents," J. Biol. Chem., 278(9): 7108-7118 (2003).
Pan et al., "Antisense Applications for Biological Control," J. Cell. Biochem., 98(1): 14-35 (2006).
Watts et al., "Gene silencing by siRNAs and antisense oligonucleotides in the laboratory and the clinic," *J. Pathol.*, 226(2): 365-379 (2012).

* cited by examiner

SEQUENCE LISTING

<160> NUMBER OF SEQ ID NOS: 101

<210> SEQ ID NO 1
<211> LENGTH: 36
<212> TYPE: RNA
<213> ORGANISM: Homo sapiens

<400> SEQUENCE: 1
aucauuaaag gaaucagcgu ucauauaucc aaugcc                                 36

<210> SEQ ID NO 2
<211> LENGTH: 38
<212> TYPE: RNA
<213> ORGANISM: Homo sapiens

<400> SEQUENCE: 2
gaucauuaaa ggaaucagcg uucauauauc caaugccg                               38

<210> SEQ ID NO 3
<211> LENGTH: 51
<212> TYPE: RNA
<213> ORGANISM: Homo sapiens

<400> SEQUENCE: 3
augucugaau auauucgggu aaccgaagau gagaacgaug agcccauuga a                51

<210> SEQ ID NO 4

```
<211> LENGTH: 60
<212> TYPE: RNA
<213> ORGANISM: Homo sapiens

<400> SEQUENCE: 4
cuugucuccc cucauacaca aaaguacaau augaagccuu cauuuaaucu cugcaguuca      60

<210> SEQ ID NO 5
<211> LENGTH: 22
<212> TYPE: RNA
<213> ORGANISM: Homo sapiens

<400> SEQUENCE: 5
ugcuuugcag gaggacuuga ag                                              22

<210> SEQ ID NO 6
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA:Combined DNA/RNA Molecule: nucleotides 6 to
      15 are deoxyribonucleotides-other nucleotides are ribonucleotides
<220> FEATURE:
<221> NAME/KEY: misc_feature
<222> LOCATION: (1)..(20)
<223> OTHER INFORMATION: Phosphorothioate internucleotide linkages
<220> FEATURE:
<221> NAME/KEY: modified_base
<222> LOCATION: (1)..(5)
<223> OTHER INFORMATION: 2'-O,4'-C-ethylene-linked bicyclic
      ribonucleotide
<220> FEATURE:
<221> NAME/KEY: modified_base
<222> LOCATION: (16)..(20)
<223> OTHER INFORMATION: 2'-O,4'-C-ethylene-linked bicyclic
      ribonucleotide

<400> SEQUENCE: 6
gggctcatcg ttctcatctt                                                 20

<210> SEQ ID NO 7
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA:Combined DNA/RNA Molecule: nucleotides 6 to
      15 are deoxyribonucleotides-other nucleotides are ribonucleotides
<220> FEATURE:
<221> NAME/KEY: misc_feature
<222> LOCATION: (1)..(20)
<223> OTHER INFORMATION: Phosphorothioate internucleotide linkages
<220> FEATURE:
<221> NAME/KEY: modified_base
<222> LOCATION: (1)..(5)
<223> OTHER INFORMATION: 2'-O,4'-C-ethylene-linked bicyclic
      ribonucleotide
<220> FEATURE:
<221> NAME/KEY: modified_base
<222> LOCATION: (16)..(20)
<223> OTHER INFORMATION: 2'-O,4'-C-ethylene-linked bicyclic
      ribonucleotide

<400> SEQUENCE: 7
ttcaatgggc tcatcgttct                                                 20

<210> SEQ ID NO 8
<211> LENGTH: 20
<212> TYPE: DNA
<213> ORGANISM: Artificial Sequence
```

```
<220> FEATURE:
<223> OTHER INFORMATION: Synthetic Sequence - antisense oligonucleotide
      targeting TDP-43 mRNA:Combined DNA/RNA Molecule: nucleotides 6 to
      15 are deoxyribonucleotides-other nucleotides are ribonucleotides
<220> FEATURE:
<220> FEATURE:
<221> NAME/KEY: misc_feature
<222> LOCATION: (1)..(20)
<223> OTHER INFORMATION: Phosphorothioate internucleotide linkages
<220> FEATURE:
<221> NAME/KEY: modified_base
<222> LOCATION: (1)..(5)
<223> OTHER INFORMATION: 2'-O,4'-C-ethylene-linked bicyclic
      ribonucleotide
<220> FEATURE:
<221> NAME/KEY: modified_base
<222> LOCATION: (16)..(20)
<223> OTHER INFORMATION: 2'-O,4'-C-ethylene-linked bicyclic
      ribonucleotide

<400> SEQUENCE: 8
cagtcttaag atctttcttg                                              20

<210> SEQ ID NO 9
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA:Combined DNA/RNA Molecule: nucleotides 6 to
      15 are deoxyribonucleotides-other nucleotides are ribonucleotides
<220> FEATURE:
<221> NAME/KEY: misc_feature
<222> LOCATION: (1)..(20)
<223> OTHER INFORMATION: Phosphorothioate internucleotide linkages
<220> FEATURE:
<221> NAME/KEY: modified_base
<222> LOCATION: (1)..(5)
<223> OTHER INFORMATION: 2'-O,4'-C-ethylene-linked bicyclic
      ribonucleotide
<220> FEATURE:
<221> NAME/KEY: modified_base
<222> LOCATION: (16)..(20)
<223> OTHER INFORMATION: 2'-O,4'-C-ethylene-linked bicyclic
      ribonucleotide

<400> SEQUENCE: 9
caaaggctca tcttggcttt                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA:Combined DNA/RNA Molecule: nucleotides 6 to
      15 are deoxyribonucleotides-other nucleotides are ribonucleotides
<220> FEATURE:
<221> NAME/KEY: misc_feature
<222> LOCATION: (1)..(20)
<223> OTHER INFORMATION: Phosphorothioate internucleotide linkages
<220> FEATURE:
<221> NAME/KEY: modified_base
<222> LOCATION: (1)..(5)
<223> OTHER INFORMATION: 2'-O,4'-C-ethylene-linked bicyclic
      ribonucleotide
<220> FEATURE:
<221> NAME/KEY: modified_base
<222> LOCATION: (16)..(20)
<223> OTHER INFORMATION: 2'-O,4'-C-ethylene-linked bicyclic
      ribonucleotide

<400> SEQUENCE: 10
ttaatgatca agtcctctcc                                              20
```

```
<210> SEQ ID NO 11
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA:Combined DNA/RNA Molecule: nucleotides 6 to
      15 are deoxyribonucleotides-other nucleotides are ribonucleotides
<220> FEATURE:
<221> NAME/KEY: misc_feature
<222> LOCATION: (1)..(20)
<223> OTHER INFORMATION: Phosphorothioate internucleotide linkages
<220> FEATURE:
<221> NAME/KEY: modified_base
<222> LOCATION: (1)..(5)
<223> OTHER INFORMATION: 2'-O,4'-C-ethylene-linked bicyclic
      ribonucleotide
<220> FEATURE:
<221> NAME/KEY: modified_base
<222> LOCATION: (16)..(20)
<223> OTHER INFORMATION: 2'-O,4'-C-ethylene-linked bicyclic
      ribonucleotide

<400> SEQUENCE: 11
atatatgaac gctgattcct                                              20

<210> SEQ ID NO 12
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA:Combined DNA/RNA Molecule: nucleotides 6 to
      15 are deoxyribonucleotides-other nucleotides are ribonucleotides
<220> FEATURE:
<221> NAME/KEY: misc_feature
<222> LOCATION: (1)..(20)
<223> OTHER INFORMATION: Phosphorothioate internucleotide linkages
<220> FEATURE:
<221> NAME/KEY: modified_base
<222> LOCATION: (1)..(5)
<223> OTHER INFORMATION: 2'-O,4'-C-ethylene-linked bicyclic
      ribonucleotide
<220> FEATURE:
<221> NAME/KEY: modified_base
<222> LOCATION: (16)..(20)
<223> OTHER INFORMATION: 2'-O,4'-C-ethylene-linked bicyclic
      ribonucleotide

<400> SEQUENCE: 12
gtgcttaggt taggcattgg                                              20

<210> SEQ ID NO 13
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA:Combined DNA/RNA Molecule: nucleotides 6 to
      15 are deoxyribonucleotides-other nucleotides are ribonucleotides
<220> FEATURE:
<221> NAME/KEY: misc_feature
<222> LOCATION: (1)..(20)
<223> OTHER INFORMATION: Phosphorothioate internucleotide linkages
<220> FEATURE:
<221> NAME/KEY: modified_base
<222> LOCATION: (1)..(5)
<223> OTHER INFORMATION: 2'-O,4'-C-ethylene-linked bicyclic
      ribonucleotide
<220> FEATURE:
<221> NAME/KEY: modified_base
<222> LOCATION: (16)..(20)
<223> OTHER INFORMATION: 2'-O,4'-C-ethylene-linked bicyclic
``` ribonucleotide

<400> SEQUENCE: 13
atccatgctt gagccaaagc                                                    20

<210> SEQ ID NO 14
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA:Combined DNA/RNA Molecule: nucleotides 6 to
      15 are deoxyribonucleotides-other nucleotides are ribonucleotides
<220> FEATURE:
<221> NAME/KEY: misc_feature
<222> LOCATION: (1)..(20)
<223> OTHER INFORMATION: Phosphorothioate internucleotide linkages
<220> FEATURE:
<221> NAME/KEY: modified_base
<222> LOCATION: (1)..(5)
<223> OTHER INFORMATION: 2'-O,4'-C-ethylene-linked bicyclic
      ribonucleotide
<220> FEATURE:
<221> NAME/KEY: modified_base
<222> LOCATION: (16)..(20)
<223> OTHER INFORMATION: 2'-O,4'-C-ethylene-linked bicyclic
      ribonucleotide

<400> SEQUENCE: 14
aaggcttcat attgtactt                                                     20

<210> SEQ ID NO 15
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA:Combined DNA/RNA Molecule: nucleotides 6 to
      15 are deoxyribonucleotides-other nucleotides are ribonucleotides
<220> FEATURE:
<221> NAME/KEY: misc_feature
<222> LOCATION: (1)..(20)
<223> OTHER INFORMATION: Phosphorothioate internucleotide linkages
<220> FEATURE:
<221> NAME/KEY: modified_base
<222> LOCATION: (1)..(5)
<223> OTHER INFORMATION: 2'-O,4'-C-ethylene-linked bicyclic
      ribonucleotide
<220> FEATURE:
<221> NAME/KEY: modified_base
<222> LOCATION: (16)..(20)
<223> OTHER INFORMATION: 2'-O,4'-C-ethylene-linked bicyclic
      ribonucleotide

<400> SEQUENCE: 15
aatatccatt atgcaccacc                                                    20

<210> SEQ ID NO 16
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA:Combined DNA/RNA Molecule: nucleotides 6 to
      15 are deoxyribonucleotides-other nucleotides are ribonucleotides
<220> FEATURE:
<221> NAME/KEY: misc_feature
<222> LOCATION: (1)..(20)
<223> OTHER INFORMATION: Phosphorothioate internucleotide linkages
<220> FEATURE:
<221> NAME/KEY: modified_base
<222> LOCATION: (1)..(5)
<223> OTHER INFORMATION: 2'-O,4'-C-ethylene-linked bicyclic

```
              ribonucleotide
<220> FEATURE:
<221> NAME/KEY: modified_base
<222> LOCATION: (16)..(20)
<223> OTHER INFORMATION: 2'-O,4'-C-ethylene-linked bicyclic
      ribonucleotide

<400> SEQUENCE: 16
gtgcttaggt tcggcattgg                                            20

<210> SEQ ID NO 17
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA:Combined DNA/RNA Molecule: nucleotides 6 to
      15 are deoxyribonucleotides-other nucleotides are ribonucleotides
<220> FEATURE:
<221> NAME/KEY: misc_feature
<222> LOCATION: (1)..(20)
<223> OTHER INFORMATION: Phosphorothioate internucleotide linkages
<220> FEATURE:
<221> NAME/KEY: modified_base
<222> LOCATION: (1)..(5)
<223> OTHER INFORMATION: 2'-O,4'-C-ethylene-linked bicyclic
      ribonucleotide
<220> FEATURE:
<221> NAME/KEY: modified_base
<222> LOCATION: (16)..(20)
<223> OTHER INFORMATION: 2'-O,4'-C-ethylene-linked bicyclic
      ribonucleotide

<400> SEQUENCE: 17
ctttaatgat caagtcctct                                            20

<210> SEQ ID NO 18
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA:Combined DNA/RNA Molecule: nucleotides 6 to
      15 are deoxyribonucleotides-other nucleotides are ribonucleotides
<220> FEATURE:
<221> NAME/KEY: misc_feature
<222> LOCATION: (1)..(20)
<223> OTHER INFORMATION: Phosphorothioate internucleotide linkages
<220> FEATURE:
<221> NAME/KEY: modified_base
<222> LOCATION: (1)..(5)
<223> OTHER INFORMATION: 2'-O,4'-C-ethylene-linked bicyclic
      ribonucleotide
<220> FEATURE:
<221> NAME/KEY: modified_base
<222> LOCATION: (16)..(20)
<223> OTHER INFORMATION: 2'-O,4'-C-ethylene-linked bicyclic
      ribonucleotide

<400> SEQUENCE: 18
tcctttaatg atcaagtcct                                            20

<210> SEQ ID NO 19
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA:Combined DNA/RNA Molecule: nucleotides 6 to
      15 are deoxyribonucleotides-other nucleotides are ribonucleotides
<220> FEATURE:
<221> NAME/KEY: misc_feature
<222> LOCATION: (1)..(20)
```

<223> OTHER INFORMATION: Phosphorothioate internucleotide linkages
<220> FEATURE:
<221> NAME/KEY: modified_base
<222> LOCATION: (1)..(5)
<223> OTHER INFORMATION: 2'-O,4'-C-ethylene-linked bicyclic
      ribonucleotide
<220> FEATURE:
<221> NAME/KEY: modified_base
<222> LOCATION: (16)..(20)
<223> OTHER INFORMATION: 2'-O,4'-C-ethylene-linked bicyclic
      ribonucleotide

<400> SEQUENCE: 19
attcctttaa tgatcaagtc                                              20

<210> SEQ ID NO 20
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA:Combined DNA/RNA Molecule: nucleotides 6 to
      15 are deoxyribonucleotides-other nucleotides are ribonucleotides
<220> FEATURE:
<221> NAME/KEY: misc_feature
<222> LOCATION: (1)..(20)
<223> OTHER INFORMATION: Phosphorothioate internucleotide linkages
<220> FEATURE:
<221> NAME/KEY: modified_base
<222> LOCATION: (1)..(5)
<223> OTHER INFORMATION: 2'-O,4'-C-ethylene-linked bicyclic
      ribonucleotide
<220> FEATURE:
<221> NAME/KEY: modified_base
<222> LOCATION: (16)..(20)
<223> OTHER INFORMATION: 2'-O,4'-C-ethylene-linked bicyclic
      ribonucleotide

<400> SEQUENCE: 20
tgattccttt aatgatcaag                                              20

<210> SEQ ID NO 21
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA:Combined DNA/RNA Molecule: nucleotides 6 to
      15 are deoxyribonucleotides-other nucleotides are ribonucleotides
<220> FEATURE:
<221> NAME/KEY: misc_feature
<222> LOCATION: (1)..(20)
<223> OTHER INFORMATION: Phosphorothioate internucleotide linkages
<220> FEATURE:
<221> NAME/KEY: modified_base
<222> LOCATION: (1)..(5)
<223> OTHER INFORMATION: 2'-O,4'-C-ethylene-linked bicyclic
      ribonucleotide
<220> FEATURE:
<221> NAME/KEY: modified_base
<222> LOCATION: (16)..(20)
<223> OTHER INFORMATION: 2'-O,4'-C-ethylene-linked bicyclic
      ribonucleotide

<400> SEQUENCE: 21
gctgattcct ttaatgatca                                              20

<210> SEQ ID NO 22
<211> LENGTH: 20
<212> TYPE: DNA
<213> ORGANISM: Artificial Sequence
<220> FEATURE:
<223> OTHER INFORMATION: Synthetic Sequence - antisense oligonucleotide

```
      targeting TDP-43 mRNA:Combined DNA/RNA Molecule: nucleotides 6 to
      15 are deoxyribonucleotides-other nucleotides are ribonucleotides
<220> FEATURE:
<221> NAME/KEY: misc_feature
<222> LOCATION: (1)..(20)
<223> OTHER INFORMATION: Phosphorothioate internucleotide linkages
<220> FEATURE:
<221> NAME/KEY: modified_base
<222> LOCATION: (1)..(5)
<223> OTHER INFORMATION: 2'-O,4'-C-ethylene-linked bicyclic
      ribonucleotide
<220> FEATURE:
<221> NAME/KEY: modified_base
<222> LOCATION: (16)..(20)
<223> OTHER INFORMATION: 2'-O,4'-C-ethylene-linked bicyclic
      ribonucleotide

<400> SEQUENCE: 22
acgctgattc ctttaatgat                                              20

<210> SEQ ID NO 23
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA:Combined DNA/RNA Molecule: nucleotides 6 to
      15 are deoxyribonucleotides-other nucleotides are ribonucleotides
<220> FEATURE:
<221> NAME/KEY: misc_feature
<222> LOCATION: (1)..(20)
<223> OTHER INFORMATION: Phosphorothioate internucleotide linkages
<220> FEATURE:
<221> NAME/KEY: modified_base
<222> LOCATION: (1)..(5)
<223> OTHER INFORMATION: 2'-O,4'-C-ethylene-linked bicyclic
      ribonucleotide
<220> FEATURE:
<221> NAME/KEY: modified_base
<222> LOCATION: (16)..(20)
<223> OTHER INFORMATION: 2'-O,4'-C-ethylene-linked bicyclic
      ribonucleotide

<400> SEQUENCE: 23
gaacgctgat tcctttaatg                                              20

<210> SEQ ID NO 24
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA:Combined DNA/RNA Molecule: nucleotides 6 to
      15 are deoxyribonucleotides-other nucleotides are ribonucleotides
<220> FEATURE:
<221> NAME/KEY: misc_feature
<222> LOCATION: (1)..(20)
<223> OTHER INFORMATION: Phosphorothioate internucleotide linkages
<220> FEATURE:
<221> NAME/KEY: modified_base
<222> LOCATION: (1)..(5)
<223> OTHER INFORMATION: 2'-O,4'-C-ethylene-linked bicyclic
      ribonucleotide
<220> FEATURE:
<221> NAME/KEY: modified_base
<222> LOCATION: (16)..(20)
<223> OTHER INFORMATION: 2'-O,4'-C-ethylene-linked bicyclic
      ribonucleotide

<400> SEQUENCE: 24
atgaacgctg attcctttaa                                              20

<210> SEQ ID NO 25
```

```
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA:Combined DNA/RNA Molecule: nucleotides 6 to
      15 are deoxyribonucleotides-other nucleotides are ribonucleotides
<220> FEATURE:
<221> NAME/KEY: misc_feature
<222> LOCATION: (1)..(20)
<223> OTHER INFORMATION: Phosphorothioate internucleotide linkages
<220> FEATURE:
<221> NAME/KEY: modified_base
<222> LOCATION: (1)..(5)
<223> OTHER INFORMATION: 2'-O,4'-C-ethylene-linked bicyclic
      ribonucleotide
<220> FEATURE:
<221> NAME/KEY: modified_base
<222> LOCATION: (16)..(20)
<223> OTHER INFORMATION: 2'-O,4'-C-ethylene-linked bicyclic
      ribonucleotide

<400> SEQUENCE: 25
atatgaacgc tgattccttt                                              20

<210> SEQ ID NO 26
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA:Combined DNA/RNA Molecule: nucleotides 6 to
      15 are deoxyribonucleotides-other nucleotides are ribonucleotides
<220> FEATURE:
<221> NAME/KEY: misc_feature
<222> LOCATION: (1)..(20)
<223> OTHER INFORMATION: Phosphorothioate internucleotide linkages
<220> FEATURE:
<221> NAME/KEY: modified_base
<222> LOCATION: (1)..(5)
<223> OTHER INFORMATION: 2'-O,4'-C-ethylene-linked bicyclic
      ribonucleotide
<220> FEATURE:
<221> NAME/KEY: modified_base
<222> LOCATION: (16)..(20)
<223> OTHER INFORMATION: 2'-O,4'-C-ethylene-linked bicyclic
      ribonucleotide

<400> SEQUENCE: 26
ggatatatga acgctgattc                                              20

<210> SEQ ID NO 27
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA:Combined DNA/RNA Molecule: nucleotides 6 to
      15 are deoxyribonucleotides-other nucleotides are ribonucleotides
<220> FEATURE:
<221> NAME/KEY: misc_feature
<222> LOCATION: (1)..(20)
<223> OTHER INFORMATION: Phosphorothioate internucleotide linkages
<220> FEATURE:
<221> NAME/KEY: modified_base
<222> LOCATION: (1)..(5)
<223> OTHER INFORMATION: 2'-O,4'-C-ethylene-linked bicyclic
      ribonucleotide
<220> FEATURE:
<221> NAME/KEY: modified_base
<222> LOCATION: (16)..(20)
<223> OTHER INFORMATION: 2'-O,4'-C-ethylene-linked bicyclic
      ribonucleotide

<400> SEQUENCE: 27
```
ttggatatat gaacgctgat                                            20

<210> SEQ ID NO 28
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA:Combined DNA/RNA Molecule: nucleotides 6 to
      15 are deoxyribonucleotides-other nucleotides are ribonucleotides
<220> FEATURE:
<221> NAME/KEY: misc_feature
<222> LOCATION: (1)..(20)
<223> OTHER INFORMATION: Phosphorothioate internucleotide linkages
<220> FEATURE:
<221> NAME/KEY: modified_base
<222> LOCATION: (1)..(5)
<223> OTHER INFORMATION: 2'-O,4'-C-ethylene-linked bicyclic
      ribonucleotide
<220> FEATURE:
<221> NAME/KEY: modified_base
<222> LOCATION: (16)..(20)
<223> OTHER INFORMATION: 2'-O,4'-C-ethylene-linked bicyclic
      ribonucleotide

<400> SEQUENCE: 28
cattggatat atgaacgctg                                            20

<210> SEQ ID NO 29
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA:Combined DNA/RNA Molecule: nucleotides 6 to
      15 are deoxyribonucleotides-other nucleotides are ribonucleotides
<220> FEATURE:
<221> NAME/KEY: misc_feature
<222> LOCATION: (1)..(20)
<223> OTHER INFORMATION: Phosphorothioate internucleotide linkages
<220> FEATURE:
<221> NAME/KEY: modified_base
<222> LOCATION: (1)..(5)
<223> OTHER INFORMATION: 2'-O,4'-C-ethylene-linked bicyclic
      ribonucleotide
<220> FEATURE:
<221> NAME/KEY: modified_base
<222> LOCATION: (16)..(20)
<223> OTHER INFORMATION: 2'-O,4'-C-ethylene-linked bicyclic
      ribonucleotide

<400> SEQUENCE: 29
ggcattggat atatgaacgc                                            20

<210> SEQ ID NO 30
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA:Combined DNA/RNA Molecule: nucleotides 6 to
      15 are deoxyribonucleotides-other nucleotides are ribonucleotides
<220> FEATURE:
<221> NAME/KEY: misc_feature
<222> LOCATION: (1)..(20)
<223> OTHER INFORMATION: Phosphorothioate internucleotide linkages
<220> FEATURE:
<221> NAME/KEY: modified_base
<222> LOCATION: (1)..(5)
<223> OTHER INFORMATION: 2'-O,4'-C-ethylene-linked bicyclic
      ribonucleotide
<220> FEATURE:
<221> NAME/KEY: modified_base -continued
<222> LOCATION: (16)..(20)
<223> OTHER INFORMATION: 2'-O,4'-C-ethylene-linked bicyclic
      ribonucleotide

<400> SEQUENCE: 30
tcggcattgg atatatgaac                                              20

<210> SEQ ID NO 31
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA:Combined DNA/RNA Molecule: nucleotides 6 to
      15 are deoxyribonucleotides-other nucleotides are ribonucleotides
<220> FEATURE:
<221> NAME/KEY: misc_feature
<222> LOCATION: (1)..(20)
<223> OTHER INFORMATION: Phosphorothioate internucleotide linkages
<220> FEATURE:
<221> NAME/KEY: modified_base
<222> LOCATION: (1)..(5)
<223> OTHER INFORMATION: 2'-O,4'-C-ethylene-linked bicyclic
      ribonucleotide
<220> FEATURE:
<221> NAME/KEY: modified_base
<222> LOCATION: (16)..(20)
<223> OTHER INFORMATION: 2'-O,4'-C-ethylene-linked bicyclic
      ribonucleotide

<400> SEQUENCE: 31
gttcggcatt ggatatatga                                              20

<210> SEQ ID NO 32
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA:Combined DNA/RNA Molecule: nucleotides 6 to
      15 are deoxyribonucleotides-other nucleotides are ribonucleotides
<220> FEATURE:
<221> NAME/KEY: misc_feature
<222> LOCATION: (1)..(20)
<223> OTHER INFORMATION: Phosphorothioate internucleotide linkages
<220> FEATURE:
<221> NAME/KEY: modified_base
<222> LOCATION: (1)..(5)
<223> OTHER INFORMATION: 2'-O,4'-C-ethylene-linked bicyclic
      ribonucleotide
<220> FEATURE:
<221> NAME/KEY: modified_base
<222> LOCATION: (16)..(20)
<223> OTHER INFORMATION: 2'-O,4'-C-ethylene-linked bicyclic
      ribonucleotide

<400> SEQUENCE: 32
aggttcggca ttggatatat                                              20

<210> SEQ ID NO 33
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA:Combined DNA/RNA Molecule: nucleotides 6 to
      15 are deoxyribonucleotides-other nucleotides are ribonucleotides
<220> FEATURE:
<221> NAME/KEY: misc_feature
<222> LOCATION: (1)..(20)
<223> OTHER INFORMATION: Phosphorothioate internucleotide linkages
<220> FEATURE:
<221> NAME/KEY: modified_base

```
<222> LOCATION: (1)..(5)
<223> OTHER INFORMATION: 2'-O,4'-C-ethylene-linked bicyclic
      ribonucleotide
<220> FEATURE:
<221> NAME/KEY: modified_base
<222> LOCATION: (16)..(20)
<223> OTHER INFORMATION: 2'-O,4'-C-ethylene-linked bicyclic
      ribonucleotide

<400> SEQUENCE: 33
ttaggttcgg cattggatat                                                 20

<210> SEQ ID NO 34
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA:Combined DNA/RNA Molecule: nucleotides 6 to
      15 are deoxyribonucleotides-other nucleotides are ribonucleotides
<220> FEATURE:
<221> NAME/KEY: misc_feature
<222> LOCATION: (1)..(20)
<223> OTHER INFORMATION: Phosphorothioate internucleotide linkages
<220> FEATURE:
<221> NAME/KEY: modified_base
<222> LOCATION: (1)..(5)
<223> OTHER INFORMATION: 2'-O,4'-C-ethylene-linked bicyclic
      ribonucleotide
<220> FEATURE:
<221> NAME/KEY: modified_base
<222> LOCATION: (16)..(20)
<223> OTHER INFORMATION: 2'-O,4'-C-ethylene-linked bicyclic
      ribonucleotide

<400> SEQUENCE: 34
gcttaggttc ggcattggat                                                 20

<210> SEQ ID NO 35
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA:Combined DNA/RNA Molecule: nucleotides 6 to
      15 are deoxyribonucleotides-other nucleotides are ribonucleotides
<220> FEATURE:
<221> NAME/KEY: misc_feature
<222> LOCATION: (1)..(20)
<223> OTHER INFORMATION: Phosphorothioate internucleotide linkages
<220> FEATURE:
<221> NAME/KEY: modified_base
<222> LOCATION: (1)..(5)
<223> OTHER INFORMATION: 2'-O,4'-C-ethylene-linked bicyclic
      ribonucleotide
<220> FEATURE:
<221> NAME/KEY: modified_base
<222> LOCATION: (16)..(20)
<223> OTHER INFORMATION: 2'-O,4'-C-ethylene-linked bicyclic
      ribonucleotide

<400> SEQUENCE: 35
gatatatgaa cgctgattcc                                                 20

<210> SEQ ID NO 36
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA:Combined DNA/RNA Molecule: nucleotides 6 to
      15 are deoxyribonucleotides-other nucleotides are ribonucleotides
<220> FEATURE:
```

```
<221> NAME/KEY: misc_feature
<222> LOCATION: (1)..(20)
<223> OTHER INFORMATION: Phosphorothioate internucleotide linkages
<220> FEATURE:
<221> NAME/KEY: modified_base
<222> LOCATION: (1)..(5)
<223> OTHER INFORMATION: 2'-O,4'-C-ethylene-linked bicyclic
      ribonucleotide
<220> FEATURE:
<221> NAME/KEY: modified_base
<222> LOCATION: (16)..(20)
<223> OTHER INFORMATION: 2'-O,4'-C-ethylene-linked bicyclic
      ribonucleotide

<400> SEQUENCE: 36
cgctgattcc tttaatgatc                                              20

<210> SEQ ID NO 37
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA:Combined DNA/RNA Molecule: nucleotides 6 to
      15 are deoxyribonucleotides-other nucleotides are ribonucleotides
<220> FEATURE:
<221> NAME/KEY: misc_feature
<222> LOCATION: (1)..(20)
<223> OTHER INFORMATION: Phosphorothioate internucleotide linkages
<220> FEATURE:
<221> NAME/KEY: modified_base
<222> LOCATION: (1)..(5)
<223> OTHER INFORMATION: 2'-O,4'-C-ethylene-linked bicyclic
      ribonucleotide
<220> FEATURE:
<221> NAME/KEY: modified_base
<222> LOCATION: (16)..(20)
<223> OTHER INFORMATION: 2'-O,4'-C-ethylene-linked bicyclic
      ribonucleotide

<400> SEQUENCE: 37
aacgctgatt cctttaatga                                              20

<210> SEQ ID NO 38
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA:Combined DNA/RNA Molecule: nucleotides 6 to
      15 are deoxyribonucleotides-other nucleotides are ribonucleotides
<220> FEATURE:
<221> NAME/KEY: misc_feature
<222> LOCATION: (1)..(20)
<223> OTHER INFORMATION: Phosphorothioate internucleotide linkages
<220> FEATURE:
<221> NAME/KEY: modified_base
<222> LOCATION: (1)..(5)
<223> OTHER INFORMATION: 2'-O,4'-C-ethylene-linked bicyclic
      ribonucleotide
<220> FEATURE:
<221> NAME/KEY: modified_base
<222> LOCATION: (16)..(20)
<223> OTHER INFORMATION: 2'-O,4'-C-ethylene-linked bicyclic
      ribonucleotide

<400> SEQUENCE: 38
tgaacgctga ttcctttaat                                              20

<210> SEQ ID NO 39
<211> LENGTH: 20
<212> TYPE: DNA
<213> ORGANISM: Artificial Sequence
```

```
<220> FEATURE:
<223> OTHER INFORMATION: Synthetic Sequence - antisense oligonucleotide
      targeting TDP-43 mRNA:Combined DNA/RNA Molecule: nucleotides 6 to
      15 are deoxyribonucleotides-other nucleotides are ribonucleotides
<220> FEATURE:
<221> NAME/KEY: misc_feature
<222> LOCATION: (1)..(20)
<223> OTHER INFORMATION: Phosphorothioate internucleotide linkages
<220> FEATURE:
<221> NAME/KEY: modified_base
<222> LOCATION: (1)..(5)
<223> OTHER INFORMATION: 2'-O,4'-C-ethylene-linked bicyclic
      ribonucleotide
<220> FEATURE:
<221> NAME/KEY: modified_base
<222> LOCATION: (16)..(20)
<223> OTHER INFORMATION: 2'-O,4'-C-ethylene-linked bicyclic
      ribonucleotide

<400> SEQUENCE: 39
tatgaacgct gattccttta                                                 20

<210> SEQ ID NO 40
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA:Combined DNA/RNA Molecule: nucleotides 6 to
      15 are deoxyribonucleotides-other nucleotides are ribonucleotides
<220> FEATURE:
<221> NAME/KEY: misc_feature
<222> LOCATION: (1)..(20)
<223> OTHER INFORMATION: Phosphorothioate internucleotide linkages
<220> FEATURE:
<221> NAME/KEY: modified_base
<222> LOCATION: (1)..(5)
<223> OTHER INFORMATION: 2'-O,4'-C-ethylene-linked bicyclic
      ribonucleotide
<220> FEATURE:
<221> NAME/KEY: modified_base
<222> LOCATION: (16)..(20)
<223> OTHER INFORMATION: 2'-O,4'-C-ethylene-linked bicyclic
      ribonucleotide

<400> SEQUENCE: 40
tatatgaacg ctgattcctt                                                 20

<210> SEQ ID NO 41
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA:Combined DNA/RNA Molecule: nucleotides 6 to
      15 are deoxyribonucleotides-other nucleotides are ribonucleotides
<220> FEATURE:
<221> NAME/KEY: misc_feature
<222> LOCATION: (1)..(20)
<223> OTHER INFORMATION: Phosphorothioate internucleotide linkages
<220> FEATURE:
<221> NAME/KEY: modified_base
<222> LOCATION: (1)..(5)
<223> OTHER INFORMATION: 2'-O,4'-C-ethylene-linked bicyclic
      ribonucleotide
<220> FEATURE:
<221> NAME/KEY: modified_base
<222> LOCATION: (16)..(20)
<223> OTHER INFORMATION: 2'-O,4'-C-ethylene-linked bicyclic
      ribonucleotide

<400> SEQUENCE: 41
tggatatatg aacgctgatt                                                 20
```

```
<210> SEQ ID NO 42
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA:Combined DNA/RNA Molecule: nucleotides 6 to
      15 are deoxyribonucleotides-other nucleotides are ribonucleotides
<220> FEATURE:
<221> NAME/KEY: misc_feature
<222> LOCATION: (1)..(20)
<223> OTHER INFORMATION: Phosphorothioate internucleotide linkages
<220> FEATURE:
<221> NAME/KEY: modified_base
<222> LOCATION: (1)..(5)
<223> OTHER INFORMATION: 2'-O,4'-C-ethylene-linked bicyclic
      ribonucleotide
<220> FEATURE:
<221> NAME/KEY: modified_base
<222> LOCATION: (16)..(20)
<223> OTHER INFORMATION: 2'-O,4'-C-ethylene-linked bicyclic
      ribonucleotide

<400> SEQUENCE: 42
attggatata tgaacgctga                                              20

<210> SEQ ID NO 43
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA:Combined DNA/RNA Molecule: nucleotides 6 to
      15 are deoxyribonucleotides-other nucleotides are ribonucleotides
<220> FEATURE:
<221> NAME/KEY: misc_feature
<222> LOCATION: (1)..(20)
<223> OTHER INFORMATION: Phosphorothioate internucleotide linkages
<220> FEATURE:
<221> NAME/KEY: modified_base
<222> LOCATION: (1)..(5)
<223> OTHER INFORMATION: 2'-O,4'-C-ethylene-linked bicyclic
      ribonucleotide
<220> FEATURE:
<221> NAME/KEY: modified_base
<222> LOCATION: (16)..(20)
<223> OTHER INFORMATION: 2'-O,4'-C-ethylene-linked bicyclic
      ribonucleotide

<400> SEQUENCE: 43
gcattggata tatgaacgct                                              20

<210> SEQ ID NO 44
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA:Combined DNA/RNA Molecule: nucleotides 6 to
      15 are deoxyribonucleotides-other nucleotides are ribonucleotides
<220> FEATURE:
<221> NAME/KEY: misc_feature
<222> LOCATION: (1)..(20)
<223> OTHER INFORMATION: Phosphorothioate internucleotide linkages
<220> FEATURE:
<221> NAME/KEY: modified_base
<222> LOCATION: (1)..(5)
<223> OTHER INFORMATION: 2'-O,4'-C-ethylene-linked bicyclic
      ribonucleotide
<220> FEATURE:
<221> NAME/KEY: modified_base
<222> LOCATION: (16)..(20)
<223> OTHER INFORMATION: 2'-O,4'-C-ethylene-linked bicyclic
      ribonucleotide
```

```
<400> SEQUENCE: 44
cggcattgga tatatgaacg                                            20

<210> SEQ ID NO 45
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA: any nucleotides may be ribonucleotides

<400> SEQUENCE: 45
atatatgaac gctgattcct                                            20

<210> SEQ ID NO 46
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA: any nucleotides may be ribonucleotides

<400> SEQUENCE: 46
acgctgattc ctttaatgat                                            20

<210> SEQ ID NO 47
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA: any nucleotides may be ribonucleotides

<400> SEQUENCE: 47
gaacgctgat tcctttaatg                                            20

<210> SEQ ID NO 48
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA: any nucleotides may be ribonucleotides

<400> SEQUENCE: 48
atgaacgctg attcctttaa                                            20

<210> SEQ ID NO 49
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA: any nucleotides may be ribonucleotides

<400> SEQUENCE: 49
atatgaacgc tgattccttt                                            20

<210> SEQ ID NO 50
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA: any nucleotides may be ribonucleotides
```

<400> SEQUENCE: 50
ggatatatga acgctgattc                                           20

<210> SEQ ID NO 51
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA: any nucleotides may be ribonucleotidess

<400> SEQUENCE: 51
ttggatatat gaacgctgat                                           20

<210> SEQ ID NO 52
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA: any nucleotides may be ribonucleotides

<400> SEQUENCE: 52
cattggatat atgaacgctg                                           20

<210> SEQ ID NO 53
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA: any nucleotides may be ribonucleotides

<400> SEQUENCE: 53
ggcattggat atatgaacgc                                           20

<210> SEQ ID NO 54
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA: any nucleotides may be ribonucleotides

<400> SEQUENCE: 54
gatatatgaa cgctgattcc                                           20

<210> SEQ ID NO 55
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA: any nucleotides may be ribonucleotides

<400> SEQUENCE: 55
cgctgattcc tttaatgatc                                           20

<210> SEQ ID NO 56
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA: any nucleotides may be ribonucleotides

<400> SEQUENCE: 56
aacgctgatt cctttaatga                                              20

<210> SEQ ID NO 57
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA: any nucleotides may be ribonucleotides

<400> SEQUENCE: 57
tgaacgctga ttcctttaat                                              20

<210> SEQ ID NO 58
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA: any nucleotides may be ribonucleotides

<400> SEQUENCE: 58
tatgaacgct gattccttta                                              20

<210> SEQ ID NO 59
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA: any nucleotides may be ribonucleotides

<400> SEQUENCE: 59
tatatgaacg ctgattcctt                                              20

<210> SEQ ID NO 60
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA: any nucleotides may be ribonucleotides

<400> SEQUENCE: 60
tggatatatg aacgctgatt                                              20

<210> SEQ ID NO 61
<211> LENGTH: 20
<212> TYPE: DNA
<213> ORGANISM: Artificial Sequence
<220> FEATURE:
<223> OTHER INFORMATION: Synthetic Sequence - antisense oligonucleotide
       targeting TDP-43 mRNA: any nucleotides may be ribonucleotides

<400> SEQUENCE: 61
attggatata tgaacgctga                                              20

<210> SEQ ID NO 62
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA: any nucleotides may be ribonucleotides

<400> SEQUENCE: 62
gcattggata tatgaacgct                                              20

<210> SEQ ID NO 63
<211> LENGTH: 20
<212> TYPE: DNA
<213> ORGANISM: Artificial Sequence
<220> FEATURE:
<223> OTHER INFORMATION: Synthetic Sequence - antisense oligonucleotide
      targeting TDP-43 mRNA:  any nucleotides may be ribonucleotides

<400> SEQUENCE: 63
cggcattgga tatatgaacg                                              20

<210> SEQ ID NO 64
<211> LENGTH: 42
<212> TYPE: RNA
<213> ORGANISM: Homo sapiens

<400> SEQUENCE: 64
aaaggagaga gcgcgugcag agacuuggug gugcauaaug ga                     42

<210> SEQ ID NO 65
<211> LENGTH: 34
<212> TYPE: RNA
<213> ORGANISM: Homo sapiens

<400> SEQUENCE: 65
gagcuugugg ugugcuuugc aggaggacuu gaag                              34

<210> SEQ ID NO 66
<211> LENGTH: 20
<212> TYPE: RNA
<213> ORGANISM: Artificial Sequence
<220> FEATURE:
<223> OTHER INFORMATION: Synthetic Sequence - antisense oligonucleotide
      targeting TDP-43 mRNA
<220> FEATURE:
<221> NAME/KEY: modified_base
<222> LOCATION: (1)..(2)
<223> OTHER INFORMATION: 2'-O,4'-C-ethylene-linked bicyclic
      ribonucleotide
<220> FEATURE:
<221> NAME/KEY: modified_base
<222> LOCATION: (2)..(2)
<223> OTHER INFORMATION: t
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (4)..(4)
<223> OTHER INFORMATION: 2'-O,4'-C-ethylene-linked bicyclic
      ribonucleotide
<220> FEATURE:
<221> NAME/KEY: modified_base
<222> LOCATION: (5)..(5)
<223> OTHER INFORMATION: 2'-O-methyladenosine
<220> FEATURE:
<221> NAME/KEY: modified_base
<222> LOCATION: (6)..(6)
<223> OTHER INFORMATION: 2'-O,4'-C-ethylene-linked bicyclic
      ribonucleotide
<220> FEATURE:
<221> NAME/KEY: modified_base
<222> LOCATION: (7)..(7)
<223> OTHER INFORMATION: gm
<220> FEATURE:
<221> NAME/KEY: modified_base
<222> LOCATION: (8)..(8)
<223> OTHER INFORMATION: 2'-O,4'-C-ethylene-linked bicyclic
      ribonucleotide

```
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (10)..(20)
<223> OTHER INFORMATION: 2'-O,4'-C-ethylene-linked bicyclic
      ribonucleotide
<220> FEATURE:
<221> NAME/KEY: modified_base
<222> LOCATION: (11)..(11)
<223> OTHER INFORMATION: t
<220> FEATURE:
<221> NAME/KEY: modified_base
<222> LOCATION: (13)..(13)
<223> OTHER INFORMATION: t
<220> FEATURE:
<221> NAME/KEY: modified_base
<222> LOCATION: (15)..(15)
<223> OTHER INFORMATION: t
<220> FEATURE:
<221> NAME/KEY: modified_base
<222> LOCATION: (18)..(20)
<223> OTHER INFORMATION: t

<400> SEQUENCE: 66
cugcacgcgc ucucuccuuu                                            20

<210> SEQ ID NO 67
<211> LENGTH: 20
<212> TYPE: RNA
<213> ORGANISM: Artificial Sequence
<220> FEATURE:
<223> OTHER INFORMATION: Synthetic Sequence - antisense oligonucleotide
      targeting TDP-43 mRNA
<220> FEATURE:
<221> NAME/KEY: modified_base
<222> LOCATION: (1)..(4)
<223> OTHER INFORMATION: 2'-O,4'-C-ethylene-linked bicyclic
      ribonucleotide
<220> FEATURE:
<221> NAME/KEY: modified_base
<222> LOCATION: (2)..(2)
<223> OTHER INFORMATION: t
<220> FEATURE:
<221> NAME/KEY: modified_base
<222> LOCATION: (4)..(4)
<223> OTHER INFORMATION: t
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (6)..(6)
<223> OTHER INFORMATION: 2'-O,4'-C-ethylene-linked bicyclic
      ribonucleotide
<220> FEATURE:
<221> NAME/KEY: modified_base
<222> LOCATION: (7)..(7)
<223> OTHER INFORMATION: 2'-O-methyladenosine
<220> FEATURE:
<221> NAME/KEY: modified_base
<222> LOCATION: (8)..(8)
<223> OTHER INFORMATION: 2'-O,4'-C-ethylene-linked bicyclic
      ribonucleotide
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (10)..(10)
<223> OTHER INFORMATION: 2'-O,4'-C-ethylene-linked bicyclic
      ribonucleotide
<220> FEATURE:
```

-continued

```
<221> NAME/KEY: modified_base
<222> LOCATION: (11)..(11)
<223> OTHER INFORMATION: gm
<220> FEATURE:
<221> NAME/KEY: modified_base
<222> LOCATION: (12)..(20)
<223> OTHER INFORMATION: 2'-O,4'-C-ethylene-linked bicyclic
      ribonucleotide
<220> FEATURE:
<221> NAME/KEY: modified_base
<222> LOCATION: (13)..(13)
<223> OTHER INFORMATION: t
<220> FEATURE:
<221> NAME/KEY: modified_base
<222> LOCATION: (15)..(15)
<223> OTHER INFORMATION: t
<220> FEATURE:
<221> NAME/KEY: modified_base
<222> LOCATION: (17)..(17)
<223> OTHER INFORMATION: t
<220> FEATURE:
<221> NAME/KEY: modified_base
<222> LOCATION: (20)..(20)
<223> OTHER INFORMATION: t

<400> SEQUENCE: 67
cucugcacgc gcucucuccu                                                     20

<210> SEQ ID NO 68
<211> LENGTH: 20
<212> TYPE: RNA
<213> ORGANISM: Artificial Sequence
<220> FEATURE:
<223> OTHER INFORMATION: Synthetic Sequence - antisense oligonucleotide
      targeting TDP-43 mRNA
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (2)..(6)
<223> OTHER INFORMATION: 2'-O,4'-C-ethylene-linked bicyclic
      ribonucleotide
<220> FEATURE:
<221> NAME/KEY: modified_base
<222> LOCATION: (2)..(2)
<223> OTHER INFORMATION: t
<220> FEATURE:
<221> NAME/KEY: modified_base
<222> LOCATION: (4)..(4)
<223> OTHER INFORMATION: t
<220> FEATURE:
<221> NAME/KEY: modified_base
<222> LOCATION: (6)..(6)
<223> OTHER INFORMATION: t
<220> FEATURE:
<221> NAME/KEY: modified_base
<222> LOCATION: (7)..(7)
<223> OTHER INFORMATION: gm
<220> FEATURE:
<221> NAME/KEY: modified_base
<222> LOCATION: (8)..(8)
<223> OTHER INFORMATION: 2'-O,4'-C-ethylene-linked bicyclic
      ribonucleotide
<220> FEATURE:
<221> NAME/KEY: modified_base
<222> LOCATION: (9)..(9)
<223> OTHER INFORMATION: 2'-O-methyladenosine
<220> FEATURE:
<221> NAME/KEY: modified_base
<222> LOCATION: (10)..(10)
<223> OTHER INFORMATION: 2'-O,4'-C-ethylene-linked bicyclic
      ribonucleotide
<220> FEATURE:
<221> NAME/KEY: modified_base
<222> LOCATION: (11)..(11)
```

<223> OTHER INFORMATION: gm
<220> FEATURE:
<221> NAME/KEY: modified_base
<222> LOCATION: (12)..(12)
<223> OTHER INFORMATION: 2'-O,4'-C-ethylene-linked bicyclic
      ribonucleotide
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (14)..(20)
<223> OTHER INFORMATION: 2'-O,4'-C-ethylene-linked bicyclic
      ribonucleotide
<220> FEATURE:
<221> NAME/KEY: modified_base
<222> LOCATION: (15)..(15)
<223> OTHER INFORMATION: t
<220> FEATURE:
<221> NAME/KEY: modified_base
<222> LOCATION: (17)..(17)
<223> OTHER INFORMATION: t
<220> FEATURE:
<221> NAME/KEY: modified_base
<222> LOCATION: (19)..(19)
<223> OTHER INFORMATION: t

<400> SEQUENCE: 68
gucucugcac gcgcucucuc                                                    20

<210> SEQ ID NO 69
<211> LENGTH: 20
<212> TYPE: RNA
<213> ORGANISM: Artificial Sequence
<220> FEATURE:
<223> OTHER INFORMATION: Synthetic Sequence - antisense oligonucleotide
      targeting TDP-43 mRNA
<220> FEATURE:
<221> NAME/KEY: modified_base
<222> LOCATION: (1)..(2)
<223> OTHER INFORMATION: 2'-O-methyladenosine
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (4)..(8)
<223> OTHER INFORMATION: 2'-O,4'-C-ethylene-linked bicyclic
      ribonucleotide
<220> FEATURE:
<221> NAME/KEY: modified_base
<222> LOCATION: (4)..(4)
<223> OTHER INFORMATION: t
<220> FEATURE:
<221> NAME/KEY: modified_base
<222> LOCATION: (6)..(6)
<223> OTHER INFORMATION: t
<220> FEATURE:
<221> NAME/KEY: modified_base
<222> LOCATION: (8)..(8)
<223> OTHER INFORMATION: t
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (10)..(10)
<223> OTHER INFORMATION: 2'-O,4'-C-ethylene-linked bicyclic
      ribonucleotide
<220> FEATURE:
<221> NAME/KEY: modified_base
<222> LOCATION: (11)..(11)
<223> OTHER INFORMATION: 2'-O-methyladenosine
<220> FEATURE:

```
<221> NAME/KEY: modified_base
<222> LOCATION: (12)..(12)
<223> OTHER INFORMATION: 2'-O,4'-C-ethylene-linked bicyclic
      ribonucleotide
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (14)..(14)
<223> OTHER INFORMATION: 2'-O,4'-C-ethylene-linked bicyclic
      ribonucleotide
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (16)..(20)
<223> OTHER INFORMATION: 2'-O,4'-C-ethylene-linked bicyclic
      ribonucleotide
<220> FEATURE:
<221> NAME/KEY: modified_base
<222> LOCATION: (17)..(17)
<223> OTHER INFORMATION: t
<220> FEATURE:
<221> NAME/KEY: modified_base
<222> LOCATION: (19)..(19)
<223> OTHER INFORMATION: t

<400> SEQUENCE: 69
aagucucugc acgcgcucuc                                              20

<210> SEQ ID NO 70
<211> LENGTH: 20
<212> TYPE: RNA
<213> ORGANISM: Artificial Sequence
<220> FEATURE:
<223> OTHER INFORMATION: Synthetic Sequence - antisense oligonucleotide
      targeting TDP-43 mRNA
<220> FEATURE:
<221> NAME/KEY: modified_base
<222> LOCATION: (1)..(2)
<223> OTHER INFORMATION: 2'-O,4'-C-ethylene-linked bicyclic
      ribonucleotide
<220> FEATURE:
<221> NAME/KEY: modified_base
<222> LOCATION: (3)..(4)
<223> OTHER INFORMATION: 2'-O-methyladenosine
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (6)..(10)
<223> OTHER INFORMATION: 2'-O,4'-C-ethylene-linked bicyclic
      ribonucleotide
<220> FEATURE:
<221> NAME/KEY: modified_base
<222> LOCATION: (6)..(6)
<223> OTHER INFORMATION: t
<220> FEATURE:
<221> NAME/KEY: modified_base
<222> LOCATION: (8)..(8)
<223> OTHER INFORMATION: t
<220> FEATURE:
<221> NAME/KEY: modified_base
<222> LOCATION: (10)..(10)
<223> OTHER INFORMATION: t
<220> FEATURE:
<221> NAME/KEY: modified_base
<222> LOCATION: (11)..(11)
<223> OTHER INFORMATION: gm
<220> FEATURE:
<221> NAME/KEY: modified_base
```

<222> LOCATION: (12)..(12)
<223> OTHER INFORMATION: 2'-O,4'-C-ethylene-linked bicyclic
      ribonucleotide
<220> FEATURE:
<221> NAME/KEY: modified_base
<222> LOCATION: (13)..(13)
<223> OTHER INFORMATION: 2'-O-methyladenosine
<220> FEATURE:
<221> NAME/KEY: modified_base
<222> LOCATION: (14)..(14)
<223> OTHER INFORMATION: 2'-O,4'-C-ethylene-linked bicyclic
      ribonucleotide
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (16)..(16)
<223> OTHER INFORMATION: 2'-O,4'-C-ethylene-linked bicyclic
      ribonucleotide
<220> FEATURE:
<221> NAME/KEY: modified_base
<222> LOCATION: (17)..(17)
<223> OTHER INFORMATION: gm
<220> FEATURE:
<221> NAME/KEY: modified_base
<222> LOCATION: (18)..(20)
<223> OTHER INFORMATION: 2'-O,4'-C-ethylene-linked bicyclic
      ribonucleotide
<220> FEATURE:
<221> NAME/KEY: modified_base
<222> LOCATION: (19)..(19)
<223> OTHER INFORMATION: t

<400> SEQUENCE: 70
ccaagucucu gcacgcgcuc                                                20

<210> SEQ ID NO 71
<211> LENGTH: 20
<212> TYPE: RNA
<213> ORGANISM: Artificial Sequence
<220> FEATURE:
<223> OTHER INFORMATION: Synthetic Sequence - antisense oligonucleotide
      targeting TDP-43 mRNA
<220> FEATURE:
<221> NAME/KEY: modified_base
<222> LOCATION: (1)..(1)
<223> OTHER INFORMATION: 2'-O,4'-C-ethylene-linked bicyclic
      ribonucleotide
<220> FEATURE:
<221> NAME/KEY: modified_base
<222> LOCATION: (2)..(2)
<223> OTHER INFORMATION: 2'-O-methyladenosine
<220> FEATURE:
<221> NAME/KEY: modified_base
<222> LOCATION: (3)..(4)
<223> OTHER INFORMATION: 2'-O,4'-C-ethylene-linked bicyclic
      ribonucleotide
<220> FEATURE:
<221> NAME/KEY: modified_base
<222> LOCATION: (5)..(6)
<223> OTHER INFORMATION: 2'-O-methyladenosine
<220> FEATURE:
<221> NAME/KEY: modified_base
<222> LOCATION: (7)..(7)
<223> OTHER INFORMATION: gm
<220> FEATURE:
<221> NAME/KEY: modified_base
<222> LOCATION: (8)..(12)
<223> OTHER INFORMATION: 2'-O,4'-C-ethylene-linked bicyclic
      ribonucleotide
<220> FEATURE:
<221> NAME/KEY: modified_base
<222> LOCATION: (8)..(8)
<223> OTHER INFORMATION: t
<220> FEATURE:

```
<221> NAME/KEY: modified_base
<222> LOCATION: (10)..(10)
<223> OTHER INFORMATION: t
<220> FEATURE:
<221> NAME/KEY: modified_base
<222> LOCATION: (12)..(12)
<223> OTHER INFORMATION: t
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (14)..(14)
<223> OTHER INFORMATION: 2'-O,4'-C-ethylene-linked bicyclic
      ribonucleotide
<220> FEATURE:
<221> NAME/KEY: modified_base
<222> LOCATION: (15)..(15)
<223> OTHER INFORMATION: 2'-O-methyladenosine
<220> FEATURE:
<221> NAME/KEY: modified_base
<222> LOCATION: (16)..(16)
<223> OTHER INFORMATION: 2'-O,4'-C-ethylene-linked bicyclic
      ribonucleotide
<220> FEATURE:
<221> NAME/KEY: modified_base
<222> LOCATION: (17)..(17)
<223> OTHER INFORMATION: gm
<220> FEATURE:
<221> NAME/KEY: modified_base
<222> LOCATION: (18)..(18)
<223> OTHER INFORMATION: 2'-O,4'-C-ethylene-linked bicyclic
      ribonucleotide
<220> FEATURE:
<221> NAME/KEY: modified_base
<222> LOCATION: (19)..(19)
<223> OTHER INFORMATION: gm
<220> FEATURE:
<221> NAME/KEY: modified_base
<222> LOCATION: (20)..(20)
<223> OTHER INFORMATION: 2'-O,4'-C-ethylene-linked bicyclic
      ribonucleotide

<400> SEQUENCE: 71
caccaagucu cugcacgcgc                                              20

<210> SEQ ID NO 72
<211> LENGTH: 20
<212> TYPE: RNA
<213> ORGANISM: Artificial Sequence
<220> FEATURE:
<223> OTHER INFORMATION: Synthetic Sequence - antisense oligonucleotide
      targeting TDP-43 mRNA
<220> FEATURE:
<221> NAME/KEY: modified_base
<222> LOCATION: (1)..(1)
<223> OTHER INFORMATION: 2'-O-methyladenosine
<220> FEATURE:
<221> NAME/KEY: modified_base
<222> LOCATION: (2)..(3)
<223> OTHER INFORMATION: 2'-O,4'-C-ethylene-linked bicyclic
      ribonucleotide
<220> FEATURE:
<221> NAME/KEY: modified_base
<222> LOCATION: (4)..(4)
<223> OTHER INFORMATION: 2'-O-methyladenosine
<220> FEATURE:
<221> NAME/KEY: modified_base
<222> LOCATION: (5)..(6)
<223> OTHER INFORMATION: 2'-O,4'-C-ethylene-linked bicyclic
      ribonucleotide
<220> FEATURE:
<221> NAME/KEY: modified_base
<222> LOCATION: (7)..(8)
<223> OTHER INFORMATION: 2'-O-methyladenosine
<220> FEATURE:
```

```
<221> NAME/KEY: modified_base
<222> LOCATION: (9)..(9)
<223> OTHER INFORMATION: gm
<220> FEATURE:
<221> NAME/KEY: modified_base
<222> LOCATION: (10)..(14)
<223> OTHER INFORMATION: 2'-O,4'-C-ethylene-linked bicyclic
      ribonucleotide
<220> FEATURE:
<221> NAME/KEY: modified_base
<222> LOCATION: (10)..(10)
<223> OTHER INFORMATION: t
<220> FEATURE:
<221> NAME/KEY: modified_base
<222> LOCATION: (12)..(12)
<223> OTHER INFORMATION: t
<220> FEATURE:
<221> NAME/KEY: modified_base
<222> LOCATION: (14)..(14)
<223> OTHER INFORMATION: t
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (16)..(16)
<223> OTHER INFORMATION: 2'-O,4'-C-ethylene-linked bicyclic
      ribonucleotide
<220> FEATURE:
<221> NAME/KEY: modified_base
<222> LOCATION: (17)..(17)
<223> OTHER INFORMATION: 2'-O-methyladenosine
<220> FEATURE:
<221> NAME/KEY: modified_base
<222> LOCATION: (18)..(18)
<223> OTHER INFORMATION: 2'-O,4'-C-ethylene-linked bicyclic
      ribonucleotide
<220> FEATURE:
<221> NAME/KEY: modified_base
<222> LOCATION: (19)..(19)
<223> OTHER INFORMATION: gm
<220> FEATURE:
<221> NAME/KEY: modified_base
<222> LOCATION: (20)..(20)
<223> OTHER INFORMATION: 2'-O,4'-C-ethylene-linked bicyclic
      ribonucleotide

<400> SEQUENCE: 72
accaccaagu cucugcacgc                                           20

<210> SEQ ID NO 73
<211> LENGTH: 20
<212> TYPE: RNA
<213> ORGANISM: Artificial Sequence
<220> FEATURE:
<223> OTHER INFORMATION: Synthetic Sequence - antisense oligonucleotide
      targeting TDP-43 mRNA
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (2)..(2)
<223> OTHER INFORMATION: 2'-O,4'-C-ethylene-linked bicyclic
      ribonucleotide
<220> FEATURE:
<221> NAME/KEY: modified_base
<222> LOCATION: (3)..(3)
<223> OTHER INFORMATION: 2'-O-methyladenosine
<220> FEATURE:
<221> NAME/KEY: modified_base
<222> LOCATION: (4)..(5)
<223> OTHER INFORMATION: 2'-O,4'-C-ethylene-linked bicyclic
      ribonucleotide
<220> FEATURE:
```

```
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (7)..(8)
<223> OTHER INFORMATION: 2'-O,4'-C-ethylene-linked bicyclic
      ribonucleotide
<220> FEATURE:
<221> NAME/KEY: modified_base
<222> LOCATION: (9)..(10)
<223> OTHER INFORMATION: 2'-O-methyladenosine
<220> FEATURE:
<221> NAME/KEY: modified_base
<222> LOCATION: (11)..(11)
<223> OTHER INFORMATION: gm
<220> FEATURE:
<221> NAME/KEY: modified_base
<222> LOCATION: (12)..(16)
<223> OTHER INFORMATION: 2'-O,4'-C-ethylene-linked bicyclic
      ribonucleotide
<220> FEATURE:
<221> NAME/KEY: modified_base
<222> LOCATION: (12)..(12)
<223> OTHER INFORMATION: t
<220> FEATURE:
<221> NAME/KEY: modified_base
<222> LOCATION: (14)..(14)
<223> OTHER INFORMATION: t
<220> FEATURE:
<221> NAME/KEY: modified_base
<222> LOCATION: (16)..(16)
<223> OTHER INFORMATION: t
<220> FEATURE:
<221> NAME/KEY: modified_base
<222> LOCATION: (17)..(17)
<223> OTHER INFORMATION: gm
<220> FEATURE:
<221> NAME/KEY: modified_base
<222> LOCATION: (18)..(18)
<223> OTHER INFORMATION: 2'-O,4'-C-ethylene-linked bicyclic
      ribonucleotide
<220> FEATURE:
<221> NAME/KEY: modified_base
<222> LOCATION: (19)..(19)
<223> OTHER INFORMATION: 2'-O-methyladenosine
<220> FEATURE:
<221> NAME/KEY: modified_base
<222> LOCATION: (20)..(20)
<223> OTHER INFORMATION: 2'-O,4'-C-ethylene-linked bicyclic
      ribonucleotide

<400> SEQUENCE: 73
gcaccaccaa gucucugcac                                                   20

<210> SEQ ID NO 74
<211> LENGTH: 20
<212> TYPE: RNA
<213> ORGANISM: Artificial Sequence
<220> FEATURE:
<223> OTHER INFORMATION: Synthetic Sequence - antisense oligonucleotide
      targeting TDP-43 mRNA
<220> FEATURE:
<221> NAME/KEY: modified_base
<222> LOCATION: (1)..(1)
<223> OTHER INFORMATION: 2'-O-methyladenosine
<220> FEATURE:
<221> NAME/KEY: modified_base
<222> LOCATION: (2)..(2)
<223> OTHER INFORMATION: 2'-O,4'-C-ethylene-linked bicyclic
      ribonucleotide
<220> FEATURE:
<221> NAME/KEY: modified_base
<222> LOCATION: (2)..(2)
<223> OTHER INFORMATION: t
<220> FEATURE:
<221> NAME/KEY: modified_base
```

```
<222> LOCATION: (3)..(3)
<223> OTHER INFORMATION: gm
<220> FEATURE:
<221> NAME/KEY: modified_base
<222> LOCATION: (4)..(4)
<223> OTHER INFORMATION: 2'-O,4'-C-ethylene-linked bicyclic
      ribonucleotide
<220> FEATURE:
<221> NAME/KEY: modified_base
<222> LOCATION: (5)..(5)
<223> OTHER INFORMATION: 2'-O-methyladenosine
<220> FEATURE:
<221> NAME/KEY: modified_base
<222> LOCATION: (6)..(7)
<223> OTHER INFORMATION: 2'-O,4'-C-ethylene-linked bicyclic
      ribonucleotide
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (9)..(10)
<223> OTHER INFORMATION: 2'-O,4'-C-ethylene-linked bicyclic
      ribonucleotide
<220> FEATURE:
<221> NAME/KEY: modified_base
<222> LOCATION: (11)..(12)
<223> OTHER INFORMATION: 2'-O-methyladenosine
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (14)..(18)
<223> OTHER INFORMATION: 2'-O,4'-C-ethylene-linked bicyclic
      ribonucleotide
<220> FEATURE:
<221> NAME/KEY: modified_base
<222> LOCATION: (14)..(14)
<223> OTHER INFORMATION: t
<220> FEATURE:
<221> NAME/KEY: modified_base
<222> LOCATION: (16)..(16)
<223> OTHER INFORMATION: t
<220> FEATURE:
<221> NAME/KEY: modified_base
<222> LOCATION: (18)..(18)
<223> OTHER INFORMATION: t
<220> FEATURE:
<221> NAME/KEY: modified_base
<222> LOCATION: (19)..(19)
<223> OTHER INFORMATION: gm
<220> FEATURE:
<221> NAME/KEY: modified_base
<222> LOCATION: (20)..(20)
<223> OTHER INFORMATION: 2'-O,4'-C-ethylene-linked bicyclic
      ribonucleotide

<400> SEQUENCE: 74
augcaccacc aagucucugc                                              20

<210> SEQ ID NO 75
<211> LENGTH: 20
<212> TYPE: RNA
<213> ORGANISM: Artificial Sequence
<220> FEATURE:
<223> OTHER INFORMATION: Synthetic Sequence - antisense oligonucleotide
      targeting TDP-43 mRNA
<220> FEATURE:
<221> NAME/KEY: modified_base
<222> LOCATION: (1)..(2)
<223> OTHER INFORMATION: 2'-O,4'-C-ethylene-linked bicyclic
      ribonucleotide
<220> FEATURE:
<221> NAME/KEY: modified_base
```

```
<222> LOCATION: (1)..(2)
<223> OTHER INFORMATION: t
<220> FEATURE:
<221> NAME/KEY: modified_base
<222> LOCATION: (3)..(3)
<223> OTHER INFORMATION: 2'-O-methyladenosine
<220> FEATURE:
<221> NAME/KEY: modified_base
<222> LOCATION: (4)..(4)
<223> OTHER INFORMATION: 2'-O,4'-C-ethylene-linked bicyclic
      ribonucleotide
<220> FEATURE:
<221> NAME/KEY: modified_base
<222> LOCATION: (4)..(4)
<223> OTHER INFORMATION: t
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (6)..(6)
<223> OTHER INFORMATION: 2'-O,4'-C-ethylene-linked bicyclic
      ribonucleotide
<220> FEATURE:
<221> NAME/KEY: modified_base
<222> LOCATION: (7)..(7)
<223> OTHER INFORMATION: 2'-O-methyladenosine
<220> FEATURE:
<221> NAME/KEY: modified_base
<222> LOCATION: (8)..(9)
<223> OTHER INFORMATION: 2'-O,4'-C-ethylene-linked bicyclic
      ribonucleotide
<220> FEATURE:
<221> NAME/KEY: modified_base
<222> LOCATION: (10)..(10)
<223> OTHER INFORMATION: 2'-O-methyladenosine
<220> FEATURE:
<221> NAME/KEY: modified_base
<222> LOCATION: (11)..(12)
<223> OTHER INFORMATION: 2'-O,4'-C-ethylene-linked bicyclic
      ribonucleotide
<220> FEATURE:
<221> NAME/KEY: modified_base
<222> LOCATION: (13)..(14)
<223> OTHER INFORMATION: 2'-O-methyladenosine
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (16)..(20)
<223> OTHER INFORMATION: 2'-O,4'-C-ethylene-linked bicyclic
      ribonucleotide
<220> FEATURE:
<221> NAME/KEY: modified_base
<222> LOCATION: (16)..(16)
<223> OTHER INFORMATION: t
<220> FEATURE:
<221> NAME/KEY: modified_base
<222> LOCATION: (18)..(18)
<223> OTHER INFORMATION: t
<220> FEATURE:
<221> NAME/KEY: modified_base
<222> LOCATION: (20)..(20)
<223> OTHER INFORMATION: t

<400> SEQUENCE: 75
uuaugcacca ccaagucucu                                                   20

<210> SEQ ID NO 76
<211> LENGTH: 20
<212> TYPE: RNA
<213> ORGANISM: Artificial Sequence
<220> FEATURE:
<223> OTHER INFORMATION: Synthetic Sequence - antisense oligonucleotide
``` targeting TDP-43 mRNA
<220> FEATURE:
<221> NAME/KEY: modified_base
<222> LOCATION: (1)..(1)
<223> OTHER INFORMATION: 2'-O,4'-C-ethylene-linked bicyclic
      ribonucleotide
<220> FEATURE:
<221> NAME/KEY: modified_base
<222> LOCATION: (2)..(2)
<223> OTHER INFORMATION: 2'-O-methyladenosine
<220> FEATURE:
<221> NAME/KEY: modified_base
<222> LOCATION: (3)..(4)
<223> OTHER INFORMATION: 2'-O,4'-C-ethylene-linked bicyclic
      ribonucleotide
<220> FEATURE:
<221> NAME/KEY: modified_base
<222> LOCATION: (3)..(4)
<223> OTHER INFORMATION: t
<220> FEATURE:
<221> NAME/KEY: modified_base
<222> LOCATION: (5)..(5)
<223> OTHER INFORMATION: 2'-O-methyladenosine
<220> FEATURE:
<221> NAME/KEY: modified_base
<222> LOCATION: (6)..(6)
<223> OTHER INFORMATION: 2'-O,4'-C-ethylene-linked bicyclic
      ribonucleotide
<220> FEATURE:
<221> NAME/KEY: modified_base
<222> LOCATION: (6)..(6)
<223> OTHER INFORMATION: t
<220> FEATURE:
<221> NAME/KEY: modified_base
<222> LOCATION: (7)..(7)
<223> OTHER INFORMATION: gm
<220> FEATURE:
<221> NAME/KEY: modified_base
<222> LOCATION: (8)..(8)
<223> OTHER INFORMATION: 2'-O,4'-C-ethylene-linked bicyclic
      ribonucleotide
<220> FEATURE:
<221> NAME/KEY: modified_base
<222> LOCATION: (9)..(9)
<223> OTHER INFORMATION: 2'-O-methyladenosine
<220> FEATURE:
<221> NAME/KEY: modified_base
<222> LOCATION: (10)..(11)
<223> OTHER INFORMATION: 2'-O,4'-C-ethylene-linked bicyclic
      ribonucleotide
<220> FEATURE:
<221> NAME/KEY: modified_base
<222> LOCATION: (12)..(12)
<223> OTHER INFORMATION: 2'-O-methyladenosine
<220> FEATURE:
<221> NAME/KEY: modified_base
<222> LOCATION: (13)..(14)
<223> OTHER INFORMATION: 2'-O,4'-C-ethylene-linked bicyclic
      ribonucleotide
<220> FEATURE:
<221> NAME/KEY: modified_base
<222> LOCATION: (15)..(16)
<223> OTHER INFORMATION: 2'-O-methyladenosine
<220> FEATURE:
<221> NAME/KEY: modified_base
<222> LOCATION: (17)..(17)
<223> OTHER INFORMATION: gm
<220> FEATURE:
<221> NAME/KEY: modified_base
<222> LOCATION: (18)..(20)
<223> OTHER INFORMATION: 2'-O,4'-C-ethylene-linked bicyclic
      ribonucleotide
<220> FEATURE:
<221> NAME/KEY: modified_base
<222> LOCATION: (18)..(18)
<223> OTHER INFORMATION: t
<220> FEATURE:
<221> NAME/KEY: modified_base
<222> LOCATION: (20)..(20)

-continued

```
<223> OTHER INFORMATION: t

<400> SEQUENCE: 76
cauuaugcac caccaagucu                                           20

<210> SEQ ID NO 77
<211> LENGTH: 20
<212> TYPE: RNA
<213> ORGANISM: Artificial Sequence
<220> FEATURE:
<223> OTHER INFORMATION: Synthetic Sequence - antisense oligonucleotide
      targeting TDP-43 mRNA
<220> FEATURE:
<221> NAME/KEY: modified_base
<222> LOCATION: (1)..(3)
<223> OTHER INFORMATION: 2'-O,4'-C-ethylene-linked bicyclic
      ribonucleotide
<220> FEATURE:
<221> NAME/KEY: modified_base
<222> LOCATION: (1)..(1)
<223> OTHER INFORMATION: t
<220> FEATURE:
<221> NAME/KEY: modified_base
<222> LOCATION: (4)..(4)
<223> OTHER INFORMATION: 2'-O-methyladenosine
<220> FEATURE:
<221> NAME/KEY: modified_base
<222> LOCATION: (5)..(6)
<223> OTHER INFORMATION: 2'-O,4'-C-ethylene-linked bicyclic
      ribonucleotide
<220> FEATURE:
<221> NAME/KEY: modified_base
<222> LOCATION: (5)..(6)
<223> OTHER INFORMATION: t
<220> FEATURE:
<221> NAME/KEY: modified_base
<222> LOCATION: (7)..(7)
<223> OTHER INFORMATION: 2'-O-methyladenosine
<220> FEATURE:
<221> NAME/KEY: modified_base
<222> LOCATION: (8)..(8)
<223> OTHER INFORMATION: 2'-O,4'-C-ethylene-linked bicyclic
      ribonucleotide
<220> FEATURE:
<221> NAME/KEY: modified_base
<222> LOCATION: (8)..(8)
<223> OTHER INFORMATION: t
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (10)..(10)
<223> OTHER INFORMATION: 2'-O,4'-C-ethylene-linked bicyclic
      ribonucleotide
<220> FEATURE:
<221> NAME/KEY: modified_base
<222> LOCATION: (11)..(11)
<223> OTHER INFORMATION: 2'-O-methyladenosine
<220> FEATURE:
<221> NAME/KEY: modified_base
<222> LOCATION: (12)..(13)
<223> OTHER INFORMATION: 2'-O,4'-C-ethylene-linked bicyclic
      ribonucleotide
<220> FEATURE:
<221> NAME/KEY: modified_base
<222> LOCATION: (14)..(14)
<223> OTHER INFORMATION: 2'-O-methyladenosine
<220> FEATURE:
<221> NAME/KEY: modified_base
<222> LOCATION: (15)..(16)
<223> OTHER INFORMATION: 2'-O,4'-C-ethylene-linked bicyclic
      ribonucleotide
<220> FEATURE:
<221> NAME/KEY: modified_base
<222> LOCATION: (17)..(18)
```

```
<223> OTHER INFORMATION: 2'-O-methyladenosine
<220> FEATURE:
<221> NAME/KEY: modified_base
<222> LOCATION: (19)..(19)
<223> OTHER INFORMATION: gm
<220> FEATURE:
<221> NAME/KEY: modified_base
<222> LOCATION: (20)..(20)
<223> OTHER INFORMATION: 2'-O,4'-C-ethylene-linked bicyclic
      ribonucleotide
<220> FEATURE:
<221> NAME/KEY: modified_base
<222> LOCATION: (20)..(20)
<223> OTHER INFORMATION: t

<400> SEQUENCE: 77
uccauuaugc accaccaagu                                              20

<210> SEQ ID NO 78
<211> LENGTH: 20
<212> TYPE: RNA
<213> ORGANISM: Artificial Sequence
<220> FEATURE:
<223> OTHER INFORMATION: Synthetic Sequence - antisense oligonucleotide
      targeting TDP-43 mRNA
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (2)..(2)
<223> OTHER INFORMATION: 2'-O,4'-C-ethylene-linked bicyclic
      ribonucleotide
<220> FEATURE:
<221> NAME/KEY: modified_base
<222> LOCATION: (3)..(5)
<223> OTHER INFORMATION: 2'-O-methyladenosine
<220> FEATURE:
<221> NAME/KEY: modified_base
<222> LOCATION: (6)..(6)
<223> OTHER INFORMATION: gm
<220> FEATURE:
<221> NAME/KEY: modified_base
<222> LOCATION: (7)..(7)
<223> OTHER INFORMATION: 2'-O,4'-C-ethylene-linked bicyclic
      ribonucleotide
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (9)..(9)
<223> OTHER INFORMATION: 2'-O,4'-C-ethylene-linked bicyclic
      ribonucleotide
<220> FEATURE:
<221> NAME/KEY: modified_base
<222> LOCATION: (10)..(10)
<223> OTHER INFORMATION: 2'-O-methyladenosine
<220> FEATURE:
<221> NAME/KEY: modified_base
<222> LOCATION: (11)..(12)
<223> OTHER INFORMATION: 2'-O,4'-C-ethylene-linked bicyclic
      ribonucleotide
<220> FEATURE:
<221> NAME/KEY: modified_base
<222> LOCATION: (13)..(13)
<223> OTHER INFORMATION: 2'-O-methyladenosine
<220> FEATURE:
<221> NAME/KEY: modified_base
<222> LOCATION: (14)..(14)
<223> OTHER INFORMATION: 2'-O,4'-C-ethylene-linked bicyclic
      ribonucleotide
<220> FEATURE:
<221> NAME/KEY: modified_base
<222> LOCATION: (15)..(16)
```

<223> OTHER INFORMATION: 2'-O-methyladenosine
<220> FEATURE:
<221> NAME/KEY: modified_base
<222> LOCATION: (17)..(17)
<223> OTHER INFORMATION: gm
<220> FEATURE:
<221> NAME/KEY: modified_base
<222> LOCATION: (18)..(20)
<223> OTHER INFORMATION: 2'-O,4'-C-ethylene-linked bicyclic
    ribonucleotide
<220> FEATURE:
<221> NAME/KEY: modified_base
<222> LOCATION: (19)..(19)
<223> OTHER INFORMATION: t

<400> SEQUENCE: 78
gcaaagcaca ccacaagcuc                                                 20

<210> SEQ ID NO 79
<211> LENGTH: 20
<212> TYPE: RNA
<213> ORGANISM: Artificial Sequence
<220> FEATURE:
<223> OTHER INFORMATION: Synthetic Sequence - antisense oligonucleotide
    targeting TDP-43 mRNA
<220> FEATURE:
<221> NAME/KEY: modified_base
<222> LOCATION: (1)..(2)
<223> OTHER INFORMATION: 2'-O,4'-C-ethylene-linked bicyclic
    ribonucleotide
<220> FEATURE:
<221> NAME/KEY: modified_base
<222> LOCATION: (2)..(2)
<223> OTHER INFORMATION: t
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (4)..(4)
<223> OTHER INFORMATION: 2'-O,4'-C-ethylene-linked bicyclic
    ribonucleotide
<220> FEATURE:
<221> NAME/KEY: modified_base
<222> LOCATION: (5)..(7)
<223> OTHER INFORMATION: 2'-O-methyladenosine
<220> FEATURE:
<221> NAME/KEY: modified_base
<222> LOCATION: (8)..(8)
<223> OTHER INFORMATION: gm
<220> FEATURE:
<221> NAME/KEY: modified_base
<222> LOCATION: (9)..(9)
<223> OTHER INFORMATION: 2'-O,4'-C-ethylene-linked bicyclic
    ribonucleotide
<220> FEATURE:
<221> NAME/KEY: modified_base
<222> LOCATION: (10)..(10)
<223> OTHER INFORMATION: 2'-O-methyladenosine
<220> FEATURE:
<221> NAME/KEY: modified_base
<222> LOCATION: (11)..(11)
<223> OTHER INFORMATION: 2'-O,4'-C-ethylene-linked bicyclic
    ribonucleotide
<220> FEATURE:
<221> NAME/KEY: modified_base
<222> LOCATION: (12)..(12)
<223> OTHER INFORMATION: 2'-O-methyladenosine
<220> FEATURE:
<221> NAME/KEY: modified_base
<222> LOCATION: (13)..(14)
<223> OTHER INFORMATION: 2'-O,4'-C-ethylene-linked bicyclic
    ribonucleotide
<220> FEATURE:
<221> NAME/KEY: modified_base
<222> LOCATION: (15)..(15)

```
<223> OTHER INFORMATION: 2'-O-methyladenosine
<220> FEATURE:
<221> NAME/KEY: modified_base
<222> LOCATION: (16)..(16)
<223> OTHER INFORMATION: 2'-O,4'-C-ethylene-linked bicyclic
      ribonucleotide
<220> FEATURE:
<221> NAME/KEY: modified_base
<222> LOCATION: (17)..(18)
<223> OTHER INFORMATION: 2'-O-methyladenosine
<220> FEATURE:
<221> NAME/KEY: modified_base
<222> LOCATION: (19)..(19)
<223> OTHER INFORMATION: gm
<220> FEATURE:
<221> NAME/KEY: modified_base
<222> LOCATION: (20)..(20)
<223> OTHER INFORMATION: 2'-O,4'-C-ethylene-linked bicyclic
      ribonucleotide

<400> SEQUENCE: 79
cugcaaagca caccacaagc                                                   20

<210> SEQ ID NO 80
<211> LENGTH: 20
<212> TYPE: RNA
<213> ORGANISM: Artificial Sequence
<220> FEATURE:
<223> OTHER INFORMATION: Synthetic Sequence - antisense oligonucleotide
      targeting TDP-43 mRNA
<220> FEATURE:
<221> NAME/KEY: modified_base
<222> LOCATION: (1)..(4)
<223> OTHER INFORMATION: 2'-O,4'-C-ethylene-linked bicyclic
      ribonucleotide
<220> FEATURE:
<221> NAME/KEY: modified_base
<222> LOCATION: (1)..(1)
<223> OTHER INFORMATION: t
<220> FEATURE:
<221> NAME/KEY: modified_base
<222> LOCATION: (1)..(4)
<223> OTHER INFORMATION: t
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (6)..(6)
<223> OTHER INFORMATION: 2'-O,4'-C-ethylene-linked bicyclic
      ribonucleotide
<220> FEATURE:
<221> NAME/KEY: modified_base
<222> LOCATION: (7)..(9)
<223> OTHER INFORMATION: 2'-O-methyladenosine
<220> FEATURE:
<221> NAME/KEY: modified_base
<222> LOCATION: (10)..(10)
<223> OTHER INFORMATION: gm
<220> FEATURE:
<221> NAME/KEY: modified_base
<222> LOCATION: (11)..(11)
<223> OTHER INFORMATION: 2'-O,4'-C-ethylene-linked bicyclic
      ribonucleotide
<220> FEATURE:
<221> NAME/KEY: modified_base
<222> LOCATION: (12)..(12)
<223> OTHER INFORMATION: 2'-O-methyladenosine
<220> FEATURE:
<221> NAME/KEY: modified_base
<222> LOCATION: (13)..(13)
<223> OTHER INFORMATION: 2'-O,4'-C-ethylene-linked bicyclic
      ribonucleotide
<220> FEATURE:
<221> NAME/KEY: modified_base
<222> LOCATION: (14)..(14)
```

```
<223> OTHER INFORMATION: 2'-O-methyladenosine
<220> FEATURE:
<221> NAME/KEY: modified_base
<222> LOCATION: (15)..(16)
<223> OTHER INFORMATION: 2'-O,4'-C-ethylene-linked bicyclic
      ribonucleotide
<220> FEATURE:
<221> NAME/KEY: modified_base
<222> LOCATION: (17)..(17)
<223> OTHER INFORMATION: 2'-O-methyladenosine
<220> FEATURE:
<221> NAME/KEY: modified_base
<222> LOCATION: (18)..(18)
<223> OTHER INFORMATION: 2'-O,4'-C-ethylene-linked bicyclic
      ribonucleotide
<220> FEATURE:
<221> NAME/KEY: modified_base
<222> LOCATION: (19)..(20)
<223> OTHER INFORMATION: 2'-O-methyladenosine

<400> SEQUENCE: 80
uccugcaaag cacaccacaa                                               20

<210> SEQ ID NO 81
<211> LENGTH: 20
<212> TYPE: RNA
<213> ORGANISM: Artificial Sequence
<220> FEATURE:
<223> OTHER INFORMATION: Synthetic Sequence - antisense oligonucleotide
      targeting TDP-43 mRNA
<220> FEATURE:
<221> NAME/KEY: modified_base
<222> LOCATION: (1)..(6)
<223> OTHER INFORMATION: 2'-O,4'-C-ethylene-linked bicyclic
      ribonucleotide
<220> FEATURE:
<221> NAME/KEY: modified_base
<222> LOCATION: (3)..(3)
<223> OTHER INFORMATION: t
<220> FEATURE:
<221> NAME/KEY: modified_base
<222> LOCATION: (6)..(6)
<223> OTHER INFORMATION: t
<220> FEATURE:
<221> NAME/KEY: modified_base
<222> LOCATION: (7)..(7)
<223> OTHER INFORMATION: gm
<220> FEATURE:
<221> NAME/KEY: modified_base
<222> LOCATION: (8)..(8)
<223> OTHER INFORMATION: 2'-O,4'-C-ethylene-linked bicyclic
      ribonucleotide
<220> FEATURE:
<221> NAME/KEY: modified_base
<222> LOCATION: (9)..(11)
<223> OTHER INFORMATION: 2'-O-methyladenosine
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (13)..(13)
<223> OTHER INFORMATION: 2'-O,4'-C-ethylene-linked bicyclic
      ribonucleotide
<220> FEATURE:
<221> NAME/KEY: modified_base
<222> LOCATION: (14)..(14)
<223> OTHER INFORMATION: 2'-O-methyladenosine
<220> FEATURE:
<221> NAME/KEY: modified_base
<222> LOCATION: (15)..(15)
<223> OTHER INFORMATION: 2'-O,4'-C-ethylene-linked bicyclic
      ribonucleotide
<220> FEATURE:
<221> NAME/KEY: modified_base
<222> LOCATION: (16)..(16)
```

<223> OTHER INFORMATION: 2'-O-methyladenosine
<220> FEATURE:
<221> NAME/KEY: modified_base
<222> LOCATION: (17)..(18)
<223> OTHER INFORMATION: 2'-O,4'-C-ethylene-linked bicyclic
      ribonucleotide
<220> FEATURE:
<221> NAME/KEY: modified_base
<222> LOCATION: (19)..(19)
<223> OTHER INFORMATION: 2'-O-methyladenosine
<220> FEATURE:
<221> NAME/KEY: modified_base
<222> LOCATION: (20)..(20)
<223> OTHER INFORMATION: 2'-O,4'-C-ethylene-linked bicyclic
      ribonucleotide

<400> SEQUENCE: 81
ccuccugcaa agcacaccac                                                   20

<210> SEQ ID NO 82
<211> LENGTH: 20
<212> TYPE: RNA
<213> ORGANISM: Artificial Sequence
<220> FEATURE:
<223> OTHER INFORMATION: Synthetic Sequence - antisense oligonucleotide
      targeting TDP-43 mRNA
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (2)..(8)
<223> OTHER INFORMATION: 2'-O,4'-C-ethylene-linked bicyclic
      ribonucleotide
<220> FEATURE:
<221> NAME/KEY: modified_base
<222> LOCATION: (2)..(2)
<223> OTHER INFORMATION: t
<220> FEATURE:
<221> NAME/KEY: modified_base
<222> LOCATION: (5)..(5)
<223> OTHER INFORMATION: t
<220> FEATURE:
<221> NAME/KEY: modified_base
<222> LOCATION: (8)..(8)
<223> OTHER INFORMATION: t
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (10)..(10)
<223> OTHER INFORMATION: 2'-O,4'-C-ethylene-linked bicyclic
      ribonucleotide
<220> FEATURE:
<221> NAME/KEY: modified_base
<222> LOCATION: (11)..(13)
<223> OTHER INFORMATION: 2'-O-methyladenosine
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(15)
<223> OTHER INFORMATION: 2'-O,4'-C-ethylene-linked bicyclic
      ribonucleotide
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (17)..(17)
<223> OTHER INFORMATION: 2'-O,4'-C-ethylene-linked bicyclic

```
         ribonucleotide
<220> FEATURE:
<221> NAME/KEY: modified_base
<222> LOCATION: (18)..(18)
<223> OTHER INFORMATION: 2'-O-methyladenosine
<220> FEATURE:
<221> NAME/KEY: modified_base
<222> LOCATION: (19)..(20)
<223> OTHER INFORMATION: 2'-O,4'-C-ethylene-linked bicyclic
         ribonucleotide

<400> SEQUENCE: 82
guccuccugc aaagcacacc                                            20

<210> SEQ ID NO 83
<211> LENGTH: 20
<212> TYPE: RNA
<213> ORGANISM: Artificial Sequence
<220> FEATURE:
<223> OTHER INFORMATION: Synthetic Sequence - antisense oligonucleotide
         targeting TDP-43 mRNA
<220> FEATURE:
<221> NAME/KEY: modified_base
<222> LOCATION: (1)..(2)
<223> OTHER INFORMATION: 2'-O-methyladenosine
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (4)..(4)
<223> OTHER INFORMATION: 2'-O,4'-C-ethylene-linked bicyclic
         ribonucleotide
<220> FEATURE:
<221> NAME/KEY: modified_base
<222> LOCATION: (4)..(4)
<223> OTHER INFORMATION: t
<220> FEATURE:
<221> NAME/KEY: modified_base
<222> LOCATION: (5)..(10)
<223> OTHER INFORMATION: 2'-O,4'-C-ethylene-linked bicyclic
         ribonucleotide
<220> FEATURE:
<221> NAME/KEY: modified_base
<222> LOCATION: (7)..(7)
<223> OTHER INFORMATION: t
<220> FEATURE:
<221> NAME/KEY: modified_base
<222> LOCATION: (10)..(10)
<223> OTHER INFORMATION: t
<220> FEATURE:
<221> NAME/KEY: modified_base
<222> LOCATION: (11)..(11)
<223> OTHER INFORMATION: gm
<220> FEATURE:
<221> NAME/KEY: modified_base
<222> LOCATION: (12)..(12)
<223> OTHER INFORMATION: 2'-O,4'-C-ethylene-linked bicyclic
         ribonucleotide
<220> FEATURE:
<221> NAME/KEY: modified_base
<222> LOCATION: (13)..(15)
<223> OTHER INFORMATION: 2'-O-methyladenosine
<220> FEATURE:
<221> NAME/KEY: modified_base
<222> LOCATION: (16)..(16)
<223> OTHER INFORMATION: gm
<220> FEATURE:
<221> NAME/KEY: modified_base
<222> LOCATION: (17)..(17)
<223> OTHER INFORMATION: 2'-O,4'-C-ethylene-linked bicyclic
         ribonucleotide
<220> FEATURE:
<221> NAME/KEY: modified_base
<222> LOCATION: (18)..(18)
<223> OTHER INFORMATION: 2'-O-methyladenosine
```

```
<220> FEATURE:
<221> NAME/KEY: modified_base
<222> LOCATION: (19)..(19)
<223> OTHER INFORMATION: 2'-O,4'-C-ethylene-linked bicyclic
      ribonucleotide
<220> FEATURE:
<221> NAME/KEY: modified_base
<222> LOCATION: (20)..(20)
<223> OTHER INFORMATION: 2'-O-methyladenosine

<400> SEQUENCE: 83
aaguccuccu gcaaagcaca                                                   20

<210> SEQ ID NO 84
<211> LENGTH: 20
<212> TYPE: RNA
<213> ORGANISM: Artificial Sequence
<220> FEATURE:
<223> OTHER INFORMATION: Synthetic Sequence - antisense oligonucleotide
      targeting TDP-43 mRNA
<220> FEATURE:
<221> NAME/KEY: modified_base
<222> LOCATION: (1)..(2)
<223> OTHER INFORMATION: 2'-O,4'-C-ethylene-linked bicyclic
      ribonucleotide
<220> FEATURE:
<221> NAME/KEY: modified_base
<222> LOCATION: (1)..(1)
<223> OTHER INFORMATION: t
<220> FEATURE:
<221> NAME/KEY: modified_base
<222> LOCATION: (3)..(4)
<223> OTHER INFORMATION: 2'-O-methyladenosine
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (6)..(12)
<223> OTHER INFORMATION: 2'-O,4'-C-ethylene-linked bicyclic
      ribonucleotide
<220> FEATURE:
<221> NAME/KEY: modified_base
<222> LOCATION: (6)..(6)
<223> OTHER INFORMATION: t
<220> FEATURE:
<221> NAME/KEY: modified_base
<222> LOCATION: (9)..(9)
<223> OTHER INFORMATION: t
<220> FEATURE:
<221> NAME/KEY: modified_base
<222> LOCATION: (12)..(12)
<223> OTHER INFORMATION: t
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (14)..(14)
<223> OTHER INFORMATION: 2'-O,4'-C-ethylene-linked bicyclic
      ribonucleotide
<220> FEATURE:
<221> NAME/KEY: modified_base
<222> LOCATION: (15)..(17)
<223> OTHER INFORMATION: 2'-O-methyladenosine
<220> FEATURE:
<221> NAME/KEY: modified_base
<222> LOCATION: (18)..(18)
<223> OTHER INFORMATION: gm
<220> FEATURE:
<221> NAME/KEY: modified_base
<222> LOCATION: (19)..(19)
<223> OTHER INFORMATION: 2'-O,4'-C-ethylene-linked bicyclic
      ribonucleotide
<220> FEATURE:
```

```
<221> NAME/KEY: modified_base
<222> LOCATION: (20)..(20)
<223> OTHER INFORMATION: 2'-O-methyladenosine

<400> SEQUENCE: 84
ucaaguccuc cugcaaagca                                                       20

<210> SEQ ID NO 85
<211> LENGTH: 20
<212> TYPE: RNA
<213> ORGANISM: Artificial Sequence
<220> FEATURE:
<223> OTHER INFORMATION: Synthetic Sequence - antisense oligonucleotide
      targeting TDP-43 mRNA
<220> FEATURE:
<221> NAME/KEY: modified_base
<222> LOCATION: (1)..(4)
<223> OTHER INFORMATION: 2'-O,4'-C-ethylene-linked bicyclic
      ribonucleotide
<220> FEATURE:
<221> NAME/KEY: modified_base
<222> LOCATION: (2)..(3)
<223> OTHER INFORMATION: t
<220> FEATURE:
<221> NAME/KEY: modified_base
<222> LOCATION: (5)..(6)
<223> OTHER INFORMATION: 2'-O-methyladenosine
<220> FEATURE:
<221> NAME/KEY: modified_base
<222> LOCATION: (7)..(7)
<223> OTHER INFORMATION: gm
<220> FEATURE:
<221> NAME/KEY: modified_base
<222> LOCATION: (8)..(14)
<223> OTHER INFORMATION: 2'-O,4'-C-ethylene-linked bicyclic
      ribonucleotide
<220> FEATURE:
<221> NAME/KEY: modified_base
<222> LOCATION: (8)..(8)
<223> OTHER INFORMATION: t
<220> FEATURE:
<221> NAME/KEY: modified_base
<222> LOCATION: (11)..(11)
<223> OTHER INFORMATION: t
<220> FEATURE:
<221> NAME/KEY: modified_base
<222> LOCATION: (14)..(14)
<223> OTHER INFORMATION: t
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (16)..(16)
<223> OTHER INFORMATION: 2'-O,4'-C-ethylene-linked bicyclic
      ribonucleotide
<220> FEATURE:
<221> NAME/KEY: modified_base
<222> LOCATION: (17)..(19)
<223> OTHER INFORMATION: 2'-O-methyladenosine
<220> FEATURE:
<221> NAME/KEY: modified_base
<222> LOCATION: (20)..(20)
<223> OTHER INFORMATION: gm

<400> SEQUENCE: 85
cuucaagucc uccugcaaag                                                       20

<210> SEQ ID NO 86
<211> LENGTH: 20
<212> TYPE: RNA
<213> ORGANISM: Artificial Sequence
<220> FEATURE:
<223> OTHER INFORMATION: Synthetic Sequence - antisense oligonucleotide
``` targeting TDP-43 mRNA
<220> FEATURE:
<221> NAME/KEY: modified_base
<222> LOCATION: (1)..(1)
<223> OTHER INFORMATION: 2'-O,4'-C-ethylene-linked bicyclic
      ribonucleotide
<220> FEATURE:
<221> NAME/KEY: modified_base
<222> LOCATION: (2)..(3)
<223> OTHER INFORMATION: 2'-O-methyladenosine
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (5)..(11)
<223> OTHER INFORMATION: 2'-O,4'-C-ethylene-linked bicyclic
      ribonucleotide
<220> FEATURE:
<221> NAME/KEY: modified_base
<222> LOCATION: (5)..(5)
<223> OTHER INFORMATION: t
<220> FEATURE:
<221> NAME/KEY: modified_base
<222> LOCATION: (8)..(8)
<223> OTHER INFORMATION: t
<220> FEATURE:
<221> NAME/KEY: modified_base
<222> LOCATION: (11)..(11)
<223> OTHER INFORMATION: t
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (13)..(13)
<223> OTHER INFORMATION: 2'-O,4'-C-ethylene-linked bicyclic
      ribonucleotide
<220> FEATURE:
<221> NAME/KEY: modified_base
<222> LOCATION: (14)..(16)
<223> OTHER INFORMATION: 2'-O-methyladenosine
<220> FEATURE:
<221> NAME/KEY: modified_base
<222> LOCATION: (17)..(17)
<223> OTHER INFORMATION: gm
<220> FEATURE:
<221> NAME/KEY: modified_base
<222> LOCATION: (18)..(18)
<223> OTHER INFORMATION: 2'-O,4'-C-ethylene-linked bicyclic
      ribonucleotide
<220> FEATURE:
<221> NAME/KEY: modified_base
<222> LOCATION: (19)..(19)
<223> OTHER INFORMATION: 2'-O-methyladenosine
<220> FEATURE:
<221> NAME/KEY: modified_base
<222> LOCATION: (20)..(20)
<223> OTHER INFORMATION: 2'-O,4'-C-ethylene-linked bicyclic
      ribonucleotide

<400> SEQUENCE: 86
caaguccucc ugcaaagcac                                              20

<210> SEQ ID NO 87
<211> LENGTH: 20
<212> TYPE: RNA
<213> ORGANISM: Artificial Sequence
<220> FEATURE:
<223> OTHER INFORMATION: Synthetic Sequence - antisense oligonucleotide
      targeting TDP-43 mRNA
<220> FEATURE:
<221> NAME/KEY: modified_base
<222> LOCATION: (1)..(3)
<223> OTHER INFORMATION: 2'-O,4'-C-ethylene-linked bicyclic

```
        ribonucleotide
<220> FEATURE:
<221> NAME/KEY: modified_base
<222> LOCATION: (1)..(2)
<223> OTHER INFORMATION: t
<220> FEATURE:
<221> NAME/KEY: modified_base
<222> LOCATION: (4)..(5)
<223> OTHER INFORMATION: 2'-O-methyladenosine
<220> FEATURE:
<221> NAME/KEY: modified_base
<222> LOCATION: (6)..(6)
<223> OTHER INFORMATION: gm
<220> FEATURE:
<221> NAME/KEY: modified_base
<222> LOCATION: (7)..(13)
<223> OTHER INFORMATION: 2'-O,4'-C-ethylene-linked bicyclic
        ribonucleotide
<220> FEATURE:
<221> NAME/KEY: modified_base
<222> LOCATION: (7)..(7)
<223> OTHER INFORMATION: t
<220> FEATURE:
<221> NAME/KEY: modified_base
<222> LOCATION: (10)..(10)
<223> OTHER INFORMATION: t
<220> FEATURE:
<221> NAME/KEY: modified_base
<222> LOCATION: (13)..(13)
<223> OTHER INFORMATION: t
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(15)
<223> OTHER INFORMATION: 2'-O,4'-C-ethylene-linked bicyclic
        ribonucleotide
<220> FEATURE:
<221> NAME/KEY: modified_base
<222> LOCATION: (16)..(18)
<223> OTHER INFORMATION: 2'-O-methyladenosine
<220> FEATURE:
<221> NAME/KEY: modified_base
<222> LOCATION: (19)..(19)
<223> OTHER INFORMATION: gm
<220> FEATURE:
<221> NAME/KEY: modified_base
<222> LOCATION: (20)..(20)
<223> OTHER INFORMATION: 2'-O,4'-C-ethylene-linked bicyclic
        ribonucleotide

<400> SEQUENCE: 87
uucaaguccu ccugcaaagc                                               20

<210> SEQ ID NO 88
<211> LENGTH: 22
<212> TYPE: DNA
<213> ORGANISM: Artificial Sequence
<220> FEATURE:
<223> OTHER INFORMATION: PCR Primer

<400> SEQUENCE: 88
gggaaatctg gtgtatgttg tc                                            22

<210> SEQ ID NO 89
<211> LENGTH: 20
<212> TYPE: DNA
<213> ORGANISM: Artificial Sequence
<220> FEATURE:
<223> OTHER INFORMATION: PCR Primer

<400> SEQUENCE: 89
```

```
tttcaggtcc tgttcggttg                                          20

<210> SEQ ID NO 90
<211> LENGTH: 21
<212> TYPE: DNA
<213> ORGANISM: Artificial Sequence
<220> FEATURE:
<223> OTHER INFORMATION: PCR Primer

<400> SEQUENCE: 90
aaggtgaagg tcggagtcaa c                                        21

<210> SEQ ID NO 91
<211> LENGTH: 22
<212> TYPE: DNA
<213> ORGANISM: Artificial Sequence
<220> FEATURE:
<223> OTHER INFORMATION: PCR Primer

<400> SEQUENCE: 91
ggggtcattg atggcaacaa ta                                       22

<210> SEQ ID NO 92
<211> LENGTH: 21
<212> TYPE: DNA
<213> ORGANISM: Artificial Sequence
<220> FEATURE:
<223> OTHER INFORMATION: PCR Primer

<400> SEQUENCE: 92
ggcgatggtg tgactgtaaa c                                        21

<210> SEQ ID NO 93
<211> LENGTH: 20
<212> TYPE: DNA
<213> ORGANISM: Artificial Sequence
<220> FEATURE:
<223> OTHER INFORMATION: PCR Primer

<400> SEQUENCE: 93
aactgctgaa gctcttcagc                                          20

<210> SEQ ID NO 94
<211> LENGTH: 20
<212> TYPE: DNA
<213> ORGANISM: Artificial Sequence
<220> FEATURE:
<223> OTHER INFORMATION: PCR Primer

<400> SEQUENCE: 94
aaggtcatcc cagagctgaa                                          20

<210> SEQ ID NO 95
<211> LENGTH: 20
<212> TYPE: DNA
<213> ORGANISM: Artificial Sequence
<220> FEATURE:
<223> OTHER INFORMATION: PCR Primer

<400> SEQUENCE: 95
ctgcttcacc accttcttga                                          20

<210> SEQ ID NO 96
<211> LENGTH: 20
<212> TYPE: DNA
<213> ORGANISM: Artificial Sequence
```

```
<220> FEATURE:
<223> OTHER INFORMATION: Synthetic Sequence - control oligonucleotide:
      Combined DNA/RNA Molecule: nucleotides 6 to 15 are
      deoxyribonucleotides-other nucleotides are ribonucleotides
<220> FEATURE:
<221> NAME/KEY: misc_feature
<222> LOCATION: (1)..(20)
<223> OTHER INFORMATION: Phosphorothioate internucleotide linkages
<220> FEATURE:
<221> NAME/KEY: modified_base
<222> LOCATION: (1)..(5)
<223> OTHER INFORMATION: 2'-O,4'-C-ethylene-linked bicyclic
      ribonucleotide
<220> FEATURE:
<221> NAME/KEY: modified_base
<222> LOCATION: (16)..(20)
<223> OTHER INFORMATION: 2'-O,4'-C-ethylene-linked bicyclic
      ribonucleotide

<400> SEQUENCE: 96
cctataggac tatccaggaa                                               20

<210> SEQ ID NO 97
<211> LENGTH: 20
<212> TYPE: RNA
<213> ORGANISM: Artificial Sequence
<220> FEATURE:
<223> OTHER INFORMATION: Synthetic Sequence - control oligonucleotide
<220> FEATURE:
<221> NAME/KEY: modified_base
<222> LOCATION: (1)..(3)
<223> OTHER INFORMATION: 2'-O,4'-C-ethylene-linked bicyclic
      ribonucleotide
<220> FEATURE:
<221> NAME/KEY: modified_base
<222> LOCATION: (2)..(2)
<223> OTHER INFORMATION: t
<220> FEATURE:
<221> NAME/KEY: modified_base
<222> LOCATION: (4)..(4)
<223> OTHER INFORMATION: 2'-O-methyladenosine
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (6)..(6)
<223> OTHER INFORMATION: 2'-O,4'-C-ethylene-linked bicyclic
      ribonucleotide
<220> FEATURE:
<221> NAME/KEY: modified_base
<222> LOCATION: (6)..(6)
<223> OTHER INFORMATION: t
<220> FEATURE:
<221> NAME/KEY: modified_base
<222> LOCATION: (7)..(8)
<223> OTHER INFORMATION: 2'-O-methyladenosine
<220> FEATURE:
<221> NAME/KEY: modified_base
<222> LOCATION: (9)..(9)
<223> OTHER INFORMATION: 2'-O,4'-C-ethylene-linked bicyclic
      ribonucleotide
<220> FEATURE:
<221> NAME/KEY: modified_base
<222> LOCATION: (10)..(10)
<223> OTHER INFORMATION: 2'-O-methyladenosine
<220> FEATURE:
<221> NAME/KEY: modified_base
<222> LOCATION: (11)..(12)
<223> OTHER INFORMATION: 2'-O,4'-C-ethylene-linked bicyclic
      ribonucleotide
<220> FEATURE:
<221> NAME/KEY: modified_base
<222> LOCATION: (11)..(12)
<223> OTHER INFORMATION: t
<220> FEATURE:
```

```
<221> NAME/KEY: modified_base
<222> LOCATION: (13)..(13)
<223> OTHER INFORMATION: gm
<220> FEATURE:
<221> NAME/KEY: modified_base
<222> LOCATION: (14)..(14)
<223> OTHER INFORMATION: 2'-O-methyladenosine
<220> FEATURE:
<221> NAME/KEY: modified_base
<222> LOCATION: (15)..(15)
<223> OTHER INFORMATION: 2'-O,4'-C-ethylene-linked bicyclic
      ribonucleotide
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (17)..(18)
<223> OTHER INFORMATION: 2'-O,4'-C-ethylene-linked bicyclic
      ribonucleotide
<220> FEATURE:
<221> NAME/KEY: modified_base
<222> LOCATION: (19)..(19)
<223> OTHER INFORMATION: 2'-O-methyladenosine
<220> FEATURE:
<221> NAME/KEY: modified_base
<222> LOCATION: (20)..(20)
<223> OTHER INFORMATION: 2'-O,4'-C-ethylene-linked bicyclic
      ribonucleotide

<400> SEQUENCE: 97
cucaguaaca uugacaccac                                             20

<210> SEQ ID NO 98
<211> LENGTH: 24
<212> TYPE: DNA
<213> ORGANISM: Artificial Sequence
<220> FEATURE:
<223> OTHER INFORMATION: Synthetic Sequence - PCR Primer

<400> SEQUENCE: 98
aaagaagtgg aagatttggt gttc                                        24

<210> SEQ ID NO 99
<211> LENGTH: 19
<212> TYPE: DNA
<213> ORGANISM: Artificial Sequence
<220> FEATURE:
<223> OTHER INFORMATION: Synthetic Sequence -  PCR Primer

<400> SEQUENCE: 99
tctttgcatt cagggcgtc                                              19

<210> SEQ ID NO 100
<211> LENGTH: 23
<212> TYPE: DNA
<213> ORGANISM: Artificial Sequence
<220> FEATURE:
<223> OTHER INFORMATION: Synthetic Sequence - PCR Primer

<400> SEQUENCE: 100
tgtcacagtg tttggttctt ttg                                         23

<210> SEQ ID NO 101
<211> LENGTH: 20
<212> TYPE: DNA
<213> ORGANISM: Artificial Sequence
<220> FEATURE:
<223> OTHER INFORMATION: Synthetic Sequence - PCR Primer
```

```
<400> SEQUENCE: 101
agcggataaa aatgggacac                                           20
```

ANTISENSE OLIGONUCLEOTIDE CONTROLLING EXPRESSION AMOUNT OF TDP-43 AND USE THEREOF

CROSS-REFERENCE TO RELATED APPLICATIONS

This patent application is the U.S. national phase of International Patent Application No. PCT/JP2018/025792, filed on Jul. 6, 2018, which claims the benefit of Japanese Patent Application No. 2017-134890, filed on Jul. 10, 2017, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 71,227 bytes ASCII (Text) file named "747233 Sequence-Listing.txt," created Jan. 10, 2020.

TECHNICAL FIELD

The present invention relates to an antisense oligonucleotide that regulates the expression level of TAR DNA-binding protein 43 (TDP-43) and use thereof.

BACKGROUND ART

Amyotrophic lateral sclerosis (ALS) is a progressive neurodegenerative disease in which motor nerves in the corticocerebral motor area and spinal cord degenerate and fall off. It is known that many die within 5 years of onset, due to symptoms such as loss of muscle strength, movement disorder, articulation disorder, dysphagia, respiratory muscle paralysis disorder, and the like. Histopathologically, Bunina body is observed in the lower motor neurons that are being degenerated, and ubiquitin-positive inclusion bodies are observed in the anterior horn of spinal cord neuron. The number of patients in Japan is estimated to be about 9,200. Frontotemporal dementia (FTD) is a neurodegenerative disease presenting with dementia due to degeneration of neurons in the cerebrum and frontal and temporal lobes. Among degenerative dementia, it is common next to Alzheimer's disease and Lewy body type, and develops personality changes, behavioral abnormalities, aphasia and the like other than dementia. In 2006, Neumann et al. and Arai et al. found that TDP-43 is the constituent protein of ubiquitin-positive inclusion bodies found in ALS and FTD, and the mechanism of TDP-43 relating to the onset of ALS/FTD is attracting attention (non-patent documents 1, 2). Furthermore, mutation of the TDP-43 gene was discovered in hereditary ALS/FTD family, and since ALS and FTD have a genetically and pathologically common molecular basis, ALS and FTD are considered to be diseases in the same spectrum (non-patent document 3).

TDP-43 is a 43 kDa protein composed of 414 amino acids and has an RNA-binding region and a nuclear localization signal at the N-terminus and a glycine rich domain at the C-terminus. Localization is primarily in the nucleus and expression is found in tissues throughout the body. TDP-43 is an RNA-binding protein, and various functions relating to RNA regulation such as transcription and translation regulation, splicing regulation and the like have been reported. As a mechanism by which TDP-43 causes neurodegeneration, both the gain-of-toxicity function theory and loss-of-function theory are considered. The findings in support of the gain-of-toxicity function theory are that ALS caused by TDP-43 gene mutation is dominant inheritance, toxicity is observed in disease-related mutant TDP-43, whereas functions are preserved even in disease-related mutant TDP-43. The finding in support of the loss-of-function theory is that TDP-43 in the nucleus disappears in motoneuron cells that have formed ubiquitin-positive TDP-43-positive cytoplasmic inclusion bodies and the function of TDP-43 in the nucleus is considered to have been lost. In addition, characteristics of ALS pathological changes have been observed in nerve-specific conditional knockout mice.

When human TDP-43 is overexpressed in mice, it exhibits neurotoxicity despite being wild-type TDP-43. On the other hand, the expression level of TDP-43 in hetero knockout mice is almost the same as that in wild type mice. From these results, it is considered that there is a mechanism that strictly controls the amount of TDP-43. As one of the mechanisms for regulating the expression level of TDP-43, self-regulation ability by TDP-43 itself has been reported. TDP-43 binds to the TDP-43 binding region (TDPBR) present in the untranslated region on the 3'-side of TDP-43 mRNA and induces self-splicing. Self-spliced mRNA variant is degraded and does not serve as a template for translation of TDP-43 protein. It is considered that, as described, a feedback mechanism exists under which the amount of mRNA decreases when the amount of TDP-43 protein increases, and mRNA increases when the amount of TDP-43 protein decreases, and the amount of autologous mRNA is controlled to be a given amount.

There are several reports on siRNA that lowers the expression level of TDP-43 (e.g., non-patent documents 4-7). However, previously-reported siRNAs have many kinds of target sequences and it is not clear which sequence is optimal as a sequence that reduces the expression level of TDP-43. In addition, an antisense oligonucleotide that acts on human TDP-43 to lower its expression level has not been reported.

DOCUMENT LIST

Non-Patent Documents non-patent document 1: Neumann M. et al., Science, 2006; 314(5796): 130-133.
non-patent document 2: Arai T. et al., Biochem Biophys Res Commu. 2006; 35(3): 602-611.
non-patent document 3: Ling S. C. et al., Neuron, 2013; 79(3): 416-438.
non-patent document 4: Iguchi Y. et al., J Biol Chem, 2009; 284(33): 22059-22066.
non-patent document 5: Koyama A. et al., Nucleic Acids Res., 2016; 44(12): 5820-5836.
non-patent document 6: Aulas A. et al., Mol Neurodegener. 2012; 7: 54
non-patent document 7: Yu Z. et al., J Biol Chem. 2012; 287(27): 22560-22572.

SUMMARY OF THE INVENTION

Problems to be Solved by the Invention

Therefore, the problem of the present invention is to provide an antisense oligonucleotide (ASO) capable of regulating the expression level of TDP-43, and a medicament containing ASO effective for the treatment and/or prophylaxis of diseases involving abnormal aggregation and/or abnormal localization of TDP-43.

Means of Solving the Problems

The present inventors produced various antisense oligonucleotides (ASOs) based on the previously-reported siRNA target sequences and the sequences of the regions including the peripheral sequences thereof and, using cultured cells, screened for ASO that can regulate the expression of endogenous TDP-43. As a result, they have found that ASO having a specific sequence significantly reduces the mRNA amount and protein amount of TDP-43. Furthermore, the present inventors changed the conventional view that ASO can be used to suppress the expression of a target gene, and obtained an idea that self-splicing might be suppressed and the expression level of TDP-43 could be increased by targeting the above-mentioned TDP-43 binding region. They proceeded with the study based on this idea and found that ASO having a specific sequence of the TDP-43 binding region significantly increases the mRNA amount and protein amount of TDP-43. The present invention has been completed based on such finding.

Accordingly, the present invention provides the following.
[1] An antisense oligonucleotide targeting TDP-43 mRNA, comprising a nucleotide sequence complementary to a sequence consisting of at least 10 continuous nucleotides in a nucleotide sequence shown in any of SEQ ID NOs: 2-4.
[2] The antisense oligonucleotide of [1], wherein the oligonucleotide consists of 10-30 nucleotides.
[3] The antisense oligonucleotide of [1] or [2], wherein the aforementioned complementary nucleotide sequence is a nucleotide sequence shown in any of SEQ ID NOs: 45-63 (wherein thymine may be uracil).
[4] The antisense oligonucleotide of any of [1] to [3], wherein the oligonucleotide comprises modification of one or more kinds of sugar-phosphoric acid backbone.
[5] The antisense oligonucleotide of [4], wherein the oligonucleotide comprises 2'-O, 4'-C-ethylene-bridged nucleic acid and deoxyribonucleotide.
[6] The antisense oligonucleotide of [5], wherein the oligonucleotide is of a gapmer type.
[7] The antisense oligonucleotide of [1], wherein the oligonucleotide consists of a nucleotide sequence shown in any of SEQ ID NOs: 11, 22-29 and 35-44.
[8] An antisense oligonucleotide targeting TDP-43 mRNA, comprising a nucleotide sequence complementary to a sequence consisting of at least 10 continuous nucleotides in a nucleotide sequence shown in SEQ ID NO: 5.
[9] The antisense oligonucleotide of [8], wherein the oligonucleotide consists of 10-30 nucleotides.
[10] The antisense oligonucleotide of [8] or [9], wherein the oligonucleotide comprises modification of one or more kinds of sugar-phosphoric acid backbone.
[11] The antisense oligonucleotide of [10], wherein the oligonucleotide comprises 2'-O, 4'-C-ethylene-bridged nucleic acid and 2'-O-methyl-modified nucleic acid.
[12] The antisense oligonucleotide of [10] or [11], wherein the cytosine nucleotide and thymine nucleotide are 2'-O, 4'-C-ethylene-bridged nucleic acids, and adenine nucleotide and guanine nucleotide are 2'-O-methyl-modified nucleic acids.
[13] The antisense oligonucleotide of [8], wherein the oligonucleotide consists of a nucleotide sequence shown in SEQ ID NO: 84, 85 or 87.

[14] An agent for regulating expression of TDP-43, comprising the antisense oligonucleotide of any of [1] to [13].
[15] An agent for treating and/or preventing TDP-43 proteinosis, comprising the antisense oligonucleotide of any of [1] to [13].
[16] The agent of [15], wherein the aforementioned TDP-43 proteinopathy is amyotrophic lateral sclerosis or frontotemporal dementia.
[17] A method for treating and/or preventing TDP-43 proteinopathy in a mammal, comprising administering an effective amount of the antisense oligonucleotide of any of [1] to [13] to the mammal.
[18] The antisense oligonucleotide of any of [1] to [13] for use in the treatment and/or prophylaxis of TDP-43 proteinopathy.
[19] A reagent for analyzing a mechanism of an autoregulation ability of TDP-43, comprising the antisense oligonucleotide of any of [8] to [13].

Effect of the Invention

The antisense oligonucleotide (ASO) of the present invention can effectively reduce the expression level of mRNA and protein of TDP-43, particularly human TDP-43, while also increasing the expression level of mRNA and protein of TDP-43. Therefore, the ASO of the present invention can be used as a therapeutic drug for diseases involving abnormal aggregation and/or abnormal localization of TDP-43, such as amyotrophic lateral sclerosis and frontotemporal dementia. The ASO of the present invention is an ASO targeting the self-regulating function on TDP-43 expression by acting on TDPBR of TDP-43 mRNA, and is innovative also on this point. Furthermore, the ASO of the present invention containing a modified nucleic acid can stably function for a long period (2 weeks or more or 3 months or more) after administration to a living body.

DESCRIPTION OF EMBODIMENTS

Figure 1:
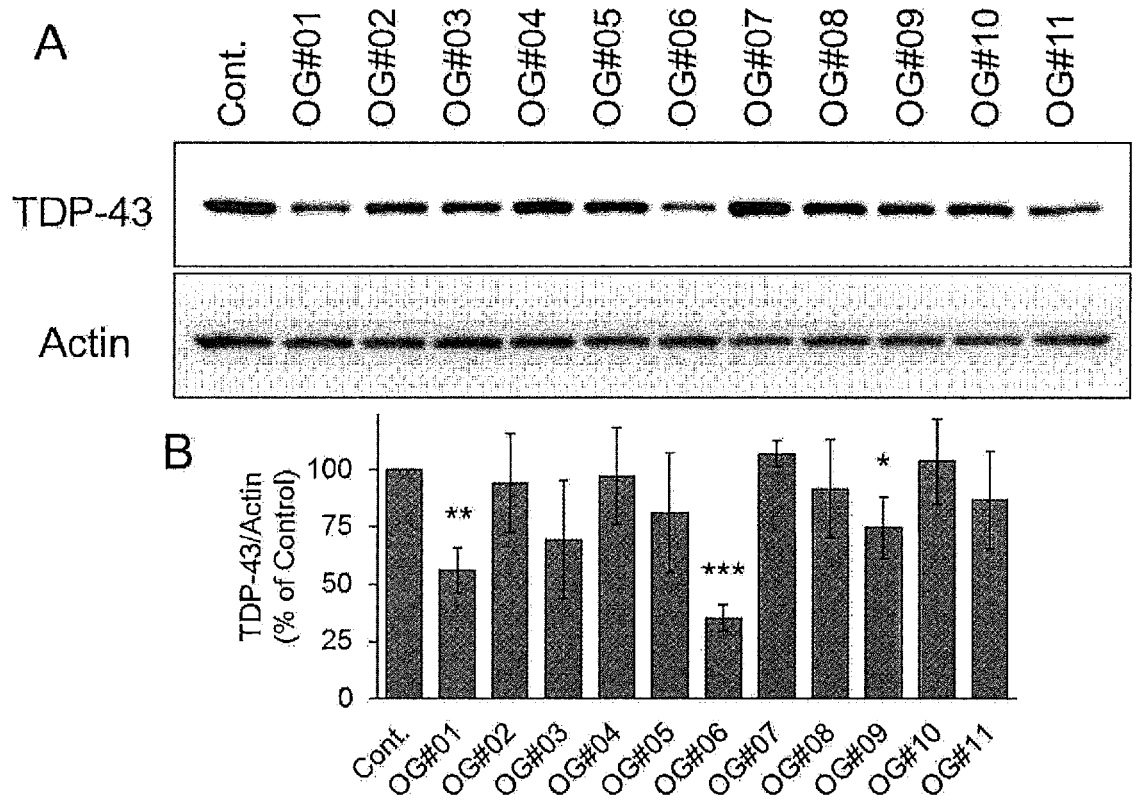
FIG. 1 shows the effect of various Gapmer ASOs on the expression of TDP-43 protein in HEK293 cells. (A, B) The evaluation results of TDP-43 protein amount are shown. HEK293 cells were each treated with Gapmer ASO at 100 nM for 48 hr. The control was not treated with ASO. (B) The comparison results of TDP-43 protein amount are shown (quantification of TDP-43/Actin) (*P=0.05, P<0.01, *P<0.001 versus untreated control).

1. Antisense Oligonucleotide that Regulates Expression Level of TDP-43

1-1. Antisense Oligonucleotides that Suppresses Expression of TDP-43

The present invention provides an antisense oligonucleotide that suppresses expression of TDP-43 and contains a nucleotide sequence complementary to a part of the region of TDP-43 mRNA (hereinafter sometimes to be abbreviated as "suppression type ASO of the present invention"). In the present specification, unless otherwise specified, "expression of TDP-43" is used in the meaning including at least "production of functional TDP-43 protein", preferably in the meaning further including "expression of TDP-43 mRNA", namely, the amount of TDP-43 mRNA.

In the present invention, the "suppression type ASO" means an oligonucleotide that is complementary to a target sequence of TDP-43 mRNA (mRNA encompasses mRNA precursor in the present invention), and suppresses mRNA functions (posttranscriptional editing, translation and the like) by forming a double strand with RNA targeted by the ASO.

The nucleotide sequence of TDP-43 mRNA targeted by the suppression type ASO of the present invention is not particularly limited as long as the suppression type ASO of the present invention can suppress expression of TDP-43 mRNA. Examples thereof include the sequences shown in, for example, any of SEQ ID NO: 1 (5'-AUCAUUAAAGGAAUCAGCGUUCAUAUAUC-CAAUGCC-3'), SEQ ID NO: 2 (5'-GAUCAUUAAAGGAAUCAGCGUUCAUAUAUCCAAUG CCG-3'), SEQ ID NO: 3 (5'-AUGUCUGAAUAUAUUCGGGUAACCGAAGAUGA GAACGAUGAGCCCAUUGAA-3') and SEQ ID NO: 4 (5'-CUUGUCUCCCCUCAUACACAAAAGUA-CAAUAUGAAGCCUUCAUUUAAUCU-CUGCAGUUCA-3'). Among these sequences, a partial sequence of at least 10 (e.g., 10, 15, 16, 17, 18, 19, 20 or more) continuous nucleotides is preferable. In the following, unless otherwise specified, nucleotide sequence is described from left to right and in the direction of 5' to 3'.

1-2. Antisense Oligonucleotide that Promotes Expression of TDP-43

The present invention provides an antisense oligonucleotide that promotes expression of TDP-43 and contains a nucleotide sequence complementary to a part of the region of TDP-43 mRNA (hereinafter sometimes to be abbreviated as "promotion type ASO of the present invention"). In the following, the suppression type ASO and the promotion type ASO of the present invention are sometimes to be collectively abbreviated as "the ASO of the present invention".

In the present invention, the "promotion type ASO" means an oligonucleotide that is complementary to the TDP-43 binding region (TDPBR) of TDP-43 mRNA, and promotes expression level of TDP-43 without causing degradation of the target TDP-43 mRNA by RNase H, Ago2 or other enzymes. As used herein, without causing degradation of the target TDP-43 mRNA means not only that the target TDP-43 mRNA is not degraded at all but also that, even when target TDP-43 mRNA is degraded, degradation of ATDP-43 mRNA is suppressed as compared to that in the absence of promotion type ASO, as a result of which the transcription amount of TDP-43 mRNA exceeds a decrease in the mRNA amount due to a degradation action of the aforementioned enzymes, and the expression of TDP-43 level is substantially promoted. While not wishing to be bound by any theory, the promotion type ASO of the present invention inhibits the binding of TDP-43 protein to TDPBR by forming a double strand with the target RNA, as a result of which it is assumed that the expression of TDP-43 is enhanced by suppressing the induction of self-splicing.

The sequence of TDP-43 mRNA targeted by the ASO of the present invention can be determined by reference to, for example, *Homo sapiens* TAR DNA binding protein (TAR-DBP), mRNA (NCBI Reference Sequence: NM_007375.3), *Homo sapiens* TAR DNA binding protein, mRNA (cDNA clone IMAGE: 3506121) (GenBank: BC001487.2), *Homo sapiens* TAR DNA binding protein, mRNA (cDNA clone IMAGE: 3506121) (GenBank: BC001487.2) and the like. Even when targeting TDP-43 mRNA of a non-human mammal, the target sequence can be similarly determined by reference to known sequences. In the present specification, unless otherwise specified, the nucleotide sequence and nucleotide length and the like targeted by ASO are described based on the nucleotide sequence of human TDP-43 mRNA. The corresponding nucleotide sequence and nucleotide length in non-human mammal orthologs are also encompassed in the contents of description.

The nucleotide sequence of TDP-43 mRNA targeted by the promotion type ASO of the present invention is not particularly limited as long as the promotion type ASO of the present invention can promote expression of TDP-43. For example, a sequence shown in SEQ ID NO: 5 (UGC-UUUGCAGGAGGACUUGAAG) can be mentioned. Particularly, a partial sequence of at least 10 (e.g., 10, 15, 16, 17, 18, 19, 20 or more) continuous nucleotides is preferable.

In the present invention, being "complementary" means not only a sequence that is completely complementary to a target sequence (that is, hybridizes without a mismatch) but also even a sequence including 1 to several (e.g., 2, 3, 4 or 5) mismatches as long as it can hybridize with a target sequence under physiological conditions of mammalian cells. For example, a sequence having identity of 80% or more (e.g., 85% or more, 90% or more, 95% or more, 96% or more, 97% or more, 98% or more, 99% or more), most preferably 100% identity, with a sequence completely complementary to the target sequence in TDP-43 mRNA can be mentioned. The complementarity of individual bases is not limited to formation of Watson-Crick base pairs with the target base, and also includes formation of Hoogsteen base pairs and wobble base pairs with the target base.

The length of the ASO of the present invention is not particularly limited as long as it includes a sequence complementary to all or a part of the sequence shown in any of SEQ ID NOs: 1-4. It is typically 10 to 50 nucleotides. The length is preferably 10 to 30 nucleotide length, more preferably 15 to 30 nucleotide length, and still more preferably 18 to 20 nucleotide length.

Examples of the structural unit of ASO of the present invention include ribonucleotide and deoxyribonucleotide. These nucleotides may be modified (modified nucleotide residues may be referred to as "modified nucleotide residues") or unmodified (unmodified nucleotide residue is sometimes to be referred to as "unmodified nucleotide residue"). Since the suppression type ASO of the present invention contains, for example, a modified nucleotide residue, nuclease resistance is improved and stability can be improved. On the other hand, in the case of promotion type ASO, it is important to include a modified nucleotide residue so as to prevent degradation of the target TDP-43 mRNA. In the promotion type ASO of the present invention, the ratio of modified nucleotide residue is not limited as long as it does not cause degradation by RNase H or the like. It is preferred that one third or more of all nucleotide residues are modified nucleotide residues. The ASO of the present invention may contain a linker region composed of a molecule different from a non-modified nucleotide residue or a modified nucleotide residue.

The ASO of the present invention may be labeled with, for example, a labeling substance. The aforementioned labeling substance is not particularly limited and, for example, fluorescent substance, dye, isotope and the like can be mentioned. Examples of the aforementioned labeling substance include fluorophore such as pyrene, TAMRA, fluorescein, Cy3 dye, Cy5 dye and the like, and examples of the aforementioned dye include Alexa dye such as Alexa488 and the like, and the like. Examples of the aforementioned isotope include stable isotope and radioisotope, and preferred is stable isotope. Since the aforementioned stable isotope has a low risk of exposure and does not require an exclusive facility, it is superior in handling property and can reduce the cost. In addition, the aforementioned stable isotope does not change the physical properties of the labeled compound, and is also superior in properties as a tracer. The aforementioned stable isotope is not particularly limited and, for example, $^{2}H$, $^{13}C$, $^{15}N$, $^{17}O$, $^{18}O$, $^{33}S$, $^{34}S$ and $^{36}S$ can be mentioned.

The aforementioned nucleotide residue contains sugar, base, and phosphoric acid as constituent elements. Ribonucleotide has a ribose residue as sugar and adenine (A), guanine (G), cytosine (C) and uracil (U) (which can also be replaced by thymine (T)) as bases. Deoxyribonucleotide residue has a deoxyribose residue as sugar and adenine (dA), guanine (dG), cytosine (dC) and thymine (dT) (which can also be replaced by uracil (dU)) as bases. In the following, nucleotides having adenine, guanine, cytosine, uracil, and thymine may be referred to as adenine nucleotide, guanine nucleotide, cytosine nucleotide, uracil nucleotide, and thymine nucleotide, respectively.

In the aforementioned non-modified nucleotide residue, the aforementioned each component is the same or substantially the same as, for example, that existing in nature, and preferably the same or substantially the same as that naturally occurring in the human body.

In the aforementioned modified nucleotide residue, for example, any of the constituent elements of the aforementioned non-modified nucleotide residue may be modified. In the present invention, "modification" includes, for example, substitution, addition and/or deletion of the aforementioned constituent elements, and substitution, addition and/or deletion of atoms and/or functional groups in the aforementioned constituent elements. Examples of the aforementioned modified nucleotide residue include naturally occurring nucleotide residue, artificially modified nucleotide residue, and the like. For the aforementioned naturally occurring modified nucleotide residue, Limbach et al (Limbach et al., 1994, Summary: the modified nucleosides of RNA, Nucleic Acids Res. 22: 2183-2196) can be referred to. Examples of the aforementioned modified nucleotide residue include residues of the substitutes for the aforementioned nucleotide.

Examples of the modification of the aforementioned nucleotide residue include modification of a sugar-phosphate backbone (the backbone also includes a base) (hereinafter sugar phosphate backbone).

In the aforementioned sugar-phosphate backbone, when the sugar is ribose, for example, the ribose residue can be modified. In the aforementioned ribose residue, for example, the 2'-position carbon can be modified. Specifically, for example, a hydroxyl group bound to the 2'-position carbon can be modified with a methyl group, or the hydroxyl group can be substituted with hydrogen or halogen such as fluoro. By substituting the hydroxyl group bound to the aforementioned 2'-position carbon with hydrogen, it is possible to substitute the ribose residue with deoxyribose. The aforementioned ribose residue can be substituted with its stereoisomer, for example, and may be substituted with, for example, an arabinose residue. In the following, a nucleic acid in which a hydroxyl group bonded to the 2'-position carbon of sugar is modified with a methyl group as described above may be sometimes referred to as a 2'-O-methyl-modified nucleic acid. In the present invention, the "nucleic acid" includes nucleic acid monomers such as nucleotide and the like.

The aforementioned sugar-phosphate backbone may be substituted with, for example, a non-ribose residue (including non-deoxyribose residues) and/or a non-ribose phosphate backbone having a non-phosphoric acid, and such substitution is also included in the modification of the sugar phosphate backbone. The aforementioned non-ribophosphate backbone may be, for example, the aforementioned ribophosphate backbone modified to be uncharged. Examples of an alternative obtained by substituting the ribophosphate backbone with the aforementioned non-ribophosphate backbone in the aforementioned nucleotide include morpholino, cyclobutyl, and pyrrolidine. Other examples of the aforementioned alternative include artificial nucleic acid. Specific examples thereof include PNA (Peptide Nucleic Acid), bridged structure type artificial nucleic acid (BNA: Bridged Nucleic Acid) and the like. Examples of the BNA include LNA (Locked Nucleic Acid), 2'-O,4'-C-ethylene-bridged nucleic acid (ENA) and the like. The specific structure (nucleoside moiety) of BNA including LNA and ENA that can be used in the present invention is shown below by referring to the drawings described in WO 2016/006697.

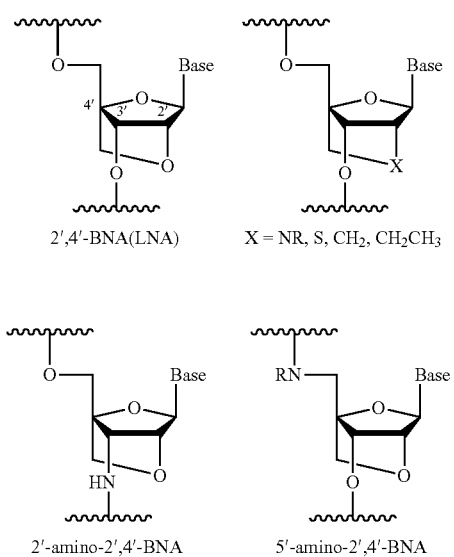

2',4'-BNA(LNA)     X = NR, S, CH$_2$, CH$_2$CH$_3$

2'-amino-2',4'-BNA     5'-amino-2',4'-BNA

-continued

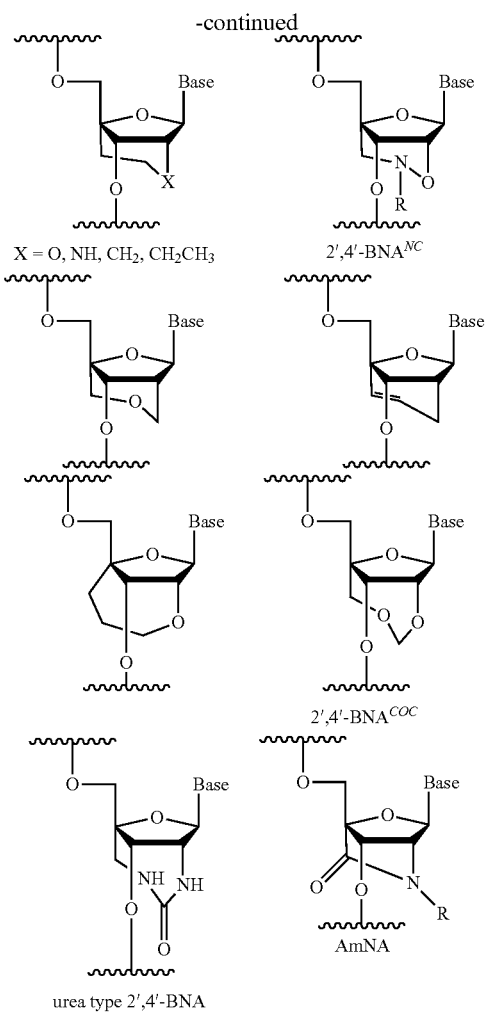

wherein, R is a hydrogen atom, a branched or cyclic alkyl group having 1 to 7 carbon atoms, a branched or cyclic alkenyl group having 2 to 7 carbon atoms, an aryl group having 3 to 12 carbon atoms and optionally containing a hetero atom, an aralkyl group having an aryl moiety having 3 to 12 carbon atoms and optionally containing a hetero atom, or an amino-protecting group for nucleic acid synthesis. Preferably, R is a hydrogen atom, a methyl group, an ethyl group, an n-propyl group, an isopropyl group, a phenyl group, or a benzyl group, more preferably, R is a hydrogen atom or a methyl group, and Base is a base.

Of these, preferred is an ENA having the following nucleoside structure because it does not require extra modification other than efficient stabilization of type A (RNA type) structure.

These artificial nucleic acids can be synthesized by referring to, for example, JP-A-2002-241393, JP-A-2000-297097 and the like.

In the aforementioned sugar-phosphate backbone, for example, a phosphate group can be modified. In the aforementioned sugar-phosphate backbone, a phosphate group at the closest adjacency to the sugar residue is called an "α-phosphate group". The aforementioned α-phosphate group is charged negatively, and the electric charges are distributed evenly over two oxygen atoms that are not linked to the sugar residue. Among the four oxygen atoms in the aforementioned α-phosphate group, the two oxygen atoms not linked to the sugar residue in the phosphodiester linkage between the nucleotide residues hereinafter are referred to as "non-linking oxygens". On the other hand, two oxygen atoms that are linked to the sugar residue in the phosphodiester linkage between the aforementioned nucleotide residues hereinafter are referred to as "linking oxygens". For example, the aforementioned α-phosphate group is preferably modified to be uncharged, or to render the charge distribution between the aforementioned non-linking oxygen asymmetric.

In the aforementioned phosphate group, for example, the aforementioned non-linking oxygen(s) may be substituted. The aforementioned oxygen(s) can be substituted with, for example, any atom selected from S (sulfur), Se (selenium), B (boron), C (carbon), H (hydrogen), N (nitrogen), and OR (R is, for example, an alkyl group or an aryl group) and substitution with S is preferable. It is preferable that both the aforementioned non-linking oxygens are substituted, for example, and it is more preferable that both the non-linking oxygens are substituted with S. Examples of the aforementioned modified phosphate group include phosphorothioates, phosphorodithioates, phosphoroselenates, boranophosphates, boranophosphates, hydrogen phosphonates, phosphoroamidates, alkyl or aryl phosphonates, and phosphotriesters.

The aforementioned phosphate group may be substituted with, for example, the aforementioned phosphate-free linker. The aforementioned linker may contain siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo, methyleneoxymethylimino, or the like. Preferably, the linker may contain a methylenecarbonylamino group and a methylenemethylimino group.

The aforementioned phosphoric acid group may also be substituted with a linker not containing a phosphoric acid. Examples of such linker include those described in "Med. Chem. Commun., 2014, 5, 1454-1471" (shown below by referring to Figure).

(a) netural internucleoside linkage

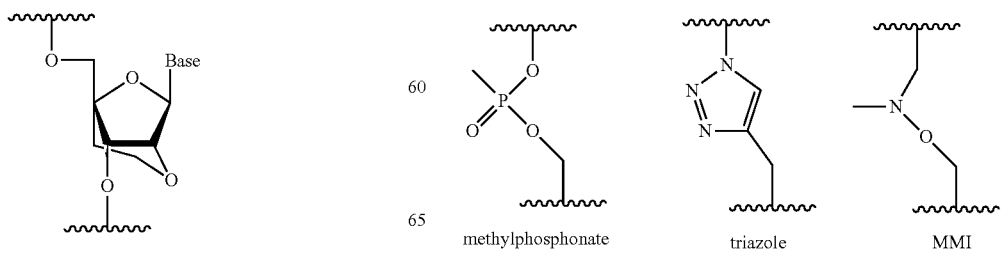

b) anionic internucleoside linkage

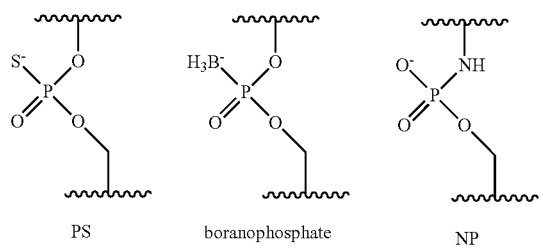

PS          boranophosphate          NP (c) cationic Internucleoside linkage

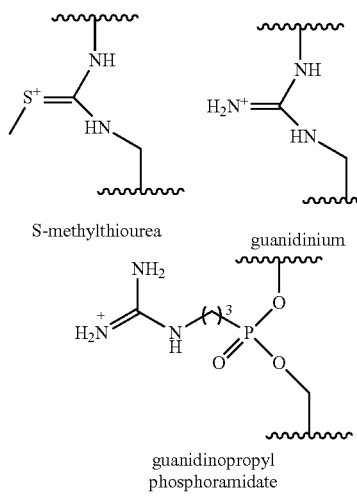

S-methylthiourea          guanidinium guanidinopropyl
phosphoramidate

In the ASO of the present invention, for example, at least one of a nucleotide residue at the 3'-terminus and a nucleotide residue at the 5'-terminus may be modified. For example, the nucleotide residue at either one of the 3'-terminus and the 5'-terminus may be modified, or the nucleotide residues at both the 3'-terminus and the 5'-terminus may be modified. The aforementioned modification may be, for example, as described above, and it is preferable to modify a phosphate group(s) at the end(s). For example, the entire aforementioned phosphate group may be modified, or one or more atoms in the aforementioned phosphate group may be modified. In the former case, for example, the entire phosphate group may be substituted or deleted.

Modification of the aforementioned nucleotide residue(s) at the end(s) may be, for example, addition of any other molecule. Examples of the aforementioned other molecule include functional molecules such as labeling substances as described above and protecting groups. Examples of the aforementioned protecting groups include S (sulfur), Si (silicon), B (boron), and ester-containing groups. The functional molecules such as the aforementioned labeling substances can be used, for example, in the detection and the like of the ASO of the present invention.

The aforementioned other molecule may be, for example, added to the phosphate group of the aforementioned nucleotide residue or may be added to the aforementioned phosphate group or the aforementioned sugar residue via a spacer. For example, the terminus atom of the aforementioned spacer can be added to or substituted for either one of the aforementioned linking oxygens of the aforementioned phosphate group, or O, N, S, or C of the sugar residue. The binding site in the aforementioned sugar residue preferably is, for example, C at the 3'-position, C at the 5'-position, or any atom bound thereto. For example, the aforementioned spacer can also be added to or substituted for a terminus atom of the aforementioned nucleotide alternative such as PNA.

The aforementioned spacer is not particularly limited, and examples thereof include $-(CH_2)_n-$, $-(CH_2)_nN-$, $-(CH_2)_nO-$, $-(CH_2)_nS-$, $O(CH_2CH_2O)_nCH_2CH_2OH$, abasic sugars, amide, carboxy, amine, oxyamine, oxyimine, thioether, disulfide, thiourea, sulfonamide, and morpholino, and also biotin reagents and fluorescein reagents. In the aforementioned formulae, n is a positive integer, and n=3 or 6 is preferable.

Other examples of the aforementioned molecule to be added to the end include dyes, intercalating agents (e.g., acridines), crosslinking agents (e.g., psoralen, mitomycin C), porphyrins (TPPC4, texaphyrin, sapphyrin), polycyclic aromatic hydrocarbons (e.g., phenazine, dihydrophenazine), artificial endonucleases (e.g., EDTA), lipophilic carriers (e.g., cholesterol, cholic acid, adamantane acetic acid, 1-pyrenebutyric acid, dihydrotestosterone, 1,3-Bis-O(hexadecyl)glycerol, a geranyloxyhexyl group, hexadecylglycerol, borneol, menthol, 1,3-propanediol, a heptadecyl group, palmitic acid, myristic acid, O3-(oleoyl)lithocholic acid, O3-(oleoyl)cholic acid, dimethoxytrityl, or phenoxathiine), peptide complexes (e.g., Antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g., biotin), transport/absorption facilitators (e.g., aspirin, vitamin E, folic acid), and synthetic ribonucleases (e.g., imidazole, bisimidazole, histamine, imidazole clusters, acridine-imidazole complexes, Eu$^{3+}$ complexes of tetraazamacrocycles).

In the ASO of the present invention, the aforementioned 5'-terminus may be, for example, modified by a phosphoric acid group or a phosphoric acid group analog. Examples of the aforementioned phosphoric acid group include 5'-monophosphate ((HO)$_2$(O)P—O-5'); 5'-diphosphate ((HO)$_2$(O)P—O—P(HO)(O)—O-5'); 5'-triphosphate ((HO)$_2$(O)P—O—(HO)(O)P—O—P(HO)(O)—O-5'); 5'-guanosine cap (7-methylated or non-methylated methylated, 7m-G-O-5'-(HO)(O)P—O—(HO)(O)P—O—P(HO(O)—O-5'); 5'-adenosine cap (Appp); any modified or unmodified nucleotide cap structure (N—O-5'-(HO)(O)P—O—(HO)(O)P—O—P(HO)(O)—O-5+); 5'-monothiophosphate (phosphorothioate: (HO)$_2$(S)P—O-5'); 5'-monodithiophosphate (phosphorodithioate: (HO)(HS)(S)P—O-5'); 5'-phosphorothiolate ((HO)$_2$(O)P—S-5'); sulfur substituted monophosphate, diphosphate, and triphosphates (e.g., 5'-α-thiotriphosphate, 5'-γ-thiotriphosphate, and the like); 5'-phosphoramidates ((HO)$_2$(O)P—NH-5', (HO)(NH$_2$)(O)P—O-5'); 5'-alkylphosphonates (e.g., RP(OH)(O)—O-5', (OH)$_2$(O)P-5'-CH$_2$, where R is alkyl (e.g., methyl, ethyl, isopropyl, propyl, or the like)); and 5'-alkyletherphosphonates (e.g., RP(OH)(O)—O-5', where R is alkylether (e.g., methoxymethyl, ethoxymethyl, or the like)).

In the aforementioned nucleotide residue, the aforementioned base is not particularly limited and may be, for example, a natural base or a non-natural base. The aforementioned base may be, for example, a naturally-derived base or a synthetic base. As the aforementioned base, for example, a common base, a modified analog thereof, a universal base, and the like can be used.

Examples of the aforementioned base include purine bases such as adenine and guanine and the like, and pyrimidine bases such as cytosine, uracil, thymine and the like. Examples of the aforementioned base include, besides these, inosine, thymine, xanthine, hypoxanthine, nubularine, isoguanisine, tubercidine and the like. Examples of the aforementioned base include alkyl derivatives such as 2-aminoadenine, 6-methylated purine and the like; alkyl derivatives such as 2-propylated purine and the like; 5-halouracil and 5-halocytosine; 5-propynyluracil and 5-propynylcytosine; 6-azouracil, 6-azocytosine and 6-azothymine; 5-uracil (pseudouracil), 4-thiouracil, 5-halouracil, 5-(2-aminopropyl)uracil, 5-aminoallyluracil; 8-halogenated, aminated, thiolated, thioalkylated, hydroxylated and other 8-substituted purines; 5-trifluoromethylated and other 5-substituted pyrimidines; 7-methylguanine; 5-substituted pyrimidine; 6-aza pyrimidine; N-2, N-6, and O-6-substituted purines (including 2-aminopropyladenine); 5-propynyluracil and 5-propynylcytosine; dihydrouracil; 3-deaza-5-aza cytosine; 2-aminopurine; 5-alkyluracil; 7-alkylguanine; 5-alkylcytosine; 7-deazaadenine; N6,N6-dimethyladenine; 2,6-diaminopurine; 5-amino-allyl-uracil; N3-methyluracil; substituted 1,2,4-triazole; 2-pyridinone; 5-nitroindole; 3-nitropyrrole; 5-methoxyuracil; uracil-5-oxyacetic acid; 5-methoxycarbonylmethyluracil; 5-methyl-2-thiouracil; 5-methoxycarbonylmethyl-2-thiouracil; 5-methylaminomethyl-2-thiouracil; 3-(3-amino-3-carboxypropyl)uracil; 3-methylcytosine; 5-methylcytosine; N4-acetylcytosine; 2-thiocytosine; N6-methyladenine; N6-isopentyladenine; 2-methylthio-N6-isopentenyladenine; N-methylguanine; O-alkylated base and the like. Purine and pyrimidine include, for example, those disclosed in U.S. Pat. No. 3,687,808, "Concise Encyclopedia Of Polymer Science And Engineering", pages 858-859, ed. Kroschwitz J. I., John Wiley & Sons, 1990, and Englisch et al., Angewandte Chemie, International Edition, 1991, vol. 30, p. 613. The universal base means a nucleotide base analog capable of forming base pairs with adenine, guanine, cytosine, uracil, thymine and the like. Examples of the aforementioned universal base include, but are not limited to, C-phenyl, C-naphthyl and other aromatic derivatives, inosine, azolecarbozamide, nitroazole derivative (3-nitropyrrole, 4-nitroindole, 5-nitroindole, and 6-nitroindole etc.) (Loakes, 2001, Nucleic Acids Res. 29:2437), the bases described in WO 2007/026485 and the like.

Other examples of the aforementioned modified nucleotide residue include those having no base, i.e., those having an abasic sugar-phosphate backbone. Furthermore, as the aforementioned modified nucleotide residue, for example, the residue described in, for example, WO 2004/080406 can be used.

In another embodiment, the present invention provides ASO (particularly, promotion type ASO) containing 2'-O, 4'-C-ethylene-bridged nucleic acid and 2'-O-methyl-modified nucleic acid. Among others, ASO in which cytosine nucleotide and thymine nucleotide are 2'-O,4'-C-ethylene-bridged nucleic acids and adenine nucleotide and guanine nucleotide are 2'-O-methyl-modified nucleic acids is provided. In such ASO, the ratio of the number of 2'-O,4'-C-ethylene-bridged nucleotide residues:the number of 2'-O-methyl-modified nucleotide residues is preferably 1:4-4:1, more preferably 2:3-3:2.

Examples of the suppression type ASO with modified nucleotide residue include modified oligonucleotides possessed by ASO (OG #06, OG #17-24) that showed high suppressive effect in the Examples described below (respectively shown in SEQ ID NOs: 11, 22-29), ASO containing modified oligonucleotides complementary to a sequence shifted by one base from these target sequences (respectively shown in SEQ ID NOs: 35-44), ASO containing oligonucleotides in which a part of the nucleotide residues of these modified oligonucleotides is non-modified and the like. Examples of the non-modified suppression type include, for example, an ASO containing an oligonucleotide in which all nucleotide residues of the modified oligonucleotide are non-modified (respectively shown in SEQ ID NOs: 45-63. The nucleotide sequence is shown by DNA as a sequence type, but an oligonucleotide in which a part or all deoxyribose residues are substituted with ribose residues, and/or an oligonucleotide in which a part or all thymines are substituted with uracil are/is included in a sequence shown in any of SEQ ID NOs: 45-63), and the like. In a preferable embodiment, the suppression type ASO of the present invention is an ASO composed of an oligonucleotide sequence shown in any of SEQ ID NOs: 11, 22-29 and 35-44 and 45-63. Examples of the promotion type ASO with modified nucleotide residue include modified oligonucleotides possessed by ASO (ok #19, 20, 22) that showed high promotion effect in the Examples described below (respectively shown in SEQ ID NOs: 84, 85, 87), ASO containing oligonucleotides in which a part of the nucleotide residues of these modified oligonucleotides is non-modified, and the like. In a preferable embodiment, the promotion type ASO of the present invention is an ASO composed of an oligonucleotide sequence shown in any of SEQ ID NOs: 84, 85 and 87.

The suppression type ASO of the present invention may be a gapmer type ASO. In the present invention, the "gapmer type ASO" means a chimera antisense oligonucleotide in which an internal region having plural (e.g., 5, 6, 7, 8, 9, 10, 11, 12, 13, 14, 15) deoxyribonucleotides in support of ribonuclease H cleavage are configured between outside regions having one or more (e.g., 1, 2, 3, 4, 5, 6, 7, 8, 9, 10) modified nucleotides. A preferred gapmer type ASO is, for example, an ASO having 10 deoxyribonucleotides in the internal region and 5 modified nucleotides in each outside region thereof. Modification is as described above. To improve stability in vivo, the gapmer type ASO is preferably a phosphorothioate oligonucleotide in which a part (e.g., 50% or more, 60% or more, 70% or more, 80% or more or 90% or more of all phosphoric acid residues) or all of the phosphoric acid group of nucleotide is sulfurized.

The method for synthesizing the ASO of the present invention is not particularly limited, and a conventionally known method can be employed. Examples of the aforementioned synthesis method include synthesis methods according to genetic engineering procedures, chemical synthesis methods and the like. Examples of the genetic engineering procedures include: synthesis methods utilizing in vitro transcription; methods using a vector; methods carried out using a PCR cassette and the like. The aforementioned vector is not particularly limited, and examples thereof include non-virus vectors such as plasmid and the like, and virus vectors and the like. The aforementioned chemical synthesis methods are not particularly limited, and examples thereof include a phosphoramidite method, an H-phosphonate method and the like. The aforementioned chemical synthesis methods can be carried out, for example, using a commercially available automated nucleic acid synthesizer. In the aforementioned chemical synthesis methods, an amidite is generally used. The aforementioned amidite is not particularly limited. Examples of commercially available amidites include RNA Phosphoramidites (2'-O-TBDMSi, trade name, Samchully Pharm. Co., Ltd.), ACE amidite, TOM amidite, CEE amidite, CEM amidite, TEM amidite and the like.

When the ASO of the present invention is composed of a non-modified ribonucleotide residue alone, the ASO of the present invention may be provided as a precursor of the ASO, such as a nucleic acid that encodes the ASO in a state permitting expression thereof (including vector form, hereinafter the same). The expression vector is characterized in that it contains DNA encoding the ASO of the present invention under the control of a promoter functional in the target cell, and other configuration is not limited at all. The expression of TDP-43 in the target cell can be suppressed by introducing the expression vector into the cell by using a gene transfer method known per se.

The aforementioned promoter is not particularly limited as long as it can function in a target cell (cell expressing TDP-43). For example, pol I promoter, pol II promoter, pol III promoter, or the like can be used and preferred is pol III promoter. Specific examples include SV40-derived early promoter, viral promoters such as cytomegalovirus LTR and the like, mammalian constituent protein gene promoters such as β-actin gene promoter and the like, and promoters such as U6 promoter, H1 promoter, tRNA promoter and the like. The above-mentioned expression vector preferably contains a transcription termination signal, that is, a terminator region at the downstream of the nucleic acid encoding the ASO of the present invention. Furthermore, it may further contain a selection marker gene for selection of transformed cells (a gene imparting resistance to drugs such as tetracycline, ampicillin, kanamycin and the like, a gene complementing an auxotrophic mutation, etc.).

The kind of vector used for the expression vector in the present invention is not particularly limited, and examples of vector suitable for administration to human include virus vectors such as retrovirus, adenovirus, adeno-associated virus and the like, plasmid vector and the like. Among these, adenovirus is advantageous in that the gene transfer efficiency is extremely high, it can be introduced into non-dividing cells as well and the like. In view of sustainability of therapeutic effects, adeno-associated virus is also preferably used since it shows relatively high gene transfer efficiency, can be introduced into non-dividing cells, and can be integrated into the chromosome via an inverted terminal sequence (ITR).

2. Expression Regulating Agent Containing ASO of the Present Invention

The ASO of the present invention can suppress or promote expression of TDP-43, as mentioned above. Therefore, the ASO of the present invention can be used as a TDP-43 expression inhibitor containing a suppression type ASO, or a TDP-43 expression promoting agent containing a promotion type ASO. Hereinafter these are collectively referred to as "the expression regulating agent of the present invention". The ASO contained in the expression regulating agent of the present invention may be in the form of an ASO molecule, in the form of a nucleic acid encoding ASO as mentioned above, or the like, and may be a mixture of these forms. The expression regulating agent of the present invention can be used for, for example, elucidation of the mechanism that causes collapse of the strict expression level regulation mechanism of TDP-43, resulting in the formation of cytoplasmic aggregates of TDP-43 to cause neurodegeneration.

As the expression regulating agent of the present invention, for example, the aforementioned ASO can be administered alone or together with a pharmacologically acceptable carrier to a subject in which the aforementioned TDP-43 gene is present. The aforementioned administration step can be performed by, for example, contacting the aforementioned ASO with the aforementioned subject of administration. Examples of the aforementioned subject to which the nucleic acid molecule of the present invention is administered include cells, tissues and organs. Examples of the aforementioned administration subject include cell, tissue or organ of human. The aforementioned administration may be performed, for example, in vivo or in vitro.

To promote introduction of the ASO of the present invention into the target cell, the expression regulating agent of the present invention may further contain a reagent for nucleic acid introduction. As the reagent for nucleic acid introduction, cationic lipids such as atelocollagen; liposome; nanoparticle; Lipofectin, lipofectamine, DOGS (Transfectam), DOPE, DOTAP, DDAB, DHDEAB, HDEAB, polybrene, poly(ethyleneimine) (PEI) and the like, and the like can be used.

3. Medicament Containing ASO of the Present Invention

The ASO of the present invention can regulate the expression level of TDP-43. Thus, a medicament containing the ASO (hereinafter sometimes to be abbreviated as "the medicament of the present invention") can be used for the treatment and/or prophylaxis of diseases involving abnormal aggregation and/or abnormal localization of TDP-43, by regulating the expression level of TDP-43. Examples of such disease include TDP-43 proteinopathy accompanying TDP-43 positive inclusion bodies and the like. Examples of the aforementioned TDP-43 proteinopathy include amyotrophic lateral sclerosis, frontotemporal dementia (e.g., FTLD-TDP-43, FTLD-tau), Alzheimer's disease, Lewy body dementia, Down syndrome, hippocampus sclerosis, familial British dementia, parkinsonism (e.g., Perry syndrome), polyglutamine disease (e.g., Huntington's disease, spinocerebellar ataxia type 3), myopathy (e.g., sporadic inclusion body myositis, inclusion bodies myopathy, oculopharyngeal muscular dystrophy, distal myopathy, myofibrillar myopathy), corticobasal degeneration, progressive supranuclear paralysis, argyrophilic grain disease and the like, each of which accompany TDP-43 positive inclusion bodies (e.g., Clotilde Lagier-Tourenne et al., Human Molecular Genetics, 2010, Vol. 19, Review Issue 1; Arai, Neuropathology, 2014, Vol. 34, 578-588.).

The medicament of the present invention may be an effective amount of the ASO of the present invention used alone, or may be formulated as a pharmaceutical composition together with any carrier, for example, pharmaceutically acceptable carrier. The ASO to be contained in the medicament of the present invention may be in the form of an ASO molecule, in the form of a nucleic acid encoding ASO as mentioned above, or the like, and may be a mixture of these forms.

Examples of the pharmaceutically acceptable carrier include, but are not limited to, excipients such as sucrose, starch and the like, binders such as cellulose, methylcellulose and the like, disintegrants such as starch, carboxymethylcellulose and the like, lubricants such as magnesium stearate, aerogel and the like, aromatic such as citric acid, menthol and the like, preservatives such as sodium benzoate, sodium bisulfite and the like, stabilizers such as citric acid, sodium citrate and the like, suspensions such as methylcellulose, polyvinyl pyrrolidone and the like, dispersing agents such as surfactant and the like, diluents such as water, saline and the like, base wax and the like.

To promote introduction of the ASO of the present invention into the target cell, the medicament of the present invention may further contain a reagent for nucleic acid introduction. As the reagent for nucleic acid introduction, those similar to the aforementioned can be used.

In addition, the medicament of the present invention may be a pharmaceutical composition in which the ASO of the present invention is encapsulated in a liposome. Liposome is a fine closed vesicle having an inner phase surrounded by one or more lipid bilayers, and can generally retain a water-soluble substance in the inner phase and a liposoluble substance in the lipid bilayer. In the present specification, when "encapsulated" is used, the ASO of the present invention may be held in the liposome inner phase or in the lipid bilayer. The liposome to be used in the present invention may be a single layer membrane or a multi-layer membrane, and the particle size can be appropriately selected from, for example, the range of 10-1000 nm, preferably 50-300 nm. In consideration of the deliverability to the target tissue, the particle size may be, for example, not more than 200 nm, preferably not more than 100 nm.

Examples of a method for encapsulating a water-soluble compound such as oligonucleotides in a liposome include a lipid film method (vortex method), a reversed-phase evaporation method, a surfactant-removing method, a freeze-thawing method, a remote loading method, and the like. However, the method is not limited to these and any known method can be appropriately selected.

The medicament of the present invention can be orally or parenterally administered to a mammal (e.g., human, rat, mouse, guinea pig, rabbit, sheep, horse, swine, bovine, monkey). Parenteral administration is desirable.

A preparation preferable for parenteral administration (e.g., subcutaneous injection, muscle injection, topical injecting, intraperitoneal administration and the like) is an aqueous or non-aqueous isotonic aseptic injection liquid which may contain antioxidant, buffer, bacteriostatic agent, isotonicity agent and the like. In addition, an aqueous or non-aqueous aseptic suspension agent can be mentioned which may contain suspension, solubilizer, thickener, stabilizer, preservative and the like. The preparation can be encapsulated in a container in a unit dose or multiple doses like ampoules and vials. Alternatively, the active ingredient and a pharmaceutically acceptable carrier can also be lyophilized and stored in a state only requiring dissolving or suspending in a suitable sterile vehicle immediately before use. As another preparation suitable for parenteral administration, a spray and the like can be mentioned.

The content of the ASO of the present invention in the pharmaceutical composition is, for example, about 0.1 to 100 wt % of the whole pharmaceutical composition.

While the dose of the medicament of the present invention varies depending on the administration objective, administration method, the kind of target disease, severity, condition of the subject of administration (sex, age, body weight and the like), for systemic administration to an adult, for example, 2 nmol/kg or more and 50 nmol/kg or less as a single dose of the ASO of the present invention is generally desirable; for topical administration, 1 pmol/kg or more and 10 nmol/kg or less as a single dose of the ASO of the present invention is generally desirable. Such dose is desirably administered 1 to 10 times, more preferably 5 to 10 times. While the ASO of the present invention can be stably present in the body for a long period of time, it is preferably administered at regular intervals to maintain a high effect. This interval is not particularly limited, and examples include every day, every three days, every week, every two weeks, every month, every three months, every six months, and the like.

The medicament of the present invention can be used in combination with, for example, other therapeutic agents for amyotrophic lateral sclerosis or frontotemporal dementia, for example, therapeutic agents for these diseases already on the market. Examples of the therapeutic drug include glutamic acid action inhibitor (e.g., riluzole etc.), neurotrophic factor (e.g., insulin-like growth factor-1, 5-HT1A receptor agonist (e.g., xaliproden) etc.) and the like. These concomitant drugs can be formulated together with the medicament of the present invention and administered as a single preparation, or can also be formulated separately from the medicament of the present invention and used simultaneously or with a time difference in a route the same as or different from the route of the medicament of the present invention. The dose of these concomitant drugs may be an amount generally used when the drug is administered alone, or may be reduced from an amount generally used.

A treatment and/or prophylactic method including administering an effective amount of the ASO of the present invention or the medicament of the present invention to a mammal (animal to be the subject of treatment or prophylaxis) is also included in the present invention. Specific examples of the effective amount, dose, mammal and other matters are as described in 3.

4. ASO for Analysis of Mechanism of Autoregulation Ability of TDP-43

As shown in the below-mentioned Examples, in one embodiment of the present invention, when the promotion type ASO of the present invention considered to be stable for a long term was introduced, the expression level of TDP-43 was transiently increased and decreased, and thereafter the increasing and decreasing effects disappeared. While not wishing to be bound by any theory, it is considered that the autoregulation ability of TDP-43, which collapsed once, was recovered by the aforementioned introduction of ASO. Therefore, the promotion type ASO of the present invention or a reagent for analysis of mechanism of autoregulation ability of TDP-43 which contains the ASO (hereinafter to be abbreviated as "the reagent of the present invention") can be used for analyzing the mechanism of the autoregulation ability of TDP-43. Specifically, cells are recovered at particular time intervals (e.g., 24 hr, 48 hr, 72 hr) after introduction of the promotion type ASO of the present invention and proteome analysis and microarray analysis are performed using the protein or mRNA extracted from respective cells, whereby protein and mRNA that changed at each progress time can be identified as candidates of factors involved in the mechanism of autoregulation of TDP-43. Alternatively, a test substance is further administered to cells administered with the promotion type ASO of the present invention, and when a transient increase or decrease in the expression level of TDP-43 is not found, the test substance can be identified as candidates of factors involved in the mechanism of autoregulation of TDP-43.

Where necessary, such ASO can be provided, for example, in a form bonded to a functional molecule fluorescence dye such as labeling substance, protecting group and the like described in the above-mentioned 1. In addition, it can be provided in the form of a nucleic acid encoding the ASO of the present invention and the like. When the reagent of the present invention contains two or more kinds of ASO (e.g., when plural kinds of promotion type ASO are used, when one or more kinds of promotion type ASO and ASO used as a control are contained and the like), the reagent can be provided as a kit containing each ASO in a separate reagent. Such kit may further contain, besides the ASO of the present invention, for example, reagents necessary for culturing cells (e.g., basal medium, medium additive and the like), or reagents for nucleic acid introduction, or other reagents for detecting or measuring the expression of TDP-43 such as antibody, probe, PCR primer, array and the like. As the reagents, the substances exemplified in the above-mentioned 1-3 can be similarly mentioned.

While the present invention is explained in detail in the following by referring to Examples, the present invention is not limited thereto.

EXAMPLE

In the below-mentioned Examples, experiments were performed as follows.

Design of ASO

For the mRNA sequence of TDP-43, the following sequences were referred to.
1) *Homo sapiens* TAR DNA binding protein (TARDBP), mRNA (NCBI Reference Sequence: NM_007375.3) (https://www.ncbi.nlm.nih.gov/nuccore/NM_007375.3)
2) *Homo sapiens* TAR DNA binding protein, mRNA (cDNA clone IMAGE: 3506121) (GenBank: BC001487.2) (https://www.ncbi.nlm.nih.gov/nuccore/BC001487.2)

Various Gapmer ASOs consisting of the nucleotide sequences shown in Table 1 were designed and produced. OG #07 was designed based on the sequence of *Homo sapiens* TAR DNA binding protein, mRNA (cDNA clone IMAGE: 3506121) (GenBank: BC001487.2), and others were designed based on the sequence of *Homo sapiens* TAR DNA binding protein (TARDBP), mRNA (NCBI Reference Sequence: NM_007375.3). For the sequence of control ASO OG #C1 (SEQ ID NO: 96:CCTATaggactatccAGGAA) (upper case is ENA, lower case is DNA), Jiang et al., Neuron, 2016; Volpicelli-Daley et al., J Neurosci., 2016; d'Ydewalle et al., Neuron, 2017; Becker et al., Nature, 2017 were referred to. As Gapmer ASO, bridged type nucleic acid ENA (2'-O,4'-C-ethylene-bridged Nucleic Acids) (5 bases) was added to both ends of DNA (10 base) to produce hybrid nucleic acid (total 20 bases) (Table 1). Along therewith, ASO complementary to a sequence shifted by one base from the target sequence of any of OG #06, 17-24 was designed (Table 1).

TABLE 1

| ASO name | Gapmer ASO sequence (upper case ENA, lower case DNA) base sequence (5'→3') | SEQ ID NO: |
|---|---|---|
| OG#01 | GGGCTcatcgttctcATCTT | 6 |
| OG#02 | TTCAAtgggctcatcGTTCT | 7 |
| OG#03 | CAGTCttaagatcttTCTTG | 8 |
| OG#04 | CAAAGgctcatcttgGCTTT | 9 |
| OG#05 | TTAATgatcaagtccTCTCC | 10 |
| OG#06 | ATATAtgaacgctgaTTCCT | 11 |
| OG#07 | GTGCTtaggttaggcATTGG | 12 |
| OG#08 | ATCCAtgcttgagccAAAGC | 13 |

TABLE 1-continued

| ASO name | Gapmer ASO sequence (upper case ENA, lower case DNA) base sequence (5'→3') | SEQ ID NO: |
|---|---|---|
| OG#09 | AAGGCttcatattgtACTTT | 14 |
| OG#10 | AATATccattatgcaCCACC | 15 |
| OG#11 | GTGCTtaggttcggcATTGG | 16 |
| OG#12 | CTTTAatgatcaagtCCTCT | 17 |
| OG#13 | TCCTTtaatgatcaaGTCCT | 18 |
| OG#14 | ATTCCtttaatgatcAAGTC | 19 |
| OG#15 | TGATTcctttaatgaTCAAG | 20 |
| OG#16 | GCTGAttcctttaatGATCA | 21 |
| OG#17 | ACGCTgattcctttaATGAT | 22 |
| OG#18 | GAACGctgattcctTAATG | 23 |
| OG#19 | ATGAAcgctgattccTTTAA | 24 |
| OG#20 | ATATGaacgctgattCCTTT | 25 |
| OG#21 | GGATAtatgaacgctGATTC | 26 |
| OG#22 | TTGGAtatatgaacgCTGAT | 27 |
| OG#23 | CATTGgatatatgaaCGCTG | 28 |
| OG#24 | GGCATtggatatatgAACGC | 29 |
| OG#25 | TCGGCattggatataTGAAC | 30 |
| OG#26 | GTTCGgcattggataTATGA | 31 |
| OG#27 | AGGTTcggcattggaTATAT | 32 |
| OG#28 | TTAGGttcggcattgGATAT | 33 |
| OG#29 | GCTTAggttcggcatTGGAT | 34 |
| OG#41 | GATATatgaacgctgATTCC | 35 |
| OG#42 | CGCTGattcctttaaTGATC | 36 |
| OG#43 | AACGCtgattcctttAATGA | 37 |
| OG#44 | TGAACgctgattcctTTAAT | 38 |
| OG#45 | TATGAacgctgattcCTTTA | 39 |
| OG#46 | TATATgaacgctgatTCCTT | 40 |
| OG#47 | TGGATatatgaacgcTGATT | 41 |
| OG#48 | ATTGGatatatgaacGCTGA | 42 |
| OG#49 | GCATTggatatatgaACGCT | 43 |
| OG#50 | CGGCAttggatatatGAACG | 44 |

Blocker ASO was designed using CLIP34nt and CLIP6 shown to bind to TDP-43 in vitro as target sequences (Bhardwaj A, Myers M P, Buratti E, Baralle F E. Nucleic Acids Res. 2013; 1(9):5062-5074.). Using 42 bases containing CLIP34nt of TDP-43 mRNA and surrounding sequences (SEQ ID NO: 64: AAAGGAGAGAGCGCGUGCAGAGACUUGGUGGUGC AUAAUGGA, underline shows CLIP34nt) as a target sequence, 12 kinds of ASOs from ok #01 to ok #12 were produced and, using 34 bases containing CLIP6 and surrounding sequences (SEQ ID NO: 65: GAGC<u>UUGUGGUGUGCUUUGCAGGAGGACUUGAA</u>G, underline shows CLIP6) as a target sequence, 10 kinds of ASOs from ok #13 to ok #22 were produced. For the sequence of control ASO ok #C2 (SEQ ID NO: 97:CTCagTaaCaTTgaCaCCaC) (upper case is ENA, lower case is 2' O-methyl-modified nucleic acid (2'OMe)), Staropoli et al., Genomics, 2015; Kapeli et al., Nat Commun., 2016 was referred to. ENA was used for a nucleic acid having cytosinebase (C) and thymine base (T), and 2'OMe was used for a nucleic acid having adenine base (A) and guanine base (G), whereby a hybrid nucleic acid (20 bases) was produced (Table 2).

TABLE 2

Blocker ASO sequence (upper case ENA, lower case 2'OMe)

| ASO name | base sequence (5'→3') | SEQ ID NO: |
| --- | --- | --- |
| ok#01 | CTgCaCgCgCTCTCTCCTTT | 66 |
| ok#02 | CTCTgCaCgCgCTCTCTCCT | 67 |
| ok#03 | gTCTCTgCaCgCgCTCTCTC | 68 |
| ok#04 | aagTCTCTgCaCgCgCTCTC | 69 |
| ok#05 | CCaagTCTCTgCaCgCgCTC | 70 |
| ok#06 | CaCCaagTCTCTgCaCgCgC | 71 |
| ok#07 | aCCaCCaagTCTCTgCaCgC | 72 |
| ok#08 | gCaCCaCCaagTCTCTgCaC | 73 |
| ok#09 | aTgCaCCaCCaagTCTCTgC | 74 |
| ok#10 | TTaTgCaCCaCCaagTCTCT | 75 |
| ok#11 | CaTTaTgCaCCaCCaagTCT | 76 |
| ok#12 | TCCaTTaTgCaCCaCCaagT | 77 |
| ok#13 | gCaaagCaCaCCaCaagCTC | 78 |
| ok#14 | CTgCaaagCaCaCCaCaagC | 79 |
| ok#15 | TCCTgCaaagCaCaCCaCaa | 80 |
| ok#16 | CCTCCTgCaaagCaCaCCaC | 81 |
| ok#17 | gTCCTCCTgCaaagCaCaCC | 82 |
| ok#18 | aagTCCTCCTgCaaagCaCa | 83 |
| ok#19 | TCaagTCCTCCTgCaaagCa | 84 |
| ok#20 | CTTCaagTCCTCCTgCaaag | 85 |
| ok#21 | CaagTCCTCCTgCaaagCaC | 86 |
| ok#22 | TTCaagTCCTCCTgCaaagC | 87 |

Screening Method of ASO Using Cultured Cells

HEK293 cells were treated with ASO, and the protein amount of endogenous TDP-43 was evaluated by Western blot, and the mRNA amount was evaluated by qRT-PCR.

HEK293 cells were transfected with ASO by using Lipofectamine 3000 (L3000015, Thermo). The medium was exchanged 4 hr after transfection, 44 hr later (48 hr after administration), the cells were dissolved in RIPA buffer (08714-04, Nacalai) and protein was extracted. The cells after ASO treatment for 24 hr or 48 hr were dissolved in TRIzol (10296028, Thermo) and RNA was extracted by a phenol-chloroform extraction method. ASO non-treatment was used as a comparison control.

In Western blot, TDP-43 Antibody (10782-2-AP, Proteintech) was used for the evaluation of TDP-43 protein amount, and Anti-beta-Actin, Clone AC-15 (A5441, Sigma-Aldrich) were used for the evaluation of Actin protein.

In the evaluation of the mRNA amount, the extracted mRNA was reverse-transcribed into cDNA by utilizing QuantiTect Reverse Transcription Kit (205313, Qiagen), and qRT-PCR was performed using the obtained cDNA as a template. In qRT-PCR, primer TDP43Fex2-2; GGGAAATCTGGTGTATGTTGTC:SEQ ID NO: 88, TDP43Rex3; TTTCAGGTCCTGTTCGGTTG:SEQ ID NO: 89 were used for TDP-43 mRNA, primer GAPDH_qF; AAGGTGAAGGTCGGAGTCAAC:SEQ ID NO: 90, GAPDH_qR; GGGGTCATTGATGGCAACAATA:SEQ ID NO: 91 were used for GAPDH mRNA, and enzyme SYBR (registered trade mark) Premix Ex Taq™ II (RR820S, Takara) was used.

ASO Evaluation Method In Vivo (Wild-Type Mouse)

ASO was administered to the cerebral ventricle of a wild-type mouse by using a Hamilton syringe, the brain and spinal cord were removed from the mouse 2 weeks after the administration, and the protein amount of TDP-43 was evaluated by Western blot and the mRNA amount was evaluated by qRT-PCR. A mouse administered with physiological saline was used as a comparison control.

In Western blot, the protein amount of TDP-43 extracted using RIPA buffer from the brain and spinal cord was evaluated. TDP-43 Antibody (10782-2-AP, Proteintech) recognizing mouse and human TDP-43, Anti-beta-Actin recognizing Actin, and Clone AC-15 (A5441, Sigma-Aldrich) were used.

In the evaluation of the mRNA amount, the extracted mRNA was reverse-transcribed into cDNA by TRIzol treatment and phenol-chloroform extraction method, and qRT-PCR was performed using the obtained cDNA as a template.

In qRT-PCR, primer mTDP43ex4.1-F; GGCGATGGTGTGACTGTAAAC:SEQ ID NO: 92, mTDP43ex5-R; AACTGCTGAAGCTCTTCAGC:SEQ ID NO: 93 were used for mouse TDP-43 mRNA, primer mGAPDH-F; AAGGTCATCCCAGAGCTGAA:SEQ ID NO: 94, mGAPDH-R; CTGCTTCACCACCTTCTTGA: SEQ ID NO: 95 were used for mouse GAPDH mRNA, and enzyme SYBR (registered trade mark) Premix Ex Tag™ II (RR820S, Takara) was used.

ASO Evaluation Method In Vivo (Human TDP-43 Expression Mouse)

ASO was administered to the cerebral ventricle of a human TDP-43A315T BAC Tg mouse (Swarup V, Phaneuf D, Bareil C, Robertson J, Rouleau G A, Kriz J, Julien J P. Brain. 2011; 134(Pt 9): 2610-2626.) by using a Hamilton syringe, the cerebral cortex, hippocampus, spinal cord were removed from the mouse 2 weeks or 3 months after the administration, and the protein amount of human TDP-43 was evaluated by Western blot and the human TDP-43 mRNA amount was evaluated by qRT-PCR. A mouse administered with control ASO was used as a comparison control.

In Western blot, the protein amount of TDP-43 extracted using RIPA buffer from the cerebral cortex, hippocampus, and spinal cord was evaluated. Human TDP-43 Antibody (H00023435-M01, Abnova) recognizing human TDP-43, Anti-beta-Actin recognizing Actin, and Clone AC-15 (A5441, Sigma-Aldrich) were used.

In the evaluation of the human TDP-43 mRNA amount, the extracted mRNA was reverse-transcribed into cDNA by TRIzol treatment and phenol-chloroform extraction method, and qRT-PCR was performed using the obtained cDNA as a template.

In qRT-PCR, primer TDP43Fex22; GGGAAATCTGGTGTATGTTGTC:SEQ ID NO: 88, TDP43Rex3; TTTCAGGTCCTGTTCGGTTG:SEQ ID NO: 89 were used for human TDP-43 mRNA, primer TDP43qFdelta6; AAAGAAGTGGAAGATTTGGTGTTC: SEQ ID NO: 98, TDP43qRdelta7A; TCTTTGCATTCAGGGCGTC:SEQ ID NO: 99 were used for degradation type human TDP-43 mRNA, primer TDP43qF4; TGTCACAGTGTTTGGTTCTTTTG:SEQ ID NO: 100, TDP43qR4; AGCGGATAAAAATGGGACAC:SEQ ID NO: 101 were used for translation type human TDP-43 mRNA, primer mGAPDH-F; AAGGTCATCCCAGAGCTGAA:SEQ ID NO: 94, mGAPDH-R; CTGCTTCACCACCTTCTTGA:SEQ ID NO: 95 were used for mouse GAPDH mRNA, and enzyme SYBR (registered trade mark) Premix Ex Taq™ II (RR820S, Takara) was used.

Example 1 In Vitro Verification of Suppression Type ASO

HEK293 cells were treated with each suppression type ASO (Gapmer ASO OG #01-11) (11 kinds) at 100 nM for 48 hr. As a result, as compared to ASO non-treatment, TDP-43 protein amount decreased by about 45% by OG #01 treatment, about 65% by OG #06 treatment, and about 25% by OG #09 treatment (FIG. 1).

Figure 2:
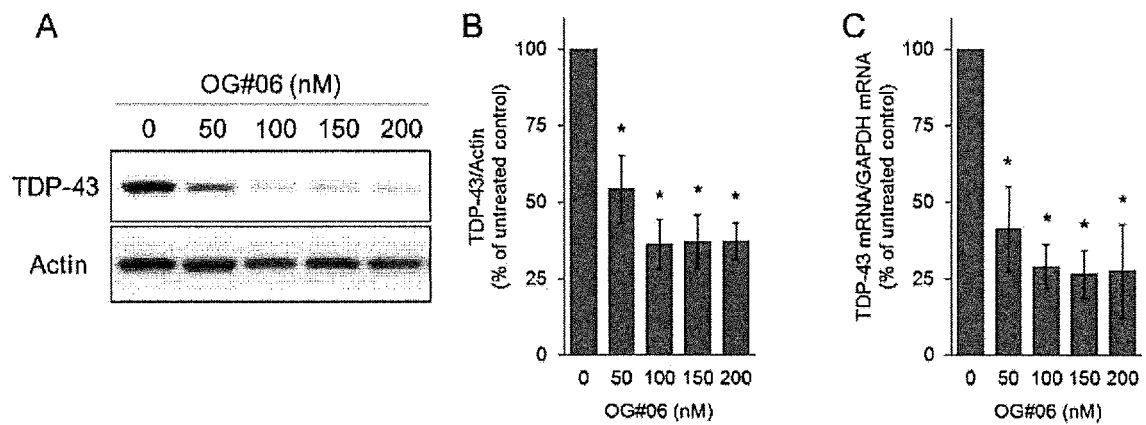
FIG. 2 shows the effect of Gapmer ASO OG #06 on the expression of TDP-43 protein and mRNA in HEK293 cells. HEK293 cells were each treated with Gapmer ASO OG #06 at 0, 50, 100, 150, 200 nM for 48 hr. (A, B) The evaluation results of TDP-43 protein amount are shown. (B) The comparison results of TDP-43 protein amount are shown (quantification of TDP-43/Actin) (*P<0.01 versus untreated control). (C) The comparison results of TDP-43 mRNA amount by qRT-PCR are shown (quantification of TDP-43 mRNA/GAPDH mRNA) (*P<0.01 versus untreated control).

Successively, when studied by changing the treatment concentration of most effective Gapmer ASO OG #06, the protein amount of TDP-43 decrease by OG #06 treatment depending on the concentration (50% decrease by 50 nM treatment, 70% decrease by 100, 150, 200 nM treatment) (FIG. 2A, B). In addition, a decrease in mRNA was also confirmed (60% decrease by 50 nM treatment, 75% decrease by 100, 150, 200 nM) (FIG. 2C).

Figure 3:
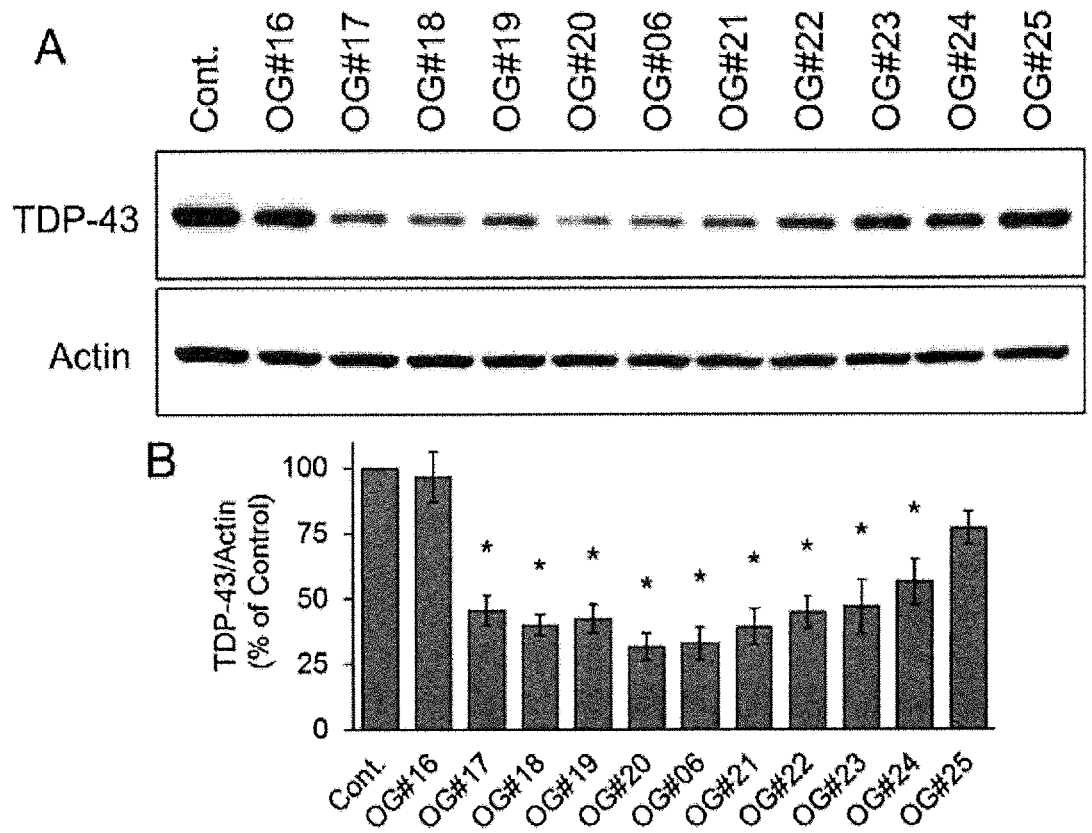
FIG. 3 shows the effect of various Gapmer ASOs on the expression of TDP-43 protein in HEK293 cells. (A, B) The evaluation results of TDP-43 protein amount are shown. HEK293 cells were each treated with Gapmer ASO at 100 nM for 48 hr. The control was not treated with ASO. (B) The comparison results of TDP-43 protein amount are shown (quantification of TDP-43/Actin) (*P<0.01 versus untreated control).

Next, ASO targeting a sequence surrounding Gapmer ASO OG #06 was studied. As a result, a decrease of about 50% or more in the protein amount of TDP-43 was found by a treatment with OG #17, 18, 19, 20, 06, 21, 22, 23, 24 at 100 nM for 48 hr as compared to ASO non-treatment (FIG. 3).

From the above results, ASO of Gapmer ASO OG #17, 18, 19, 20, 06, 21, 22, 23 or 24 was particularly effective, and the 36 base sequence (AUCAUUAAAGGAAUCAGCGUUCAUAUAUC-CAAUGCC:SEQ ID NO: 1) targeted by these ASOs and (GAUCAUUAAAGGAAUCAGCGUUCAUAUAUC-CAAUGCCG:SEQ ID NO: 2) further having 1 base at both terminals were identified as target sequences capable of effectively suppressing the expression level of TDP-43. Furthermore, 51 base sequence containing the target sequence of OG #01 (including target sequence of OG #01 and 25 bases before and 6 bases thereafter) (AUGUCUGAAUAUAUUCGG-GUAACCGAAGAUGAGAACGAUGAGCCCAUUGAA: SEQ ID NO: 3), 60 base sequence containing target sequence of OG #09 (including target sequence of OG #09 and 20 bases before and thereafter) (CUUGUCUCCCCU-CAUACACAAAAGUACAAUAUGAAGCCUU-CAUUUAAUCUCUGCAGUUCA:SEQ ID NO: 4) are also considered to be target sequences capable of effectively suppressing the expression level of TDP-43.

Example 2 In Vivo Verification of Suppression Type ASO Using Wild-Type Mouse

Figure 4:
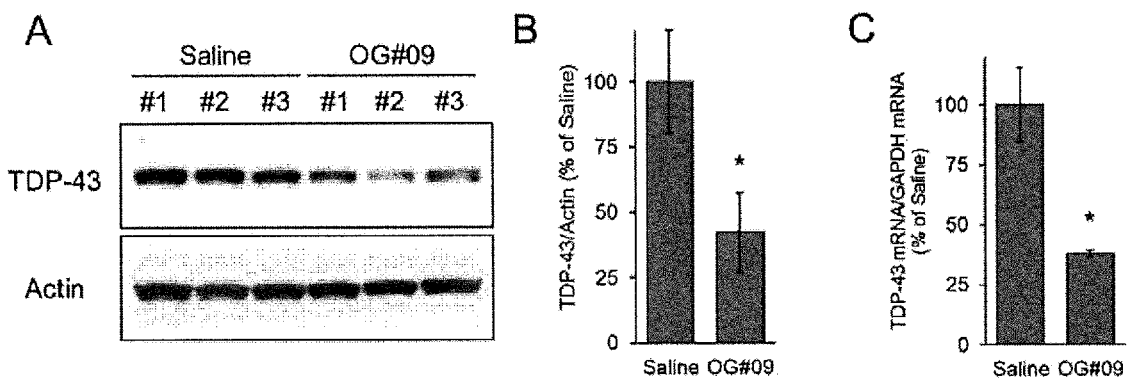
FIG. 4 shows the effect of Gapmer ASO OG #09 on the expression of TDP-43 protein and mRNA in mouse cerebral ventricle. 10 μg of Gapmer ASO OG #09 was administered to the cerebral ventricle of wild-type mice (1 day after birth), and analysis was performed 2 weeks later. Three mice from each of physiological saline-administered mice and OG #09-administered mice were compared for analysis. (A, B) The evaluation results of TDP-43 protein amount are shown. (B) The comparison results of TDP-43 protein amount are shown (quantification of TDP-43/Actin) (*P=0.02 versus Saline control). (C) The comparison results of TDP-43 mRNA amount by qRT-PCR are shown (quantification of TDP-43 mRNA/GAPDH mRNA) (*P=0.002 versus Saline control).

Whether or not the ASO of the present invention is effective in an individual was verified. Gapmer ASO OG #09 having the same target sequence for human and mouse was administered by 10 μg to the cerebral ventricle of a wild-type mouse (one day old) and analyzed 2 weeks later. As a result, TDP-43 protein amount decreased by about 60% and mRNA amount decreased by about 70% by OG #09 administration as compared to a mouse administered with physiological brine (FIG. 4).

Since the results highly correlate with the results of the cultured cells in Example 1, ASOs other than Gapmer ASO OG #09 (e.g., ASO of Gapmer ASO OG #01, #17, 18, 19, 20, 06, 21, 22, 23 or 24) are considered to be similarly effective for an individual.

Example 3 In Vitro Study of Promotion Type ASO

Figure 5:
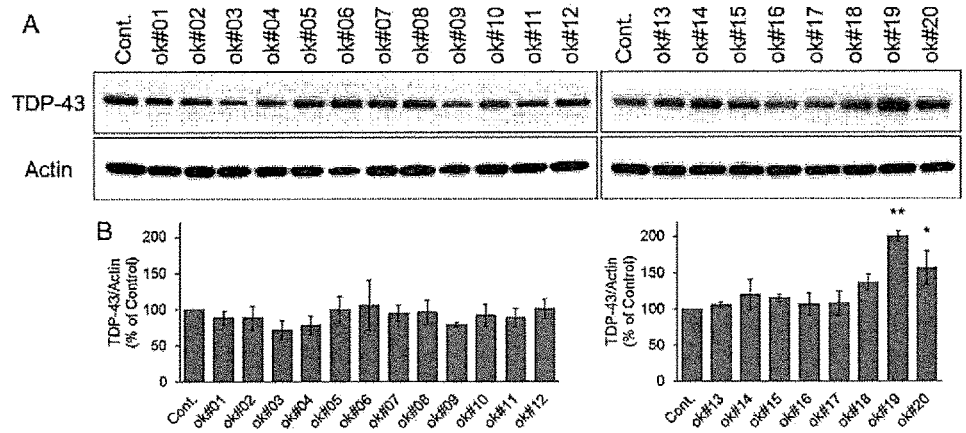
FIG. 5 shows the effect of various Blocker ASOs on the expression of TDP-43 protein in HEK293 cells. (A, B) The evaluation results of TDP-43 protein amount are shown. HEK293 cells were each treated with Blocker ASO at 200 nM for 48 hr. The control was not treated with ASO. (B) The comparison results of TDP-43 protein amount are shown (quantification of TDP-43/Actin) (*P<0.05, **P<0.01 versus untreated control).

HEK293 cells were treated with each promotion type ASO (Blocker ASO ok #01-20) (20 kinds) at 200 nM for 48 hr. As a result, TDP-43 protein amount increased 2-fold by Blocker ASO ok #19 treatment as compared to ASO non-treatment (FIG. 5).

Figure 6:
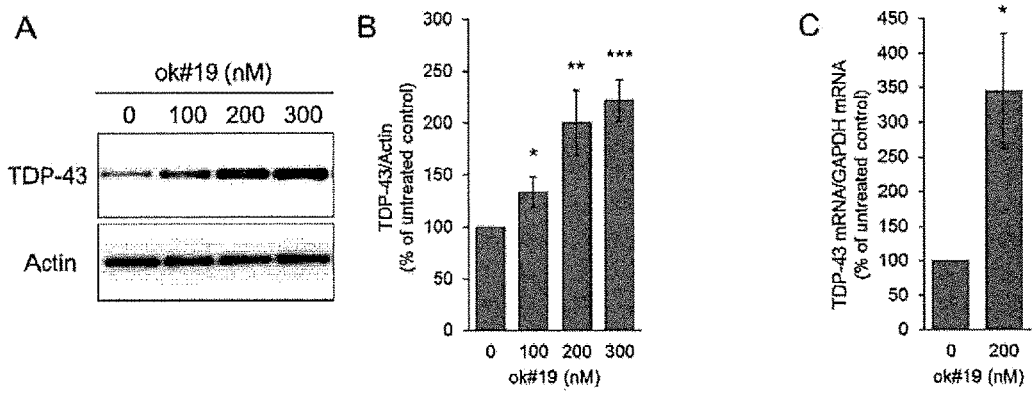
FIG. 6 shows the effect of Blocker ASO ok #19 on the expression of TDP-43 protein and mRNA in HEK293 cells. HEK293 cells were each treated with Blocker ASO ok #19 at 0, 100, 200, 300 nM for 48 hr (A, B) or 0, 200 nM for 24 hr (C). (A, B) The evaluation results of TDP-43 protein amount are shown. (B) The comparison results of TDP-43 protein amount are shown (quantification of TDP-43/Actin) (*P<0.05, P<0.01, *P<0.001 versus untreated control). (C) The comparison results of TDP-43 mRNA amount by qRT-PCR are shown (quantification of TDP-43 mRNA/GAPDH mRNA) (*P<0.01 versus untreated control).

When studied by changing the treatment concentration of Blocker ASO ok #19, the protein amount of TDP-43 increased in ok #19 depending on the treatment concentration (FIG. 6A, B). In addition, ok #19 treatment at 200 nM for 24 hr was also confirmed to increase TDP-43 mRNA (FIG. 6C).

Figure 7:
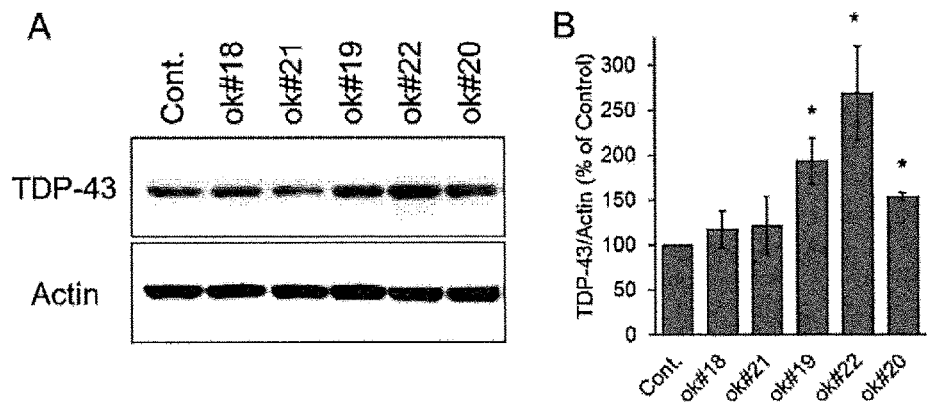
FIG. 7 shows the effect of various Blocker ASOs on the expression of TDP-43 protein in HEK293 cells. (A, B) The evaluation results of TDP-43 protein amount are shown. HEK293 cells were each treated with Blocker ASO at 200 nM for 48 hr. The control was not treated with ASO. (B) The comparison results of TDP-43 protein amount are shown (quantification of TDP-43/Actin) (*P<0.01 versus untreated control).

Next, ASO containing bases surrounding Blocker ASO ok #19 was studied. As a result, a 2-fold increase of TDP-43 protein by ok #19, 2.5-fold increase by ok #22, and 1.5-fold increase by ok #20, were found by a treatment at 200 nM for 48 hr as compared to ASO non-treatment (FIG. 7).

From the above results, ASO of Blocker ASO ok #19, 22 or 20 was particularly effective, the 22 base sequence (UGCUUUGCAGGAGGACUUGAAG:SEQ ID NO: 5) targeted by these ASOs was identified as a target sequence capable of effectively promoting the expression level of TDP-43.

Example 4 In Vivo Verification of Suppression Type ASO Using Wild-Type Mouse

Figures 1, 8:
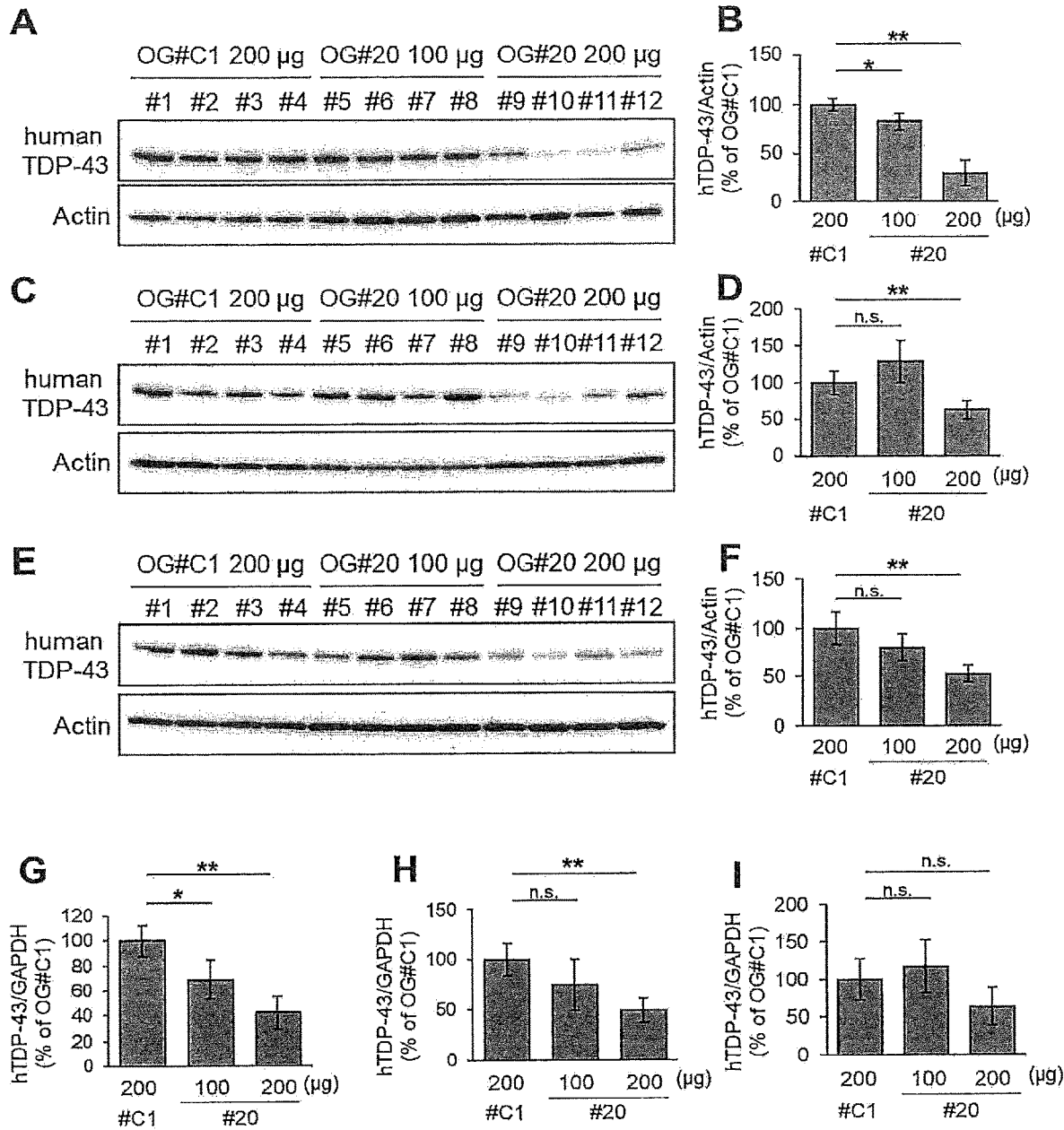
FIG. 8 shows the effect of Gapmer ASO OG #20 on the expression of human TDP-43 protein and mRNA in the cerebral cortex, hippocampus and spinal cord of mice expressing human TDP-43. Gapmer ASO OG #20 was administered to the cerebral ventricle of human TDP-43 A315T BAC Tg mice (6 weeks old), and analysis was performed 2 weeks later. By comparing the mice administered with 200 μg of control ASO OG #C1 with the mice administered with 100 μg and 200 μg of OG #20, 4 individual mice each were analyzed. (A-F) show the evaluation results of the amount of human TDP-43 protein. The results for cerebral cortex (A, B), hippocampus (C, D), spinal cord (E, F) are shown. The quantification results of human TDP-43 protein/mouse Actin protein are shown (B, D, F) (*P<0.05, **P<0.01 versus control ASO OG #C1). (G, H, I) The evaluation results of human TDP-43 mRNA amount are shown. The results of cerebral cortex (G), hippocampus (H) and spinal cord (I) are shown (quantification of human TDP-43 mRNA/mouse GAPDH mRNA) (*P<0.05, **P<0.01 versus control ASO OG #C1). Similarly, Gapmer ASO OG #20 was administered, and analysis was performed 3 months later. Three mice administered with 200 μg of control ASO OG #C1 and four mice administered with 200 μg of OG #20 were analyzed. (J-O) The evaluation results of human TDP-43 protein amount are shown. The results of cerebral cortex (J, K), hippocampus (L, M) and spinal cord (N, O) are shown. The quantification results of human TDP-43 protein/mouse Actin protein are shown (K, M, O) (*P<0.05 versus control ASO OG #C1). (P, Q, R) The evaluation results of human TDP-43 mRNA amount are shown. The results of cerebral cortex (P), hippocampus (Q) and spinal cord (R) are shown (quantification of human TDP-43 mRNA/mouse GAPDH mRNA) (*P<0.05, **P<0.01 versus control ASO OG #C1).
Figures 2, 8:
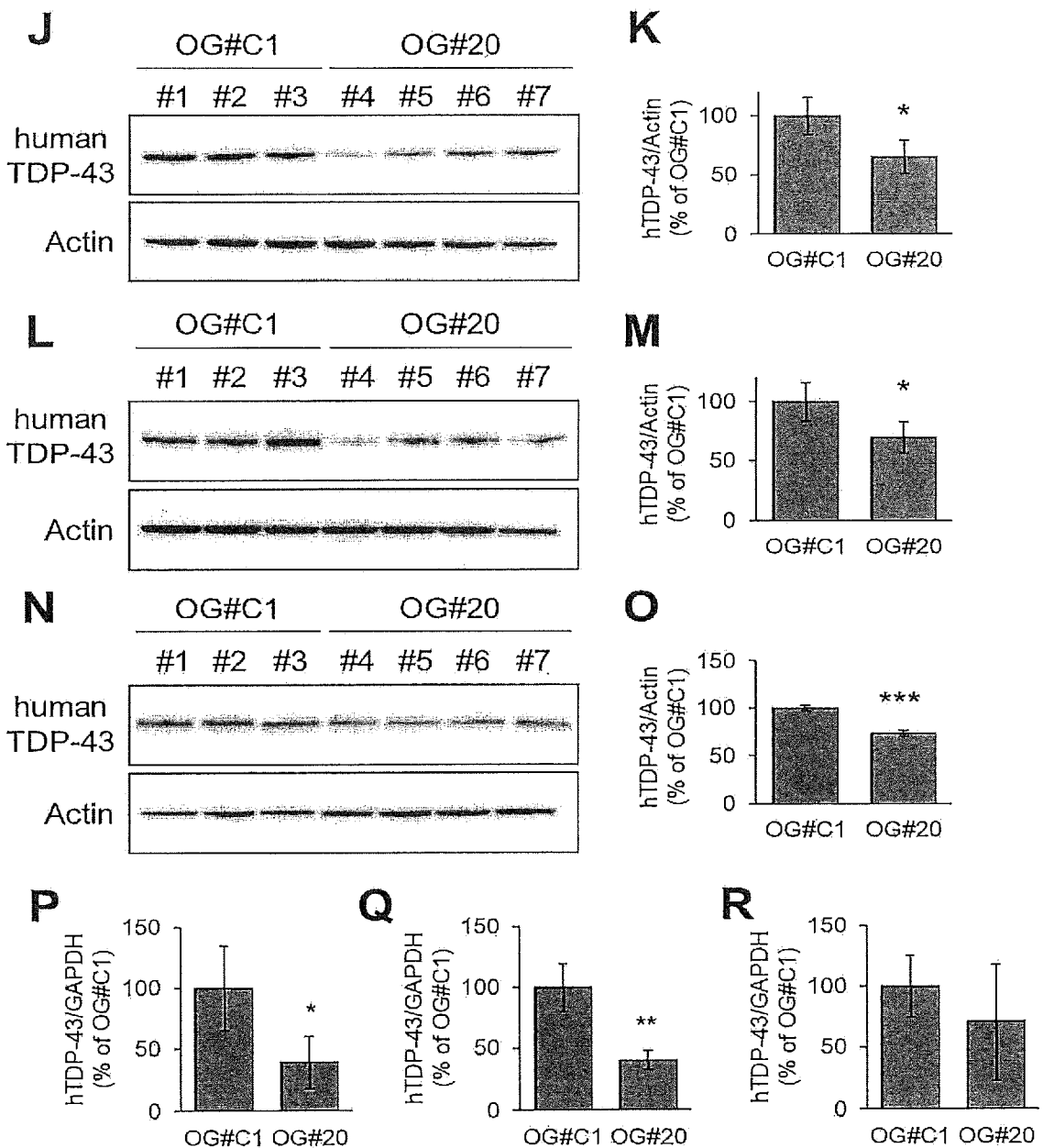
Figures 1, 9:
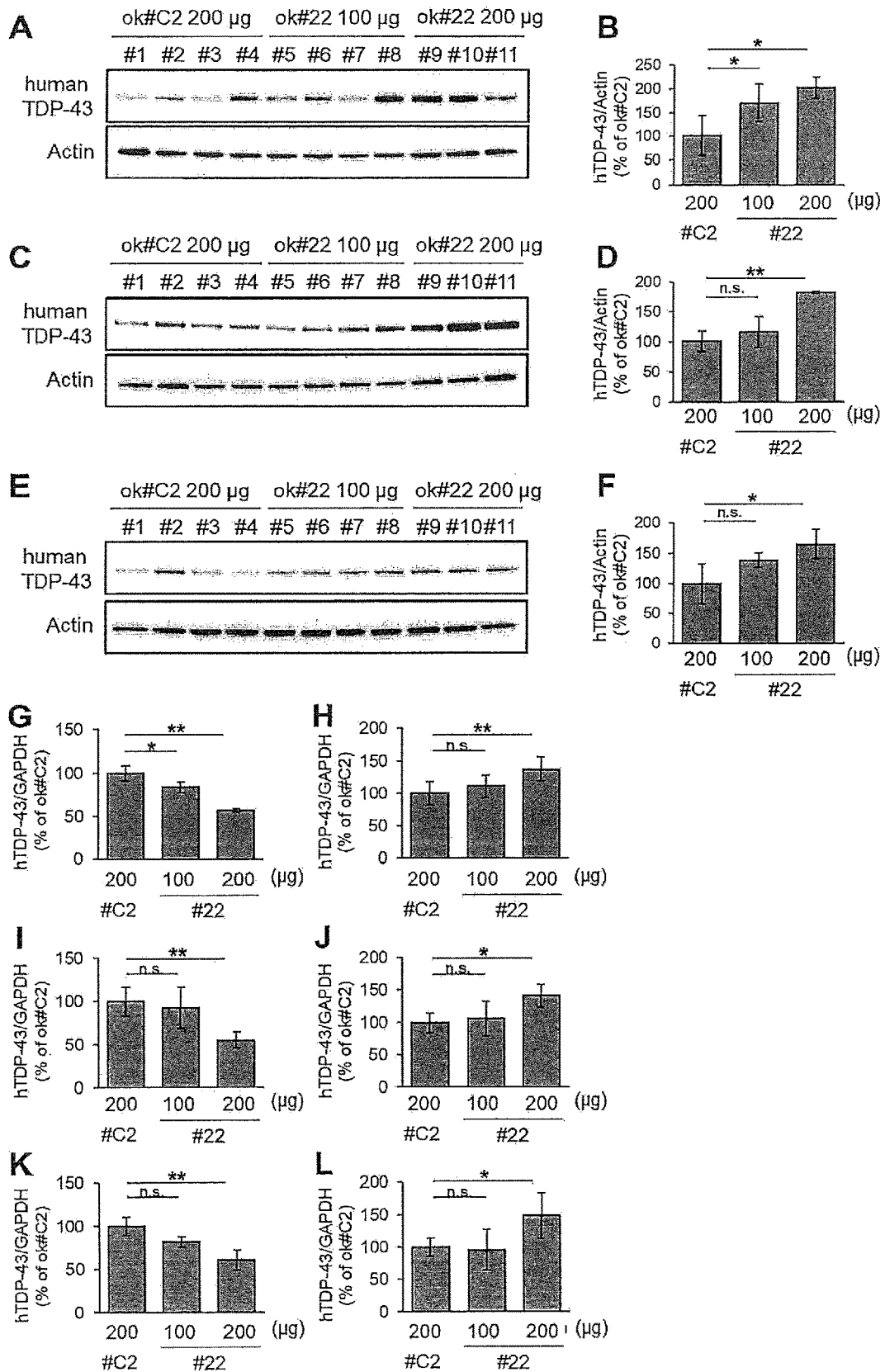
FIG. 9 shows the effect of Blocker ASO ok #22 on the expression of human TDP-43 protein and mRNA in the cerebral cortex, hippocampus and spinal cord of mice expressing human TDP-43. Blocker ASO ok #22 was administered to the cerebral ventricle of human TDP-43 A315T BAC Tg mice (6 weeks old), and analysis was performed 2 weeks later. Four mice administered with 200 μg of control ASO OG #C1, four mice administered with 100 μg of ok #22 and three mice administered with 200 μg of ok #22 were analyzed. (A-F) show the evaluation results of the amount of human TDP-43 protein. The results for cerebral cortex (A, B), hippocampus (C, D), spinal cord (E, F) are shown. The quantification results of human TDP-43 protein/mouse Actin protein are shown (B, D, F) (*P<0.05, **P<0.01 versus control ASO OG #C1). (G-L) The evaluation results of human TDP-43 mRNA amount are shown. The results of cerebral cortex (G, H), hippocampus (I, J) and spinal cord (K, L) are shown. The quantification results (G, I, K) of (degradation type) human TDP-43 mRNA to be degraded and mouse GAPDH mRNA, and the quantification results (H, J, L) of (non-degradation type) human TDP-43 mRNA maintained in the nucleus or translated and mouse GAPDH mRNA are shown (*P<0.05, **P<0.01 versus control ASO ok #C2). Similarly, Blocker ASO ok #22 was administered, and analysis was performed 3 months later. Four mice administered with 200 μg of control ASO ok #C2 and six mice administered with 200 μg of ok #22 were analyzed. (M-R) The evaluation results of human TDP-43 protein amount are shown. The results of cerebral cortex (M, N), hippocampus (O, P) and spinal cord (Q, R) are shown. The quantification results of human TDP-43 protein/mouse Actin protein are shown (M, P, R).
Figures 2, 9:
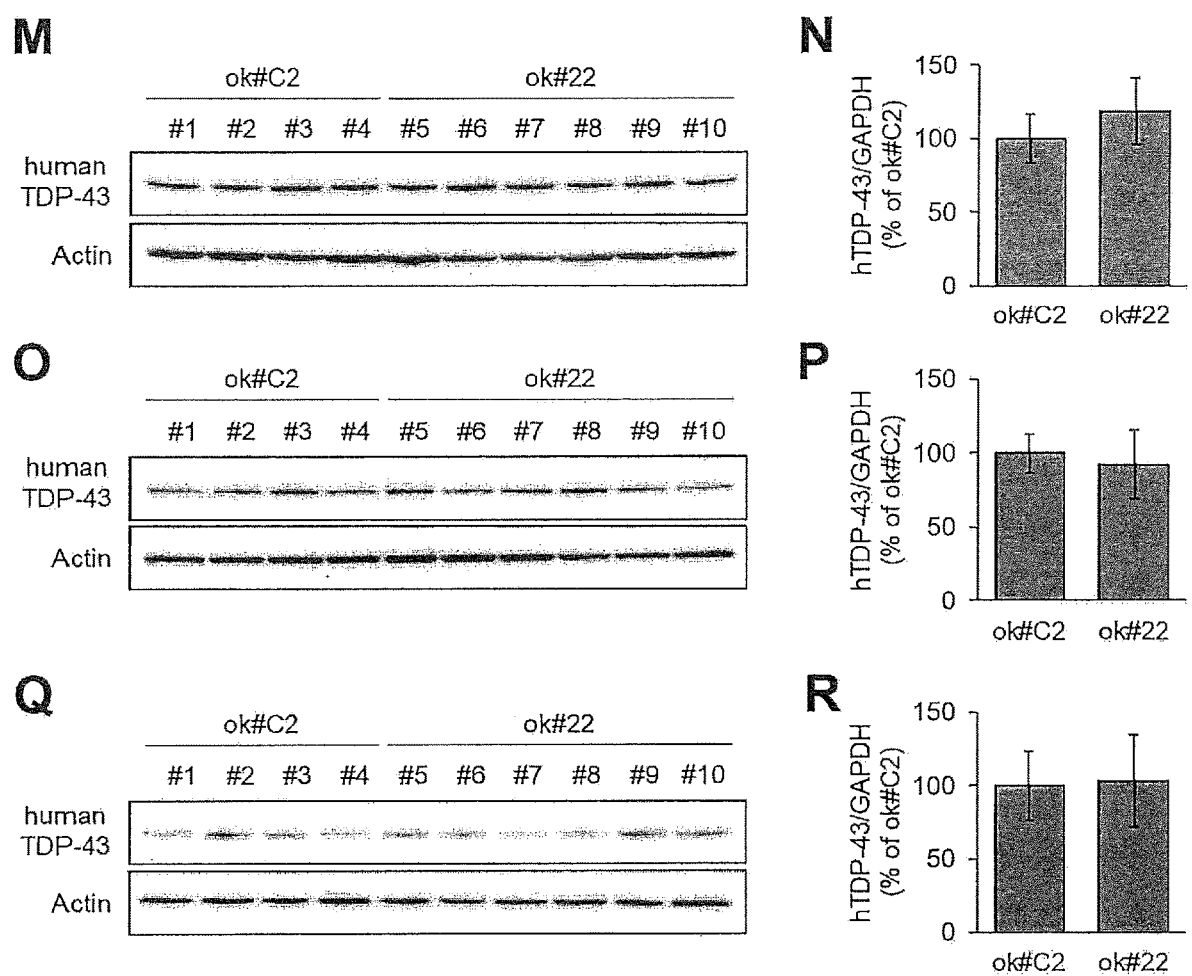

Whether or not the ASO of the present invention is effective in an individual was verified. Gapmer ASO OG #20 was administered by 200 μg to the cerebral ventricle of a human TDP-43 A315T BAC Tg mouse (6 weeks old) and analyzed 2 weeks later. As a result, human TDP-43 protein amount decreased by about 71% in the cerebral cortex, 38% in the hippocampus, and 47% in the spinal cord by OG #20 administration as compared to a mouse administered with control ASO. At this time, human TDP-43 mRNA amount decreased by about 57% in the cerebral cortex, 51% in the hippocampus, and 36% in the spinal cord. In addition, as a result of analysis at 3 months after the administration of OG #20 (200 μg), human TDP-43 protein amount decreased by about 35% in the cerebral cortex, 30% in the hippocampus, and 26% in the spinal cord as compared to a mouse administered with control ASO (FIG. 8).

Since the results also highly correlate with the results of the cultured cells in Example 1, ASOs other than Gapmer ASO OG #20 (e.g., ASO of Gapmer ASO OG #01, 09, 17, 18, 19, 06, 21, 22, 23 or 24) are considered to be similarly effective for an individual.

Example 5 In Vivo Verification of Promotion Type ASO

Whether or not the ASO of the present invention is effective in an individual was verified. Blocker ASO ok #22 was administered by 200 µg to the cerebral ventricle of a human TDP-43 A315T BAC Tg mouse (6 weeks old) and analyzed 2 weeks later. As a result, human TDP-43 protein amount increased by about 200% in the cerebral cortex, 180% in the hippocampus, and 160% in the spinal cord by OG #22 administration as compared to a mouse administered with control ASO. In addition, human TDP-43 mRNA amount decreased by about 44% in the cerebral cortex, 45% in the hippocampus, and 39% in the spinal cord, and the translation type mRNA increased by 140% in the cerebral cortex, 140% in the hippocampus, and 150% in the spinal cord. On the other hand, as a result of analysis at 3 months after the ok #22 administration (200 µg), the human TDP-43 protein amount did not increase (FIG. 8).

Since the results highly correlate with the results of the cultured cells in Example 3, ASOs other than Blocker ASOs ok #22 (e.g., ASO of Blocker ASO ok #19 or 20) are considered to be similarly effective for an individual.

Figure 10:
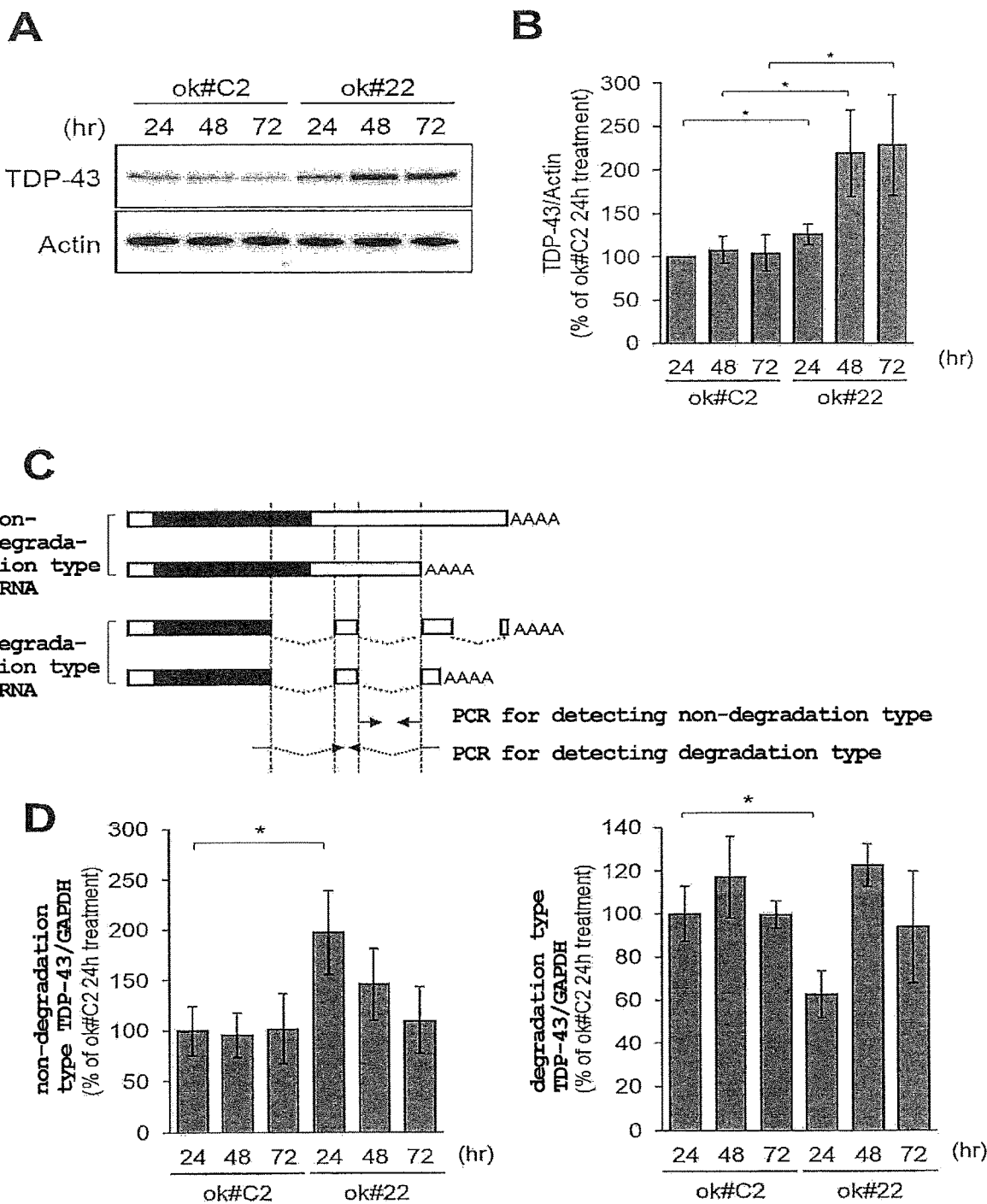
FIG. 10 shows the effect of promotion type ASO (Blocker ASO ok #22) over time on the expression of TDP-43 protein and mRNA in HEK293 cells. (A, B) The evaluation results of TDP-43 protein amount are shown. HEK293 cells were treated with 300 nM Blocker ASO for 24 hr, 48 hr and 72 hr. As a control, ASO ok #C2 was used. (B) The comparison results of TDP-43 protein amount are shown (quantification of TDP-43/Actin) (*P<0.05, versus control ASO ok #C2). (C, D) The evaluation results of TDP-43 mRNA amount are shown. HEK293 cells were treated with 300 nM Blocker ASO for 24 hr, 48 hr and 72 hr. As a control, ASO ok #C2 was used. (C) shows TDP-43 mRNA species. Non-degradation type mRNA that is maintained in the nucleus or translated, and degradation type mRNA that was spliced at potential splicing site are shown. In addition, the primer binding site when detected by PCR is shown with an arrow. (D) The comparison results of TDP-43 mRNA amount are shown. The left graph shows the quantification of non-degradation type TDP-43 mRNA/GAPDH mRNA and the right graph shows the quantification of degradation type TDP-43 mRNA/GAPDH mRNA (*P<0.05, versus control ASO ok #C2).

Example 6 Verification of Time-Course Change in Expression Level of TDP-43 by Promotion Type ASO HEK293 cells were treated with promotion type ASO (Blocker ASO ok #22) at 300 nM, the cells were recovered 24 hr, 48 hr and 72 hr later, and the protein amount (FIG. 10A, B) and mRNA amount (FIG. 10C, D) were measured. As for mRNA, non-degradation type mRNA (i.e., translation type mRNA, or RNA maintained in the nucleus (left graph) and degradation type mRNA (right graph) were measured. TDP-43 protein amount showed an increase at 48 hr later and 72 hr later. As for the TDP-43 mRNA amount, the degradation type TDP-43 mRNA amount decreased 24 hr later and the non-degradation type TDP-43 mRNA amount increased 24 hr later. Variation of these mRNA amounts was transient and was not seen 48 hr later.

This application is based on patent application No. 2017-134890 filed in Japan (filing date: Jul. 10, 2017), the contents of which are encompassed in full herein.

INDUSTRIAL APPLICABILITY

The suppression type ASO of the present invention can provide a model showing a decreased expression of TDP-43 by administration to a cell or individual. Furthermore, since the suppression type ASO can decrease the expression level of TDP-43 to suppress coagulation and accumulation of TDP-43 in the cytoplasm, and also neurodegeneration, in ALS/FTD, it greatly contribute to the development of therapeutic drugs. On the other hand, a model showing increased expression of endogenous TDP-43 can be provided by administering the promotion type ASO of the present invention to a cell or individual. Also, loss-of-function of TDP-43 in ALS/FTD can be compensated by increasing the expression level of TDP-43 by the administration of Blocker ASO, whereby neurodegeneration can be suppressed.

The invention claimed is:

1. An antisense oligonucleotide targeting TAR DNA-binding domain 43 (TDP-43) mRNA, comprising a nucleotide sequence complementary to a sequence consisting of at least 15 continuous nucleotides in the nucleotide sequence of any of SEQ ID NOs: 2-4, wherein the oligonucleotide comprises modification of one or more kinds of sugar-phosphoric acid backbone.

2. The antisense oligonucleotide according to claim 1, wherein the oligonucleotide consists of 15-30 nucleotides.

3. The antisense oligonucleotide according to claim 1, wherein the complementary nucleotide sequence is the nucleotide sequence of any of SEQ ID NOs: 45-63 (wherein thymine may be uracil).

4. The antisense oligonucleotide according to claim 1, wherein the oligonucleotide comprises 2'-O,4'-C-ethylene-bridged nucleic acid and deoxyribonucleotide.

5. The antisense oligonucleotide according to claim 4, wherein the oligonucleotide is of a gapmer type.

6. The antisense oligonucleotide according to claim 1, wherein the oligonucleotide consists of the nucleotide sequence of any of SEQ ID NOs: 11, 22-29 and 35-44.

7. An antisense oligonucleotide targeting TAR DNA-binding domain 43 (TDP-43) mRNA, comprising a nucleotide sequence complementary to a sequence consisting of at least 15 continuous nucleotides in the nucleotide sequence of SEQ ID NO: 5, wherein the oligonucleotide comprises modification of one or more kinds of sugar-phosphoric acid backbone.

8. The antisense oligonucleotide according to claim 7, wherein the oligonucleotide consists of 15-30 nucleotides.

9. The antisense oligonucleotide according to claim 7, wherein the oligonucleotide comprises 2'-O,4'-C-ethylene-bridged nucleic acid and 2'-O-methyl-modified nucleic acid.

10. The antisense oligonucleotide according to claim 7, wherein the cytosine nucleotide and thymine nucleotide are 2'-O,4'-C-ethylene-bridged nucleic acids, and adenine nucleotide and guanine nucleotide are 2'-O-methyl-modified nucleic acids.

11. The antisense oligonucleotide according to claim 7, wherein the oligonucleotide consists of the nucleotide sequence of SEQ ID NO: 84, 85 or 87.

12. The antisense oligonucleotide according to claim 1, comprising a nucleotide sequence complementary to a sequence consisting of at least 19 continuous nucleotides in the nucleotide sequence of any of SEQ ID NOs: 2-4.

13. The antisense oligonucleotide according to claim 7, comprising a nucleotide sequence complementary to a sequence consisting of at least 19 continuous nucleotides in the nucleotide sequence of SEQ ID NO: 5.

14. A method for regulating expression of TDP-43, comprising administering an effective amount of the antisense oligonucleotide according to claim 1 in vivo or in vitro.

15. A method for treating TDP-43 proteinopathy in a mammal, comprising administering an effective amount of the antisense oligonucleotide according to claim 1 to the mammal.

16. The method according to claim 15, wherein the TDP-43 proteinopathy is amyotrophic lateral sclerosis or frontotemporal dementia.

* * * * *